(12) United States Patent
Nishide et al.

(10) Patent No.: US 11,196,007 B2
(45) Date of Patent: Dec. 7, 2021

(54) ORGANIC COMPOUND, ORGANIC LIGHT-EMITTING ELEMENT, DISPLAY APPARATUS, IMAGE PICKUP APPARATUS, ELECTRONIC DEVICE, AND MOVING OBJECT

(71) Applicant: CANON KABUSHIKI KAISHA, Tokyo (JP)

(72) Inventors: Yosuke Nishide, Kawasaki (JP); Hirokazu Miyashita, Ebina (JP); Naoki Yamada, Inagi (JP); Jun Kamatani, Tokyo (JP); Shoma Hinata, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/586,583

(22) Filed: Sep. 27, 2019

(65) Prior Publication Data
US 2020/0111964 A1   Apr. 9, 2020

(30) Foreign Application Priority Data

Oct. 3, 2018 (JP) .............................. JP2018-187928
Oct. 16, 2018 (JP) .............................. JP2018-195285

(51) Int. Cl.
| | | |
|---|---|---|
| C07D 209/86 | (2006.01) | |
| H01L 51/00 | (2006.01) | |
| C07C 13/62 | (2006.01) | |
| C09K 11/06 | (2006.01) | |
| C07C 25/22 | (2006.01) | |
| C07D 333/76 | (2006.01) | |
| F21S 43/145 | (2018.01) | |
| C07D 215/06 | (2006.01) | |
| H01L 27/32 | (2006.01) | |
| H01L 51/50 | (2006.01) | |

(52) U.S. Cl.
CPC .......... *H01L 51/0056* (2013.01); *C07C 13/62* (2013.01); *C07C 25/22* (2013.01); *C07D 215/06* (2013.01); *C07D 333/76* (2013.01); *C09K 11/06* (2013.01); *F21S 43/145* (2018.01); *H01L 51/0072* (2013.01); *H01L 51/0074* (2013.01); *C07C 2603/54* (2017.05); *C09K 2211/1011* (2013.01); *C09K 2211/1018* (2013.01); *H01L 27/3234* (2013.01); *H01L 27/3248* (2013.01); *H01L 51/504* (2013.01); *H01L 51/5012* (2013.01)

(58) Field of Classification Search
CPC .................................................. H01L 51/0056

USPC ............................................................ 585/26
See application file for complete search history.

(56) References Cited

U.S. PATENT DOCUMENTS 8,822,043 B2 * 9/2014 Kamatani ............... C07C 13/62
428/690
8,963,813 B2 * 2/2015 Kamatani ............ C07D 215/06
345/76

FOREIGN PATENT DOCUMENTS

JP  2000-34234 A  2/2000
JP  2013-43846 A  3/2013

OTHER PUBLICATIONS

Dorwald F. A. Side Reactions in Organic Synthesis, 2005, Wiley: VCH, Weinheim p. IX of Preface p. 1-15.*
Jianzhong, Chinese Science Bulletin 2004 vol. 49 No. 8, 797-802.*

* cited by examiner

*Primary Examiner* — Nizal S Chandrakumar
(74) *Attorney, Agent, or Firm* — Canon U.S.A., Inc., IP Division

(57) ABSTRACT

An organic compound represented by formula (1) and an organic compound represented by formula (2). These organic compounds provide high color purity.

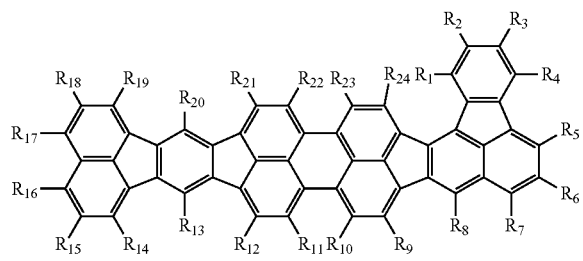

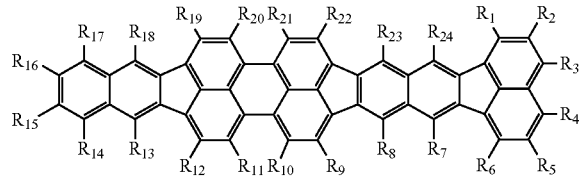

In formulae (1) and (2), $R_1$ to $R_{24}$ are each independently selected from the group consisting of a hydrogen atom and a substituent.

20 Claims, 8 Drawing Sheets

ORGANIC COMPOUND, ORGANIC LIGHT-EMITTING ELEMENT, DISPLAY APPARATUS, IMAGE PICKUP APPARATUS, ELECTRONIC DEVICE, AND MOVING OBJECT

BACKGROUND

Field of the Invention

One embodiment of the present disclosure relates to an organic compound, an organic light-emitting element, a display apparatus, an image pickup apparatus, an electronic device, and a moving object.

Description of the Related Art

An organic light-emitting element (also referred to as an organic electroluminescence element or an organic EL element) is an electronic element including a pair of electrodes and an organic compound layer disposed between the electrodes. By injecting electrons and holes through the pair of electrodes, excitons of a luminescent organic compound in the organic compound layer are generated. The organic light-emitting element emits light when the excitons return to their ground state.

Recent progress in organic light-emitting elements has been noticeable. For example, low driving voltages, various emission wavelengths, high-speed response, and thinner and lighter light-emitting devices have been enabled.

The sRGB standard and the Adobe RGB standard have been known as color reproduction ranges used for displays, and materials suitable for such color reproduction ranges have been demanded. Recently, there has been a demand for reproduction of BT-2020, which is the standard having a wider color reproduction range.

Luminescent organic compounds have been actively created to date. Japanese Patent Laid-Open No. 2000-34234 (hereinafter PTL 1) discloses an organic compound represented by structural formula 1-A below and having excellent light-emitting properties. This compound is referred to as compound 1-A in this specification. Japanese Patent Laid-Open No. 2013-43846 (hereinafter PTL 2) discloses a compound represented by structural formula 1-B below. This compound is referred to as compound 1-B in this specification.

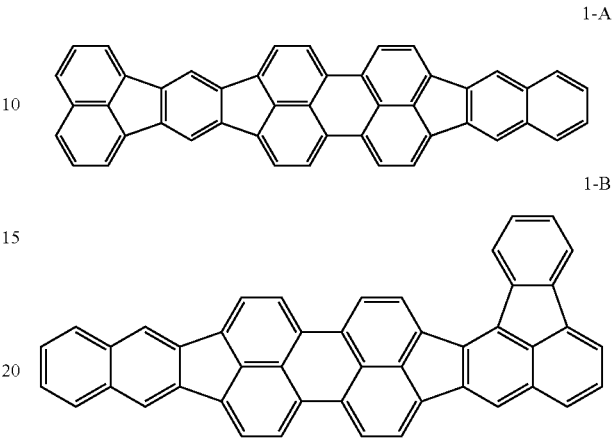

1-A

1-B

An organic light-emitting element including the organic compound disclosed in PTL1 or PTL2 emits red light, but not sufficiently. Specifically, to achieve a wider color reproduction range, an organic compound that emits longer-wavelength red light is required. Introducing a substituent into an organic compound can achieve longer-wavelength light emission but may destabilize the compound.

SUMMARY

The present disclosure has been made in view of the above disadvantages, and an aspect thereof is to provide an organic compound having a basic skeleton that emits long-wavelength red light.

An organic compound according to one embodiment of the present disclosure is represented by formula (1) or formula (2) below.

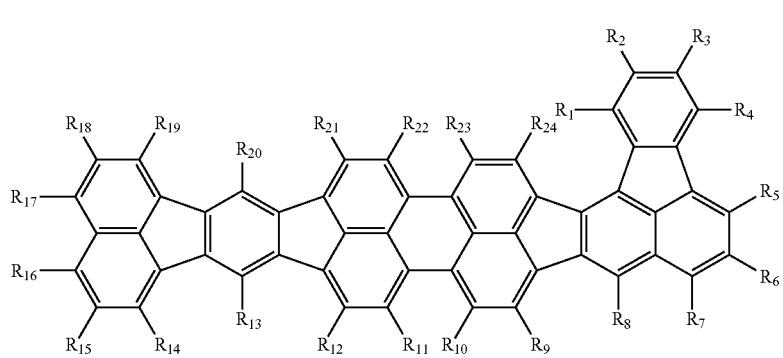

(1)

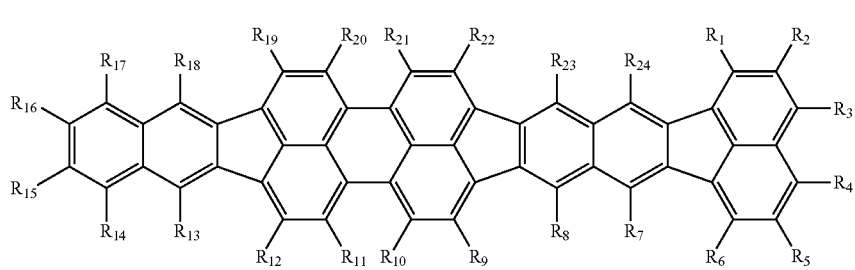

(2)

In formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

In formula (2), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

Further features of the present disclosure will become apparent from the following description of exemplary embodiments with reference to the attached drawings.

DESCRIPTION OF THE EMBODIMENTS

Figure 1:
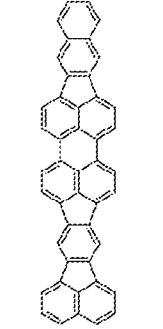
FIG. 1 is a comparison of the planarity of exemplary compound A10 according to an embodiment and comparative compound (1).

An organic compound according to one embodiment of the present disclosure is an organic compound represented by formula (1) or formula (2) below. The term "basic skeleton" refers, for example, to a structure represented by formulae (1) and (2) where $R_1$ to $R_{24}$ are each a hydrogen atom. The term "basic skeleton" may also refer to only the condensed-ring moiety in the compound.

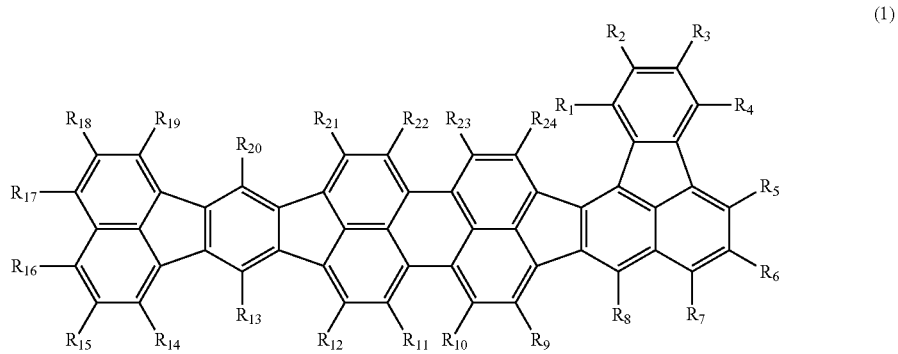

(1)

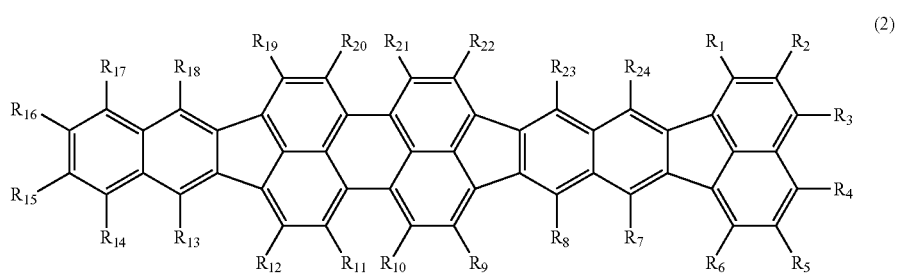

(2)

In formulae (1) and (2), $R_1$ to $R_{24}$ in the basic skeletons are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

In formulae (1) and (2), the halogen atom may be, for example, but is not limited to, fluorine, chlorine, bromine, or iodine.

In formulae (1) and (2), the alkyl group may be an alkyl group having 1 to 10 carbon atoms. Specific examples of such alkyl groups include methyl, ethyl, n-propyl, isopropyl, n-butyl, isobutyl, tertiary butyl, secondary butyl, octyl, cyclohexyl, 1-adamantyl, and 2-adamantyl.

In formulae (1) and (2), the alkoxy group may be an alkoxy group having 1 to 10 carbon atoms. Specific examples of such alkoxy groups include methoxy, ethoxy, propoxy, 2-ethyl-octyloxy, and benzyloxy.

In formulae (1) and (2), the amino group may be substituted with an alkyl group or an aryl group. The alkyl group may be an alkyl group having 1 to 10 carbon atoms. The aryl group may be an aryl group having 6 to 18 carbon atoms. Specific examples of such amino groups include N-methylamino, N-ethylamino, N,N-dimethylamino, N,N-diethylamino, N-methyl-N-ethylamino, N-benzylamino, N-methyl-N-benzylamino, N,N-dibenzylamino, anilino, N,N-diphenylamino, N,N-dinaphthylamino, N,N-difluorenylamino, N-phenyl-N-tolylamino, N,N-ditolylamino, N-methyl-N-phenylamino, N,N-dianisolylamino, N-mesityl-N-phenylamino, N,N-dimesitylamino, N-phenyl-N-(4-tertiary butylphenyl)amino, N-phenyl-N-(4-trifluoromethylphenyl)amino, and N-piperidyl.

In formulae (1) and (2), the aryl group may be an aryl group having 6 to 18 carbon atoms. Specific examples of such aryl groups include phenyl, naphthyl, indenyl, biphenyl, terphenyl, fluorenyl, fluoranthenyl, and phenanthrenyl.

In formulae (1) and (2), the heterocyclic group may be a heterocyclic group having 3 to 17 carbon atoms. Examples of heteroatoms include oxygen, sulfur, and nitrogen, and the number of heterocyclic groups may be one or two or more. Two or more heterocyclic groups may be different from each other. Specific examples of such heterocyclic groups include, but are not limited to, pyridyl, oxazolyl, oxadiazolyl, thiazolyl, thiadiazolyl, carbazolyl, acridinyl, and phenanthrolyl.

In formulae (1) and (2), the aryloxy group may be, for example, but is not limited to, a phenoxy group or a thienyloxy group.

In formulae (1) and (2), the silyl group may be, for example, but is not limited to, a triphenylsilyl group.

Examples of substituents that the alkyl group and the alkoxy group above may further have include halogen atoms. When the alkyl group or the alkoxy group has a halogen atom as a substituent, the halogen atom may be fluorine.

Examples of substituents that the aryl group, the heterocyclic group, and the aryloxy group above may further have include, but are not limited to, C1 to C10 alkyl groups such as methyl, ethyl, n-propyl, isopropyl, n-butyl, and tertiary butyl; aralkyl groups such as benzyl; C6 to C12 aryl groups such as phenyl and biphenyl; C3 to C11 heterocyclic groups such as pyridyl, pyrrolyl, furanyl, and thiol; amino groups such as dimethylamino, diethylamino, dibenzylamino, diphenylamino, and ditolylamino; alkoxy groups such as methoxy, ethoxy, and propoxy; aryloxy groups such as phenoxy; halogen atoms such as fluorine, chlorine, bromine, and iodine; and a cyano group.

In this embodiment, $R_1$ to $R_{24}$ in formulae (1) and (2) may each independently be selected from the group consisting of a hydrogen atom and a substituted or unsubstituted aryl group.

Next, a method for synthesizing an organic compound according to one embodiment of the present disclosure will be described. The organic compound according to this embodiment is synthesized, for example, according to the following reaction scheme.

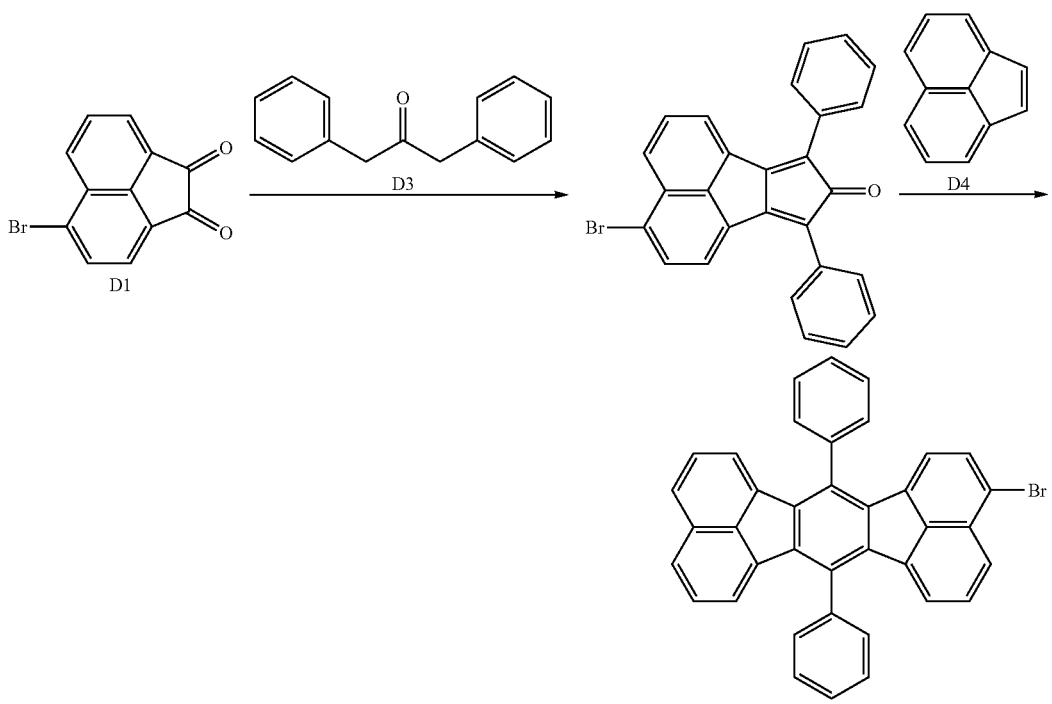

7
-continued
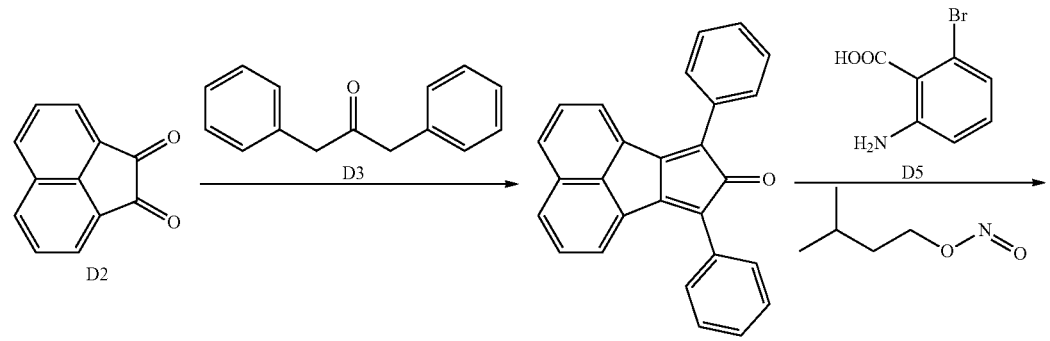
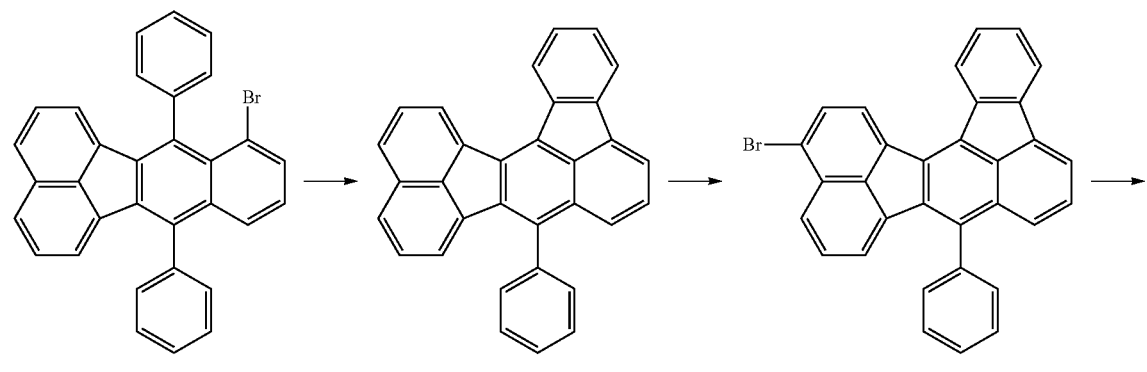
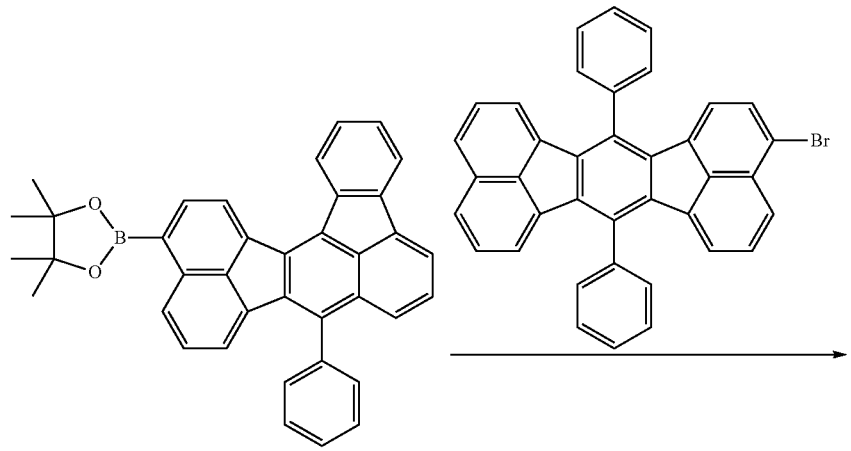
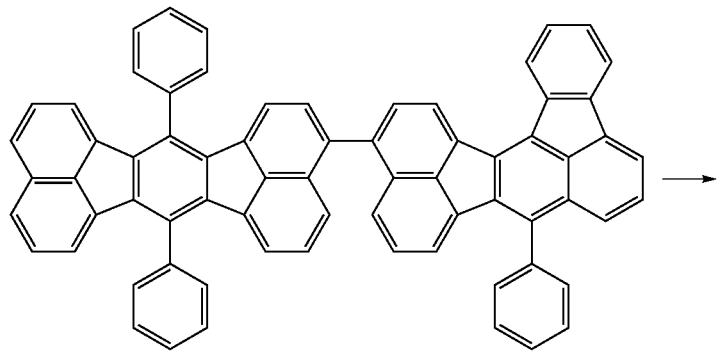

-continued

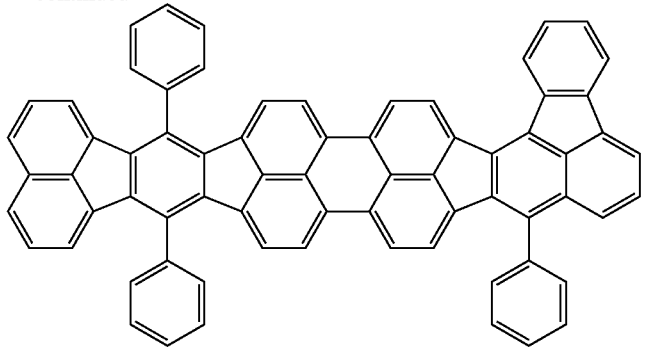

As shown by the above synthesis scheme, the organic compound according to one embodiment of the present disclosure is synthesized by using, as raw materials, compounds designated by (a) to (d) below.

(a) Acenaphthenequinone derivatives (D1, D2)
(b) Dibenzyl ketone derivative (D3)
(c) Acenaphthylene derivative (D4)
(d) Bromoanthranilic acid derivative (D5)

By appropriately introducing substituents into the compounds designated by (a) to (d), an organic compound represented by formula (1) where $R_1$ to $R_{24}$ have desired substituents can be obtained.

In each reaction, a metal catalyst such as palladium, nickel, or phosphorus can be used to increase the rate of formation and the rate of reaction.

The organic compound represented by formula (2) can be synthesized, for example, according to the following scheme.

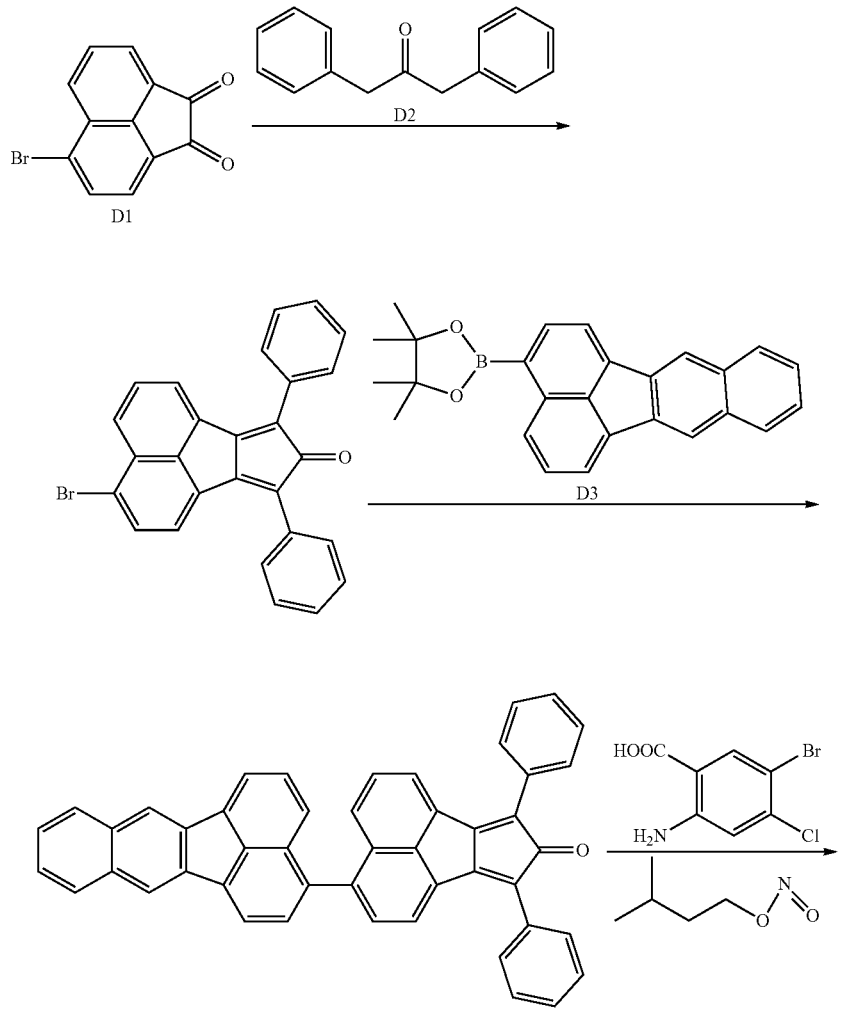

-continued

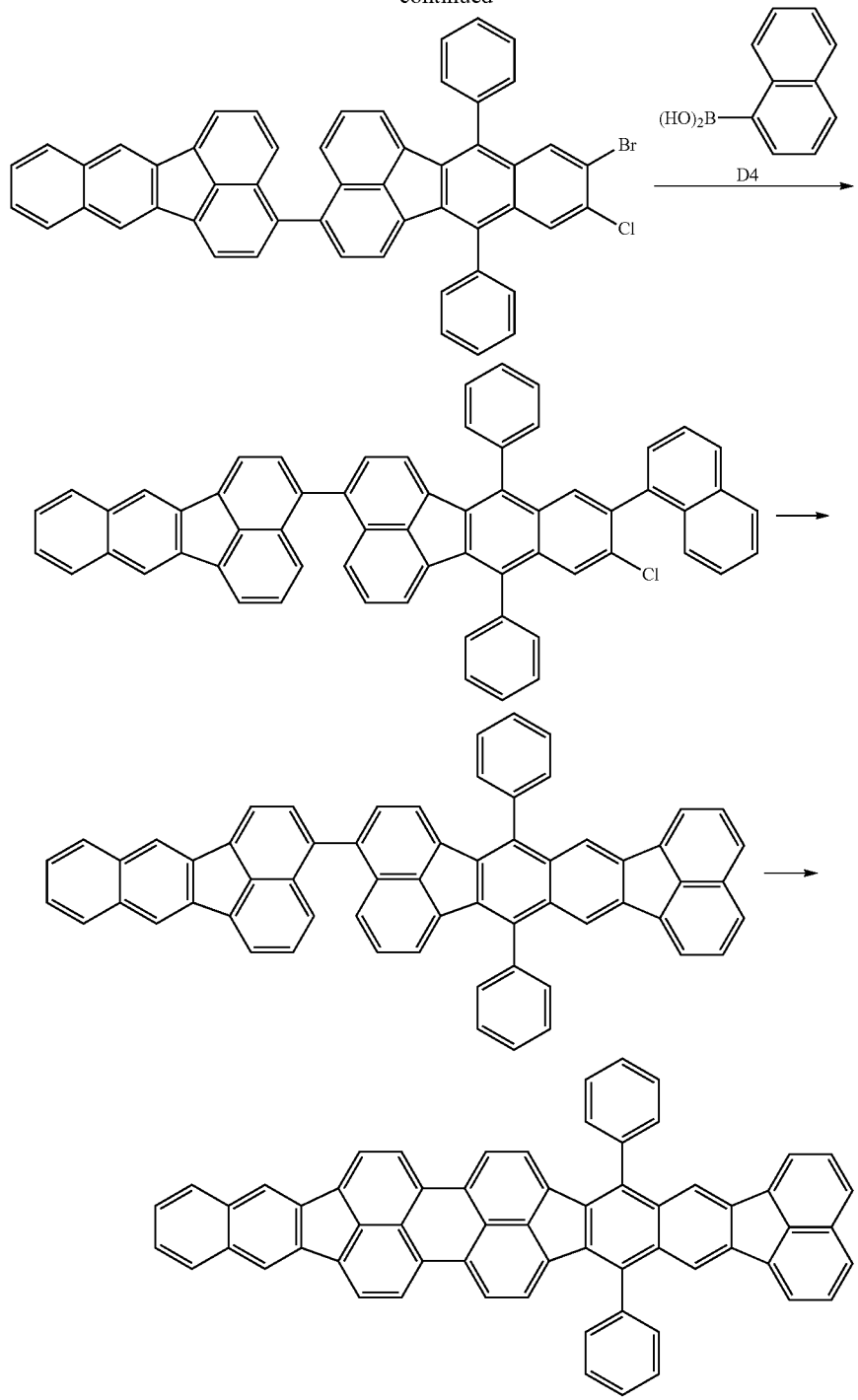

As shown by the above synthesis scheme, the organic compound according to this embodiment is synthesized by using, as raw materials, compounds designated by (a) to (d) below.
(a) Acenaphthenequinone derivative (D1)
(b) Dibenzyl ketone derivative (D2)
(c) Benzofluoranthene derivative (D3)
(d) Naphthalene derivative (D4)

By appropriately introducing substituents into the compounds designated by (a) to (d), hydrogen at any of $R_1$ to $R_{24}$ in formula (1) will be substituted with desired groups other than hydrogen. In the above synthesis scheme, D1 to D4 can each be changed to synthesize various organic compounds.

The organic compound according to this embodiment has the following features and thus is a stable compound that emits red light with high color purity.

(1) The emission wavelength of the basic skeleton itself is in a deep red range.

(2) The basic skeleton consists of a hydrocarbon.

(3) The compound has an asymmetric structure and thus has low crystallinity.

These features will be described below.

(1) The Emission Wavelength of the Basic Skeleton Itself is in a Deep Red Range.

In creating the organic compound represented by formula (1), the present inventors focused on the basic skeleton itself. Specifically, the inventors focused on whether the emission wavelength of a molecule consisting of the basic skeleton, that is, a molecule in which $R_1$ to $R_{24}$ are hydrogen, falls within a desired wavelength range.

In this embodiment, the desired wavelength range means a deep red range. Specifically, the maximum peak wavelength is in the range of 610 nm to 640 nm in a dilute solution.

The emission wavelength will be described with reference to an exemplary compound of the present disclosure and comparative compounds similar to the exemplary compound. Here, the comparative compounds are comparative compound (1) and comparative compound (2) shown in Table 1 below. Comparative compound (1) is a compound including, as a basic skeleton, compound 1-A disclosed in PTL 1, and comparative compound (2) is a compound including, as a basic skeleton, compound 1-B disclosed in PTL 2. Comparative compound (1) and comparative compound (2) are each provided with phenyl groups. The phenyl groups are provided for accurate measurement of emission wavelengths. If the phenyl groups are not provided, molecules may be associated with each other by intermolecular interaction to influence the measurement of emission wavelengths. The phenyl groups are provided at positions not influencing conjugation of molecules and thus have little influence on emission wavelength. Among exemplary compounds, exemplary compound A10, which is provided with phenyl groups as with the comparative compounds, was used to evaluate the present disclosure.

The exemplary compound of the present disclosure is exemplary compound A10. Exemplary compound A10 is an organic compound having a basic skeleton represented by formula (1) above, where $R_1$ to $R_7$, $R_9$ to $R_{12}$, $R_{14}$ to $R_{19}$, and $R_{21}$ to $R_{24}$ are hydrogen, and $R_8$, $R_{13}$, and $R_{20}$ are phenyl.

Emission wavelengths of exemplary compound A10, comparative compound (1), and comparative compound (2) were compared. The results are shown in Table 1 below. The emission wavelengths were measured using an F-4500 manufactured by Hitachi, Ltd. by performing photoluminescence measurement of a diluted toluene solution at an excitation wavelength of 350 nm at room temperature.

TABLE 1

| | Structural formula | Maximum emission wavelength | Emission color |
|---|---|---|---|
| Comparative compound (1) | 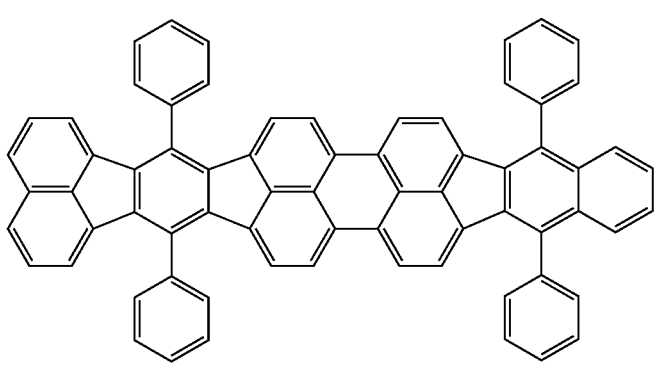 [SMILES: c1ccc(-c2c3c(c(-c4ccccc4)c4ccccc24)-c2ccc4c5ccc6c7c(-c8ccccc8)c8c9cccc%10cccc(c8c(-c8ccccc8)c7c7ccc(c8ccc-3c2c84)c5c76)c%109)cc1] | 608 nm | Red |
| Comparative compound (2) | 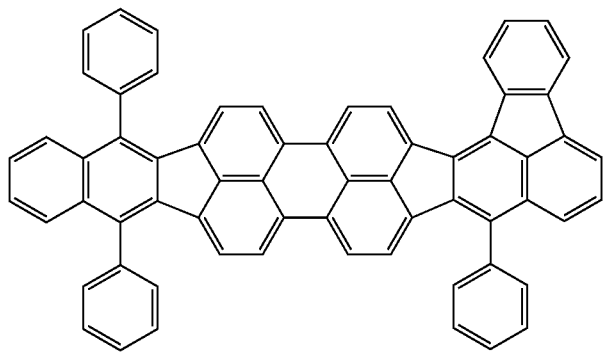 [SMILES: c1ccc(-c2c3c(c(-c4ccccc4)c4ccccc24)-c2ccc4c5ccc6c7c(ccc(c8ccc-3c2c84)c57)c2c(-c3ccccc3)c3cccc4c5ccccc5c(c34)c62)cc1] | 607 nm | Red |

TABLE 1-continued

| | Structural formula | Maximum emission wavelength | Emission color |
|---|---|---|---|
| Exemplary compound A10 | | 616 nm | Deep red |

Table 1 shows that comparative compound (1) and comparative compound (2) emit red light, but not in the desired wavelength range. By contrast, exemplary compound A10 has a maximum emission wavelength in the desired wavelength range and thus exhibits an emission color suitable for red in display standards. Thus, the basic skeleton of the present disclosure can emit longer-wavelength red light. The term "maximum emission wavelength" refers to a wavelength at which a maximum peak exists in an emission spectrum. Therefore, the maximum emission wavelength can also be referred to as the maximum peak wavelength.

(2) The Basic Skeleton Consists of a Hydrocarbon.

The organic compound represented by formula (1) has a basic skeleton consisting of a hydrocarbon. Substituents may also consist of hydrocarbons. A longer emission wavelength of an organic compound can be achieved, for example, by using the effect of electron-donating properties of a substituent. For example, an amino group or the like may be bonded in a molecular structure. However, when a compound having an unstable bond with a low binding energy, such as an amino group, is used as a luminescent material constituting an organic EL element, the compound is likely to deteriorate during the operation of the element. Deterioration of the compound shortens the service life of the organic EL element. By contrast, the compound represented by formula (1) according to one embodiment of the present disclosure consists of a hydrocarbon and thus has a high binding energy, thus providing an organic EL element with a long service life.

When the basic skeleton is provided with a substituent, the substituent may consist of a hydrocarbon. This is because the hydrocarbon has a high binding energy and thus stabilizes the compound.

For example, referring to compounds A-1, A-2, and B-1 shown below, the bond linking a carbazole ring with a phenyl group and the bond linking an amino group with a phenyl group (nitrogen-carbon bond) are bonds with low binding stability. The bond linking carbon with carbon as shown in compound B-1 has higher binding stability.

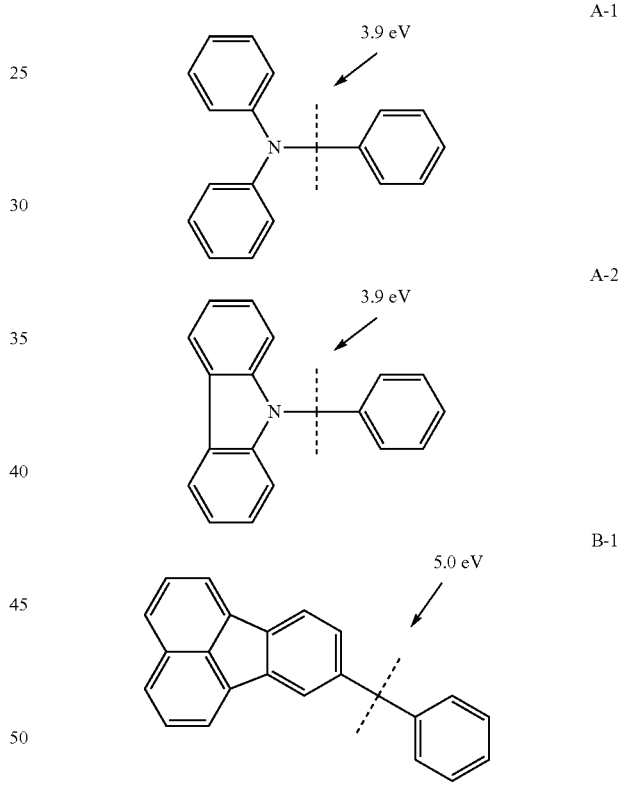

(3) The Basic Skeleton is Nonplanar and Thus Provides Low Crystallinity.

The organic compound according to one embodiment of the present disclosure has an extended conjugation length so that light emitted by the basic skeleton itself is deep red. Compounds having long conjugation lengths tend to have high molecular planarity and thus are easily crystallized by intermolecular interaction. When an organic compound is crystallized, the organic compound itself may disadvantageously undergo changes in properties, such as a decrease in sublimability and the occurrence of concentration quenching.

Thus, the organic compound according to one embodiment of the present disclosure is designed so as to have a molecular structure with low symmetry and has low molecular planarity. As compared with molecules with high symmetry, molecules with low symmetry are not easily crystallized because the molecules with low symmetry are inhibited from being orderly stacked on top of each other. Molecules that are not easily crystallized have high sublimability and are unlikely to undergo concentration quenching. Therefore, the structure of molecules may be asymmetric to reduce the likelihood of crystallization.

Here, high sublimability means that the difference between the sublimation temperature of an organic compound and the thermal decomposition temperature of the organic compound is large and the sublimation temperature is lower than the thermal decomposition temperature. An organic compound having low sublimability may be thermally decomposed during sublimation, thus forming a decomposition product of the organic compound. The decomposition product of the organic compound may have an undesired influence such as an unexpected reaction. Thus, the sublimability of an organic compound may be high to reduce the likelihood of the formation of a decomposition product.

In this embodiment, exemplary compound A10 according to this embodiment and comparative compound (1) were compared with each other in terms of the planarity of their basic skeletons. The comparison of the planarity is shown in FIG. 1.

As shown in FIG. 1, the basic skeleton of comparative compound (1) was planar. Comparative compound (1) was estimated to have a strong intermolecular interaction and high crystallinity. By contrast, the basic skeleton of exemplary compound A10 had low planarity, and thus exemplary compound A10 was estimated to have low crystallinity.

Accordingly, the organic compound according to one embodiment of the present disclosure has a basic skeleton with low planarity and thus is a compound that is not easily crystallized and capable of maintaining its sublimability, while also having a conjugation length that allows light emission in the long-wavelength range.

An organic compound that satisfies the following conditions (4) to (6) in addition to the above conditions (1) to (3) is preferred. This is because when the conditions (4) to (6) are satisfied, crystallization is further reduced, leading to improved sublimability and reduced concentration quenching. Improved sublimability enables an increase in purity of a material through sublimation purification and facilitates the production of an organic light-emitting element through vapor deposition. This can decrease the amount of impurities contained in the organic light-emitting element, thus suppressing a decrease in light emission efficiency due to impurities and a decrease in driving durability. Reduced concentration quenching is preferred to improve the light emission efficiency of the organic light-emitting element.

(4) The organic compound has a bulky substituent at any of $R_8$, $R_{13}$, and $R_{20}$.
(5) The organic compound has a substituent that covers a molecular plane.
(6) The compound is composed of SP2 hybrid orbitals.

These features will be described below.

(4) The Organic Compound has a Bulky Substituent at any of $R_8$, $R_{13}$, and $R_{20}$.

When the organic compound according to one embodiment of the present disclosure has a substituent in its basic skeleton, the organic compound can have reduced molecular crystallinity. Reduced crystallinity leads to reduced concentration quenching and improved sublimability as described above.

The organic compound according to one embodiment of the present disclosure has a highly planar portion, and thus if the organic compound is unsubstituted, excimers are readily formed by intermolecular interaction. The formation of excimers can be suppressed by weakening the intermolecular interaction, for example, by providing a substituent.

Specifically, when the substituent provided is an alkyl group, methyl, ethyl, propyl, butyl, hexyl, and octyl are preferred, and isopropyl and tertiary butyl, which are sterically large, are particularly preferred. When the substituent provided is an aryl group, phenyl and naphthyl are preferred. Among aryl groups, substituted phenyls such as xylyl, mesityl, isopropylphenyl, and tertiary butylphenyl are preferred. This is because these substituted phenyls have greater excluded volume effects than phenyl and thus can weaken the intermolecular interaction.

Fluorine is also preferred as a substituent because of the same reason. In addition, fluorine also has the effect of improving film properties when a film is formed by application of a liquid containing the organic compound.

Hereinafter, substituent positions that can effectively weaken the intermolecular interaction will be described.

The intermolecular interaction, specifically, the π-π interaction between molecules tends to increase as a result of an extension of the π-plane. The present inventors focused on π-electrons which cause the π-π interaction, particularly, on π-electron density. The electron density of a basic skeleton was estimated by molecular orbital calculations.

The molecular orbital calculations were performed by density functional theory (DFT), which is now widely used. The B3LYP functional and the 6-31G* basis function were used. The molecular orbital calculations were performed by Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010), which is now widely used.

As shown below, numerical values each represent a partial charge of a carbon atom, and carbon atoms located at $R_8$, $R_{13}$, and $R_{20}$ in formula (1) have high electron densities. In the following structural formulae, numerical values representing electron densities at $R_8$, $R_{13}$, and $R_{20}$ are underlined. These carbon atoms are readily influenced by intermolecular interaction because of their high π-electron densities. Thus, substituents may be provided at these positions.

Accordingly, to weaken the intermolecular interaction, a substituent may be provided at least one of $R_8$, $R_{13}$, and $R_{20}$ where the electron density is high.

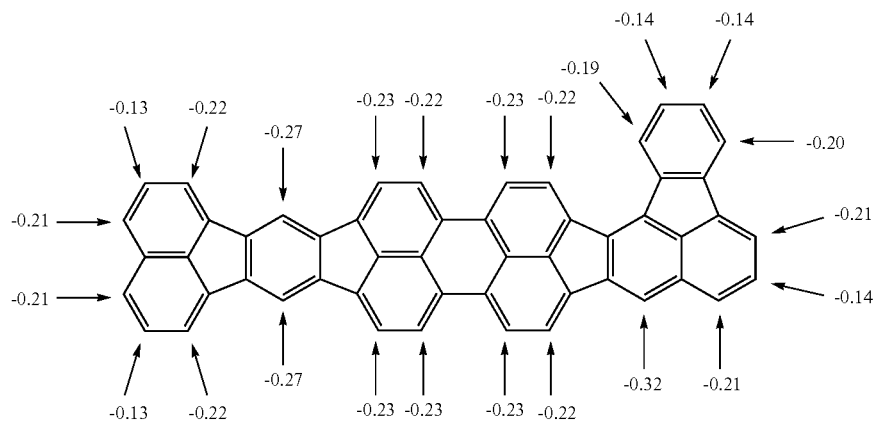 [SMILES: c1ccc2c(c1)c1cccc3cc4c5ccc6c7ccc8c9cc%10c(cc9c9ccc(c%11ccc(c5c6%11)c4c2c31)c7c89)c1cccc2cccc%10c21]

Exemplary compounds A24 and A10 of the present disclosure were compared with each other in terms of sublimability, thereby comparing the influence of intermolecular interaction. The results are shown in Table 2.

TABLE 2

| | Structural formula | Molecular weight | Sublimability |
|---|---|---|---|
| Exemplary compound A24 | | 800.94 | Purity decreased after sublimation |
| Exemplary compound A10 | | 877.03 | Purity did not decrease after sublimation |

Exemplary compound A10 has a smaller molecular weight than exemplary compound A24 and thus is estimated to be a compound disadvantageous in terms of sublimability, but exemplary compound A10 had higher sublimability. The purity of exemplary compound A24 decreased after sublimation purification, whereas the purity of exemplary compound A10 did not decrease after sublimation purification. This is because exemplary compound A10 has bulky substituents at substitution positions that effectively weaken the intermolecular interaction, as described above. By contrast, exemplary compound A24 has a basic skeleton having at its center an exposed conjugate plane, which facilitates stacking of molecules, and thus exemplary compound A24 has lower sublimability than exemplary compound A10. However, compounds such as exemplary compound A24 that are influenced by intermolecular interaction are suitable for use as high-mobility materials such as organic thin-film transistors.

(5) The Organic Compound has a Substituent that Covers a Molecular Plane.

When the organic compound according to one embodiment of the present disclosure has an appropriately selected substituent in its basic skeleton, the intermolecular interaction can be weakened. Specifically, the intermolecular interaction can be more effectively weakened by introducing a substituent that covers the conjugate plane at the center of the basic skeleton. In the organic compound according to one embodiment of the present disclosure, intermolecular interaction may cause π-conjugated planes of basic skeletons to be stacked on top of each other and orderly arranged.

Thus, a substituent that shields the π-conjugated plane was provided to weaken the intermolecular interaction. Specifically, as in exemplary compound A16 or A18, a methyl or phenyl group was provided at an ortho position of a substituent phenyl group to cover the π-conjugated plane, thereby weakening the intermolecular interaction.

Exemplary compound A10, exemplary compound A16, and exemplary compound A18 were compared with each other in terms of the effect of a shielding substituent. The results are shown in Table 3.

TABLE 3

| | Structural formula | Molecular weight | Decomposition temperature - sublimation temperature |
|---|---|---|---|
| Exemplary compound A10 | | 877.03 | 20° C. |

TABLE 3-continued

| Structural formula | Molecular weight | Decomposition temperature - sublimation temperature |
|---|---|---|
| Exemplary compound A16 | 905.09 | 30° C. |
| Exemplary compound A18 | 1029.23 | 40° C. |

Sublimation temperatures are influenced by molecular weights, and thus the sublimation temperature tends to increase as the molecular weight increases. As a result, the sublimability tends to decrease as the molecular weight increases.

However, regarding the exemplary compounds of the present disclosure, exemplary compound A10 is estimated to have highest sublimability because exemplary compounds A16 and A18 have larger molecular weights than exemplary compound A10, but actually, exemplary compound A10 had lowest sublimability. This is because the bulky substituent effectively weakened the intermolecular interaction.

The sublimation temperature is a temperature at which a sufficient sublimation rate is reached after sublimation purification is initiated by gradually raising the temperature at a degree of vacuum of $1\times10^{-1}$ Pa under a flow of Ar. The decomposition temperature is a temperature at which the weight loss determined by TG/DTA measurement reaches 5%.

Accordingly, when the condition (5) is satisfied, the organic compound according to one embodiment of the present disclosure has a large difference between the sublimation temperature and the thermal decomposition temperature and thus has high sublimability.

(6) The Compound Consists of SP2 Hybridized Carbon Atoms.

The organic compound according to one embodiment of the present disclosure has a basic skeleton having an extended conjugation length so that the basic skeleton itself emits red light. Thus, the organic compound has a portion with high molecular planarity and has a strong intermolecular interaction, and thus the sublimation temperature during sublimation purification is high. Thus, the organic compound may be stable under thermal energy at high temperature.

The present inventors discovered that the stability of the compound is further improved when the basic skeleton consists of SP2 hybridized carbon atoms and, in addition, the substituent provided is also composed of SP2 hybridized carbon.

Here, the effect of substituents will be described with reference to exemplary compound A16 and exemplary compound A18. As shown in Table 3, exemplary compound A18 has a larger molecular weight, and exemplary compound A18 has a larger difference between the decomposition temperature and the sublimation temperature. As described above, as the difference between the decomposition temperature and the sublimation temperature increases, the temperature margin in sublimation purification increases. Thus, exemplary compound A18 has higher sublimability.

This can be explained as follows: the substituent of exemplary compound A18 is an ortho-biphenyl group and thus has high stability, and furthermore, the effect of shielding a molecular plane is increased by the bulky phenyl group as in condition (5).

Taken together, the organic compound according to one embodiment of the present disclosure has the features (1) to (3) above and thus is an organic compound that has a basic skeleton whose emission wavelength is in the red range and that has maintained sublimability, as compared with comparative compounds 1 and 2. Furthermore, when having the features (4) to (6), the compound has a weak intermolecular interaction and high sublimability. Using this compound can provide an organic light-emitting element that has high efficiency and high element durability and that emits deep red light.

The organic compound represented by formula (2), which is an organic compound according to one embodiment of the present disclosure, has the following features and thus is a stable compound that emits red light with high color purity. Furthermore, the organic compound can provide an organic light-emitting element that emits light with high efficiency and has high durability. To distinguish from the features of the organic compound represented by formula (1), the features are numbered from (1) again.

(1) The emission wavelength of the basic skeleton itself is in a red range with high color purity.
(2) The skeleton has a high transition dipole moment and thus provides a high quantum yield.
(3) The organic compound does not have highly reactive SP2 carbon and thus has high thermal stability.

These features will be described below.

The S1 (singlet excited state) wavelength, the oscillator strength, and the dihedral angle of molecular structures shown in Tables 4 and 5 were calculated by using the same molecular orbital calculations as used for formula (1).

(1) The Emission Wavelength of the Basic Skeleton Itself is in a Red Range with High Color Purity.

In inventing the organic compound represented by formula (2), the present inventors focused on the basic skeleton itself. Specifically, the inventors attempted to provide an organic compound in which the emission wavelength of a molecule consisting of the basic skeleton falls within a desired emission wavelength range. In this embodiment, the desired emission wavelength range means a red range with high color purity. Specifically, the maximum emission wavelength is in the range of 595 nm to 630 nm in a dilute solution.

Next, the properties of the basic skeleton of the organic compound according to the present disclosure will be described while comparing with comparative compounds having structures similar to that of the organic compound according to one embodiment of the present disclosure. Specifically, compounds represented by formulae (3) and (4) below are used as the comparative compounds. Exemplary compound C2, which has a basic skeleton represented by formula (2) where $R_1$ to $R_7$, $R_9$ to $R_{22}$, and $R_{24}$ are each a hydrogen atom and $R_8$ and $R_{23}$ are each a phenyl group, is used as an organic compound according to the present disclosure.

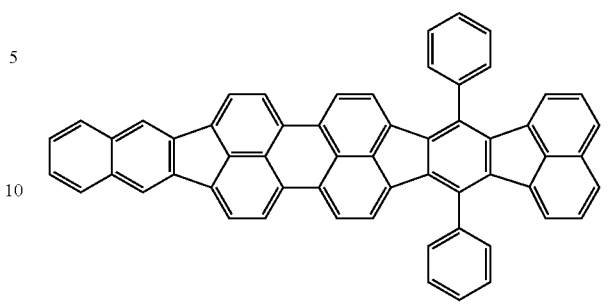

(3)

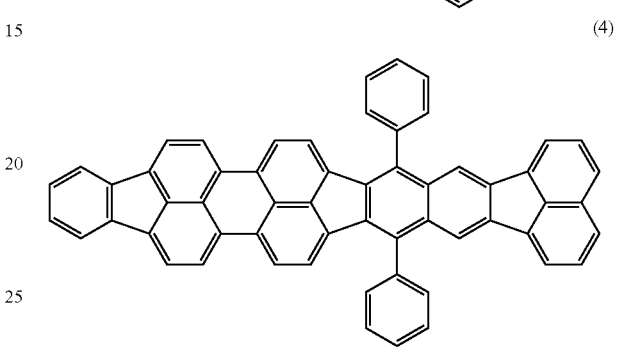

(4)

Exemplary compound C2

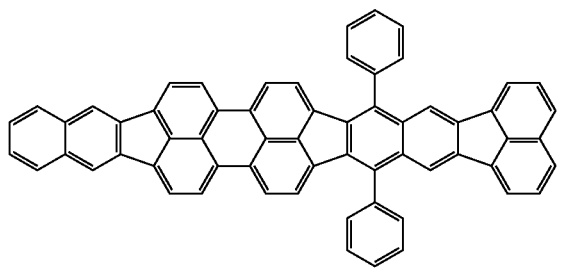

The present inventors compared measured maximum emission wavelengths of comparative compounds (3) and (4) and exemplary compound C2 of the present disclosure. The results are shown in Table 4. The emission wavelengths were measured using an F-4500 manufactured by Hitachi, Ltd. by performing photoluminescence measurement of a diluted toluene solution at an excitation wavelength of 350 nm at room temperature.

TABLE 4

| Compound | Molecular structure | Measured value Maximum emission wavelength/nm |
|---|---|---|
| (3) | 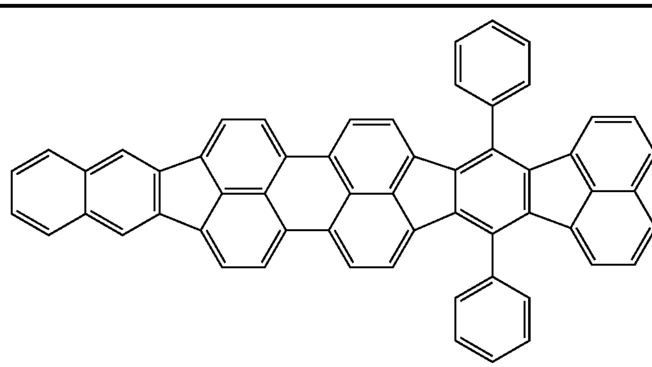 | 591 |

TABLE 4-continued

| Compound | Molecular structure | Measured value Maximum emission wavelength/nm |
|---|---|---|
| (4) | 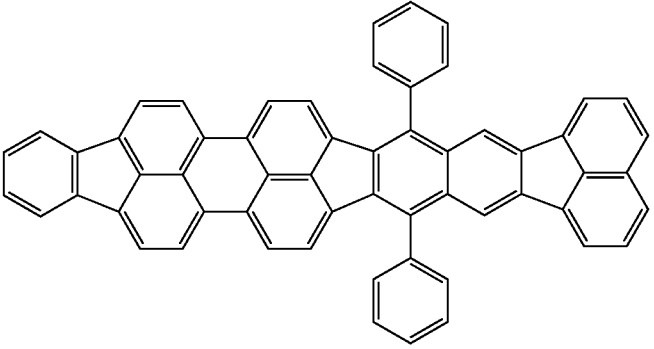 [SMILES: c1ccc(-c2c3cc4c(cc3c(-c3ccccc3)c3c5ccc6c7ccc8c9c(ccc(c%10ccc(c23)c5c%106)c97)-c2ccccc2-8)c2cccc3cccc4c32)cc1] | 588 |
| Exemplary compound C2 | 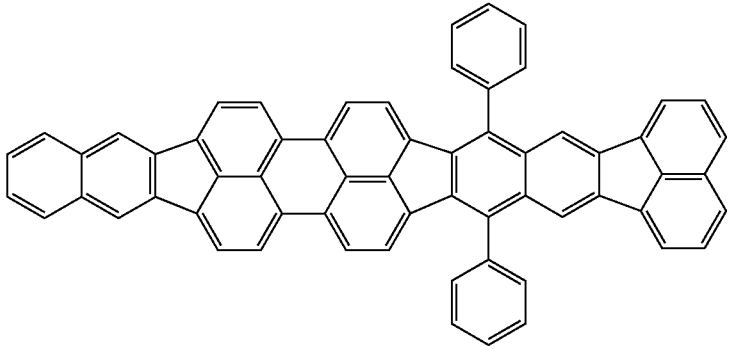 [SMILES: c1ccc(-c2c3cc4c(cc3c(-c3ccccc3)c3c5ccc6c7ccc8c9c(ccc(c%10ccc(c23)c5c%106)c97)-c2cc3ccccc3cc2-8)c2cccc3cccc4c32)cc1] | 603 |

As shown in Table 4, the maximum emission wavelengths of comparative compounds (3) and (4) are not in the desired range. By contrast, exemplary compound C2 has a maximum emission wavelength in the desired range and thus exhibits an emission color suitable for red in display standards. The same is true of exemplary compound C1, which is the basic skeleton itself. Thus, the basic skeleton of the present disclosure is capable of emitting red light with high color purity. The chromaticity coordinates of red will be described in detail in EXAMPLES.

(2) The Skeleton has a High Transition Dipole Moment and Thus Provides a High Quantum Yield.

In general, as the molecular weight of the basic skeleton increases, the sublimation temperature increases toward the decomposition temperature, thus increasing the likelihood of decomposition. To prevent this, it was necessary to achieve a longer emission wavelength with a minimum increase in molecular weight. One parameter of light emission efficiency is oscillator strength. To achieve high light emission efficiency, high oscillator strength is required. Therefore, it was necessary to increase the number of condensed rings in order to achieve a longer emission wavelength by extending the conjugation of the basic skeleton, but the present inventors focused on the position of condensed-ring extension.

Comparative compounds a to c and exemplary compound C2 of the present disclosure were compared with each other in terms of the S1 (singlet excited state) wavelength and the oscillator strength by using molecular orbital calculations. The results are shown in Table 5. The S1 wavelengths of comparative compounds (3) and (4) were 580 nm and 576 nm, respectively, and the oscillator strengths of comparative compounds (3) and (4) were 1.3. Accordingly, S1 wavelengths of 580 nm or more were evaluated as good, and S1 wavelengths of less than 580 nm as poor. Oscillator strengths of 1.3 or more were evaluated as good, and oscillator strengths of less than 1.3 as poor.

TABLE 5

| Compound | Molecular structure | S1 | Oscillator strength | Decomposition during sublimation purification |
|---|---|---|---|---|
| a | 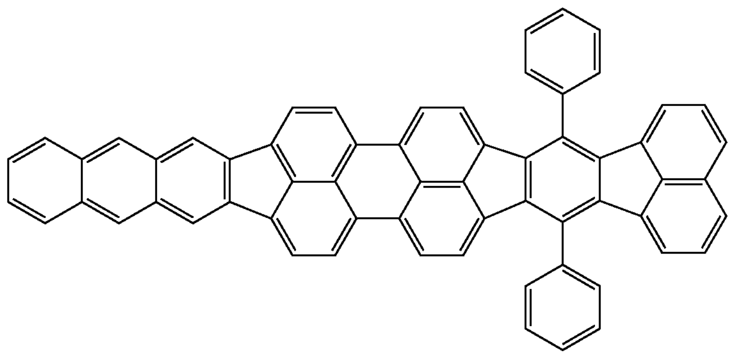 [SMILES: c1ccc(-c2c3c4cccc5cccc(c3c(-c3ccccc3)c3c6ccc7c8ccc9c%10c(ccc(c%11ccc(c23)c6c%117)c%108)-c2cc3cc6ccccc6cc3cc2-9)c54)cc1] | Good | Good | Occurred |
| b | 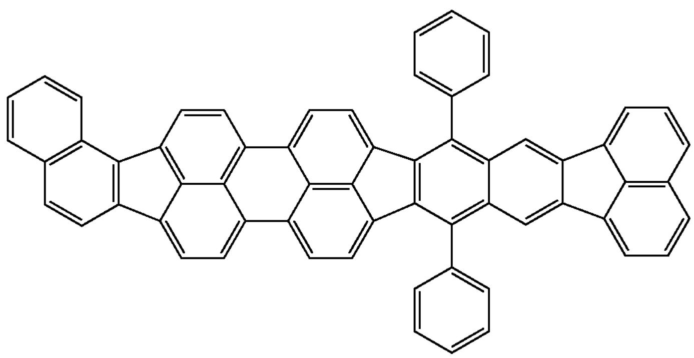 [SMILES: c1ccc(-c2c3cc4c(cc3c(-c3ccccc3)c3c5ccc6c7ccc8c9c(ccc(c%10ccc(c23)c5c%106)c97)-c2ccc3ccccc3c2-8)c2cccc3cccc4c32)cc1] | Good | Poor | — |
| c | 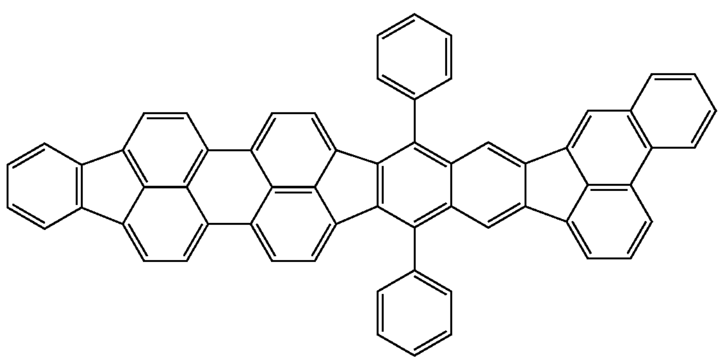 [SMILES: c1ccc(-c2c3cc4c(cc3c(-c3ccccc3)c3c5ccc6c7ccc8c9c(ccc(c%10ccc(c23)c5c%106)c97)-c2ccccc2-8)c2cc3ccccc3c3cccc4c32)cc1] | Poor | Good | — |
| Exemplary compound C2 | 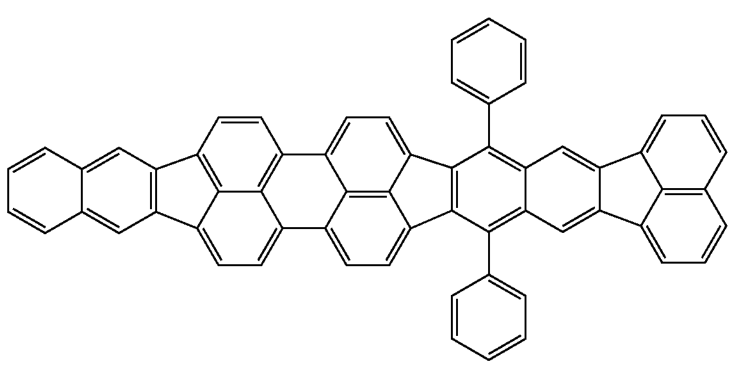 [SMILES: c1ccc(-c2c3cc4c(cc3c(-c3ccccc3)c3c5ccc6c7ccc8c9c(ccc(c%10ccc(c23)c5c%106)c97)-c2cc3ccccc3cc2-8)c2cccc3cccc4c32)cc1] | Good | Good | Not occurred |

Table 5 shows that, as in exemplary compound C2 and comparative compound a, condensation of benzene in a direction in which the molecule is longest relative to the molecular axis effectively achieves a longer wavelength and increases the oscillator strength which influences quantum yields. This is probably due to the following: the skeleton of the present disclosure has a transition dipole moment in the direction in which the molecule is longest relative to the molecular axis, and condensation of benzene in this direction effectively increases the transition dipole moment.

(3) The Organic Compound does not have Highly Reactive SP² Carbon and Thus has High Thermal Stability.

Comparative compound a and exemplary compound C2, each satisfying the S1 wavelength and the oscillator strength, were synthesized and subjected to sublimation purification. Comparative compound a partially decomposed after the sublimation purification, whereas exemplary compound C2 did not decompose, as shown in Table 5. The occurrence of decomposition was determined by liquid chromatography analysis. This result shows that comparative compound a has low thermal stability, which is because comparative compound a has highly reactive SP² carbon in the anthracene structure contained in the basic skeleton. By contrast, exemplary compound C2 of the present disclosure does not have highly reactive SP² carbon in the basic skeleton and thus has high thermal stability. Stable sublimation purification that does not cause decomposition enables an increase in purity of a material and the production of an organic light-emitting element through vapor deposition. This can decrease the amount of impurities contained in an organic electroluminescent element, thus reducing the occurrence of a decrease in light emission efficiency due to impurities and a decrease in driving durability.

Accordingly, the compound according to the present disclosure is a disclosure that achieves a longer emission wavelength, high efficiency, and sublimation stability. Using the compound in an organic electroluminescent element provides high color purity, highly efficient red-light-emitting properties, and high driving durability. Furthermore, when the compound is used, for example, as a display, deep red can be reproduced.

Hereinafter, features of further aspects of the compound according to the present disclosure will be described.

(4) The organic compound has a group other than hydrogen at any of $R_7$, $R_8$, $R_{13}$, $R_{18}$, $R_{23}$, and $R_{24}$.

(5) The organic compound has a group that covers the molecular plane.

These features will be described below.

(4) The Organic Compound has a Group Other than Hydrogen at any of $R_7$, $R_8$, $R_{13}$, $R_{18}$, $R_{23}$, and $R_{24}$.

When the organic compound according to one embodiment of the present disclosure has a group other than hydrogen at $R_1$ to $R_{24}$, crystallinity of the molecule itself due to intermolecular stacking can be reduced to some degree. Reducing crystallinity leads to reduced intermolecular concentration quenching and improved sublimability. The organic compound according to the present disclosure has high planarity due to the longer wavelength, and if $R_1$ to $R_{24}$ are each a hydrogen atom, intermolecular stacking readily occurs. Thus, substitution positions that can effectively reduce intermolecular stacking will be described.

Table 6 shows dihedral angles between phenyl groups at positions $R_1$ to $R_{24}$ and the basic skeleton, that is, the degree of twist of the phenyl groups relative to the basic skeleton. At substitution positions $R_7$, $R_8$, $R_{13}$, $R_{18}$, $R_{23}$, and $R_{24}$, the steric repulsion between hydrogen at an ortho position of the phenyl group and hydrogen of the basic skeleton is large, and thus the dihedral angle is large. Therefore, the planarity of the whole molecule is lost. This effect prevents intermolecular stacking and reduces crystallinity, leading to reduced intermolecular concentration quenching and improved sublimability.

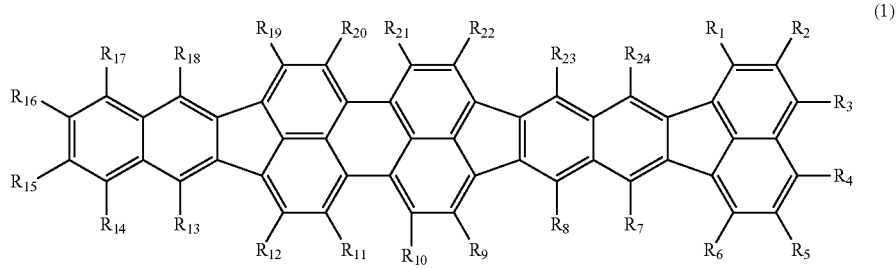

(1)

TABLE 6

| Substitution position | | | | | | | | | | | | |
|---|---|---|---|---|---|---|---|---|---|---|---|
| $R_1$ $R_6$ | $R_2$ $R_5$ | $R_3$ $R_4$ | $R_{15}$ $R_{16}$ | $R_{14}$ $R_{17}$ | $R_{13}$ $R_{18}$ | $R_{12}$ $R_{19}$ | $R_{11}$ $R_{20}$ | $R_{10}$ $R_{21}$ | $R_9$ $R_{22}$ | $R_8$ $R_{23}$ | $R_7$ $R_{24}$ |
| Dihedral angle/° 56 | 40 | 49 | 17 | 57 | 90 | 55 | 68 | 68 | 57 | 90 | 90 |

Therefore, a group other than hydrogen, preferably, a bulky group or a group having a bulky substituent may be introduced at at least one selected from $R_7$, $R_8$, $R_{13}$, $R_{18}$, $R_{23}$, and $R_{24}$, preferably, at either $R_7$ or $R_8$ and either $R_{23}$ or $R_{24}$. The group other than hydrogen is a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aryl group having 6 to 18 carbon atoms, a substituted or unsubstituted heterocyclic group having 3 to 15 carbon atoms, a substituted or unsubstituted aryloxy group, a silyl group, or a cyano group, preferably, a substituted or unsubstituted alkyl group having 1 to 10 carbon atoms or a substituted or unsubstituted aryl group having 6 to 18 carbon atoms.

(5) The Organic Compound has a Group that Covers the Molecular Plane.

Specifically, when the group other than hydrogen is an alkyl group having 1 to 10 carbon atoms, for example, methyl, ethyl, propyl, butyl, hexyl, and octyl are preferred, and isopropyl and tertiary butyl, which are sterically large, are particularly preferred. When the group other than hydrogen is an aryl group having 6 to 18 carbon atoms, aryl groups such as phenyl and naphthyl are preferred, phenyl, which has a low molecular weight, is preferred from the viewpoint of sublimability, and aryl groups such as phenyl substituted with methyl, isopropyl, or tertiary butyl are preferred. The group other than hydrogen may also be a fluorine atom or an aryl group having a fluorine atom from this viewpoint. The group other than hydrogen may be introduced because when a liquid containing the organic compound is provided (applied) to a predetermined position and then the solvent is removed, a film having improved properties may be formed.

Figure 2:
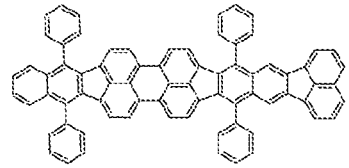
FIG. 2 is a comparison of the molecular structures of an unsubstituted compound, an ortho-tolyl compound, and an ortho-biphenyl compound.

For further improvements, the present inventors attempted to introduce a group that shields the π-conjugated plane. As a result, it has been discovered that as shown in FIG. 2, ortho-substituted aryl groups as in an ortho-tolyl compound having a methyl group at an ortho position of a phenyl group, as introduced as at least one selected from $R_7$, $R_8$, $R_{13}$, $R_{18}$, $R_{23}$, and $R_{24}$, and an ortho-biphenyl compound having a phenyl group at an ortho position of a phenyl group can cover the π-conjugated plane of the basic skeleton to inhibit intermolecular stacking. A phenyl group can more effectively shield the π-conjugated plane to inhibit intermolecular stacking than a methyl group.

Accordingly, when the condition (5) is satisfied, the organic compound according to the present disclosure has a large difference between the sublimation temperature and the thermal decomposition temperature and thus has high sublimability.

Taken together, the organic compound according to the present disclosure has the features (1) to (3) above and thus is an organic compound that has a basic skeleton whose emission wavelength is in the red range and that has maintained sublimability, as compared with the comparative compounds. Furthermore, when having the features (4) and (5), the compound is less likely to undergo intermolecular stacking, has improved sublimability, and is less likely to undergo concentration quenching. Using this compound can provide an organic light-emitting element that has high efficiency and high element durability and that emits red light with high color purity.

Specific examples of the organic compound according to one embodiment of the present disclosure are shown below. However, the present disclosure is not limited to these examples.

A1

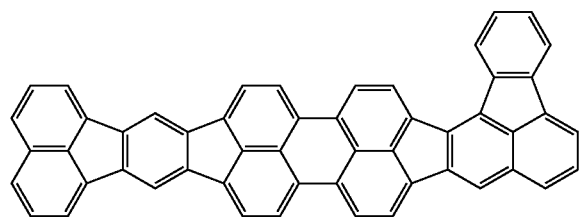

A2

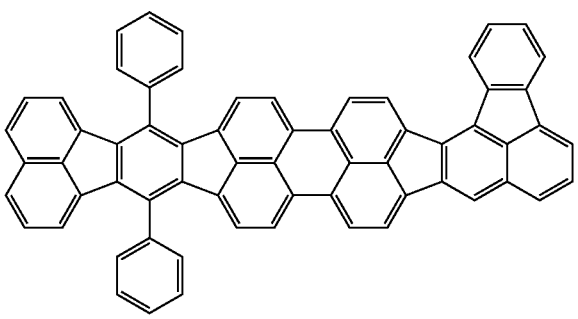

A3

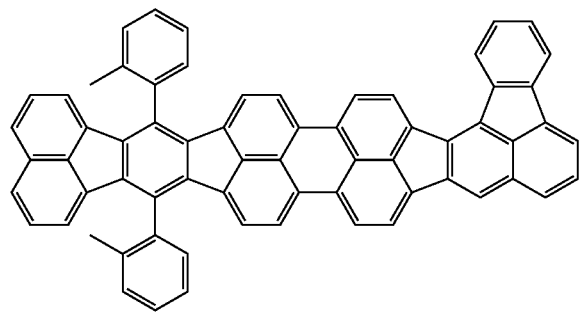

A4

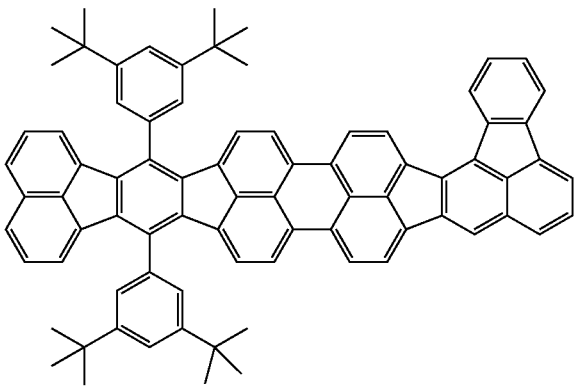

-continued
A5
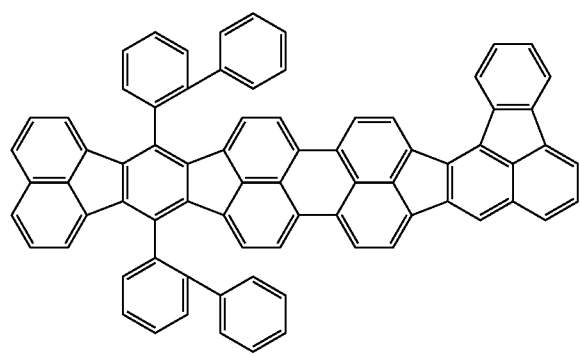
A6
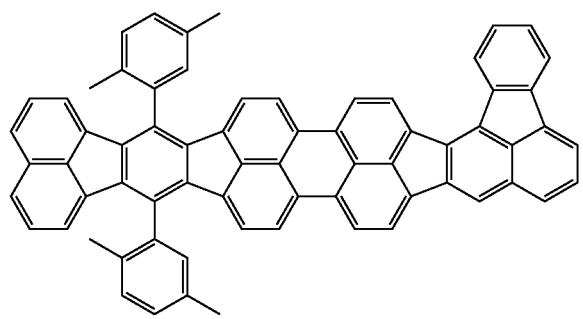
A7
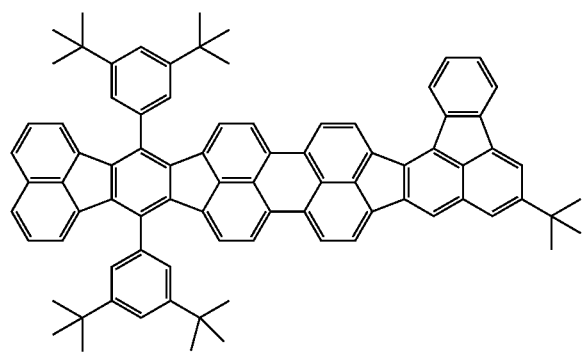
A8
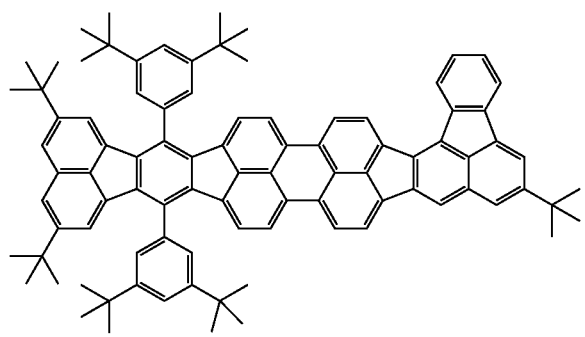
A9
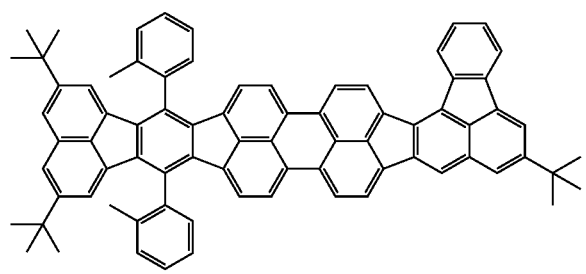
A10
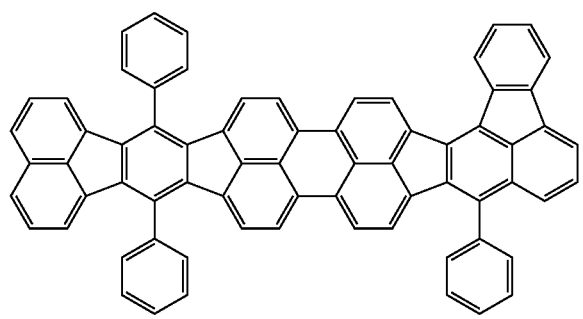
A11
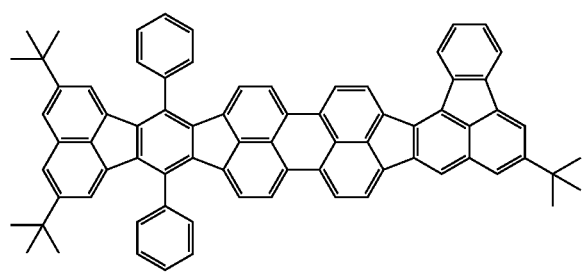
A12
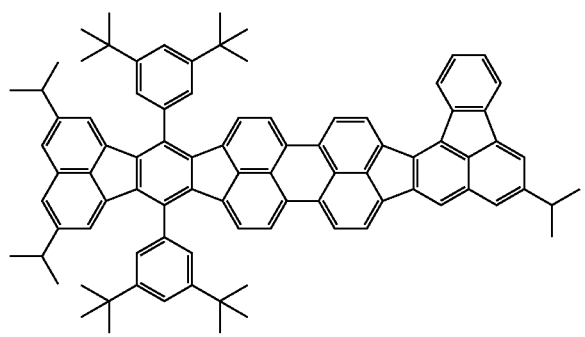

-continued
A13
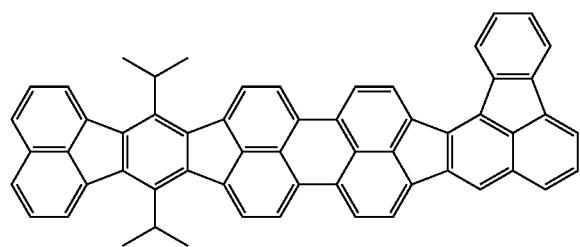
A14
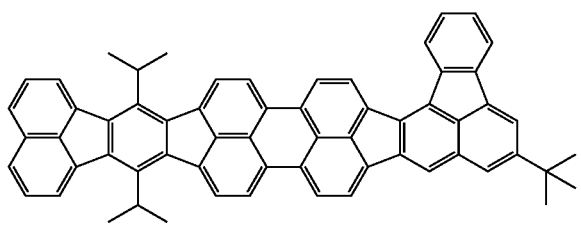
A15
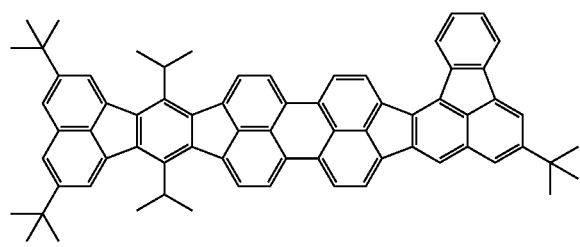
A16
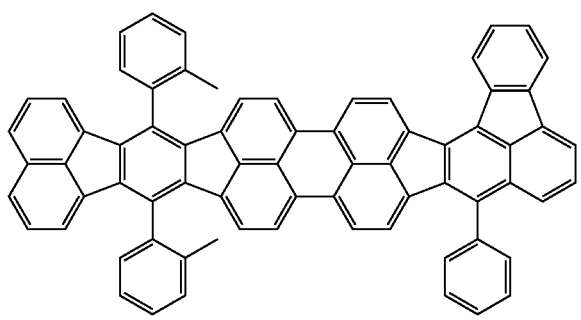
A17
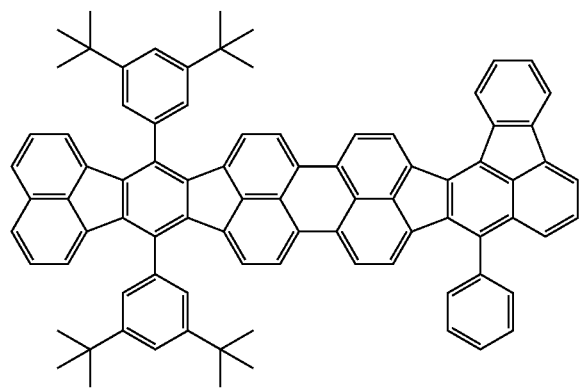
A18
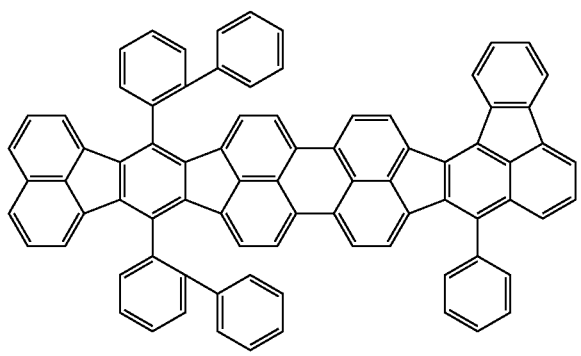
A19
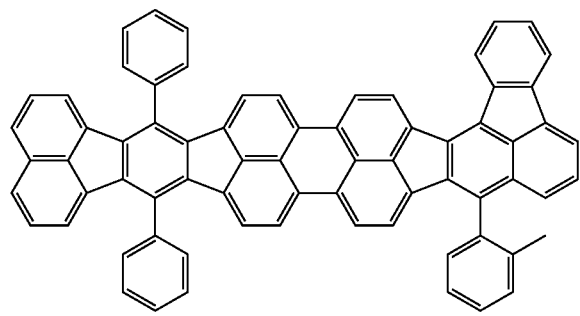
A20
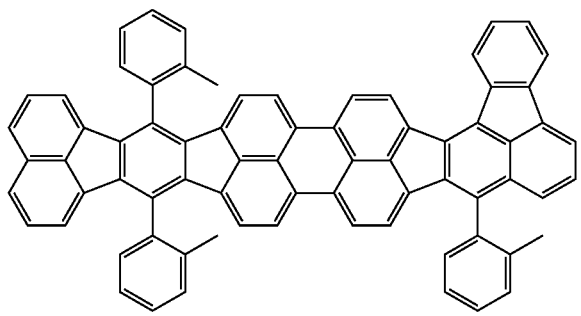

-continued
A21
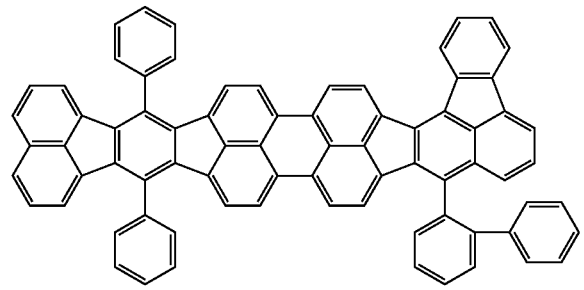
A22
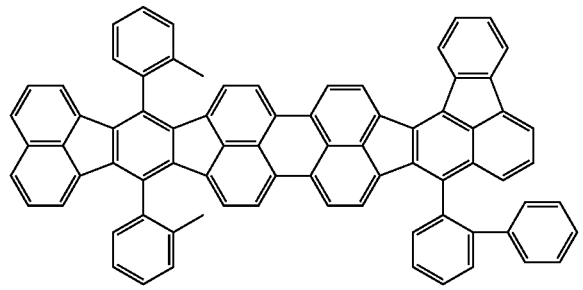
A23
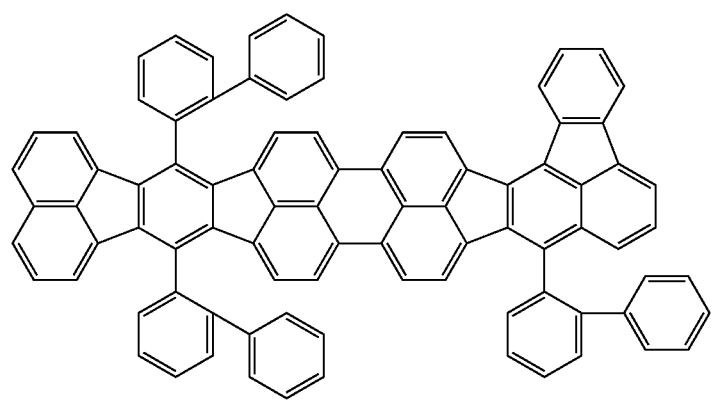
A24
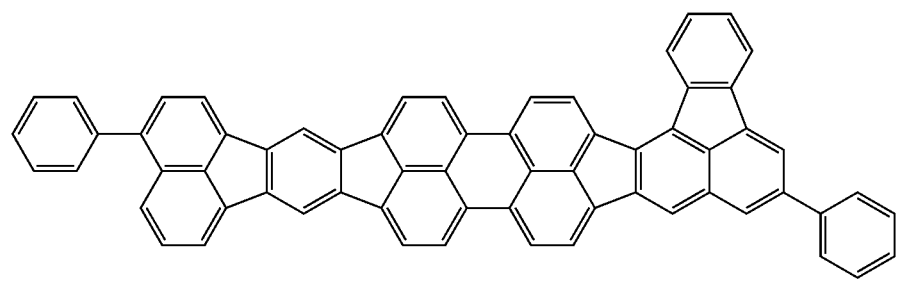
A25
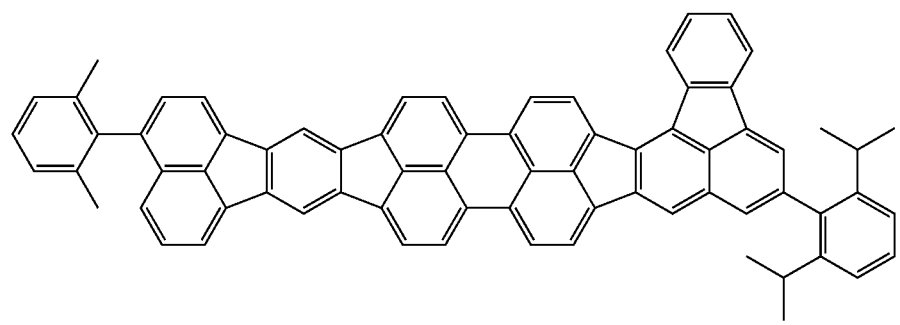
A26
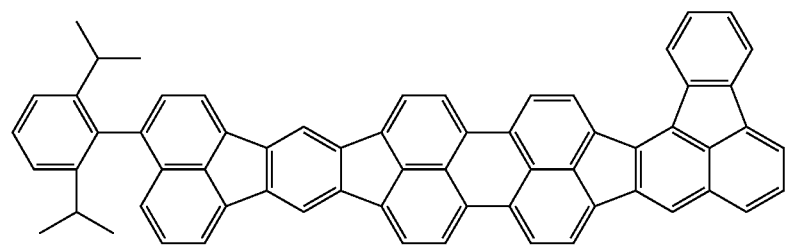

-continued
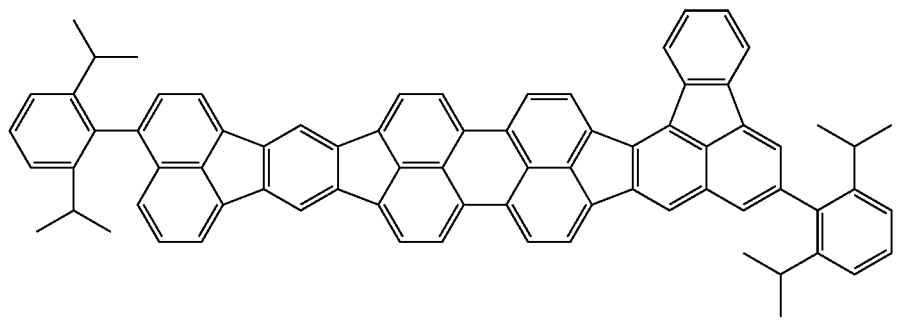
A27
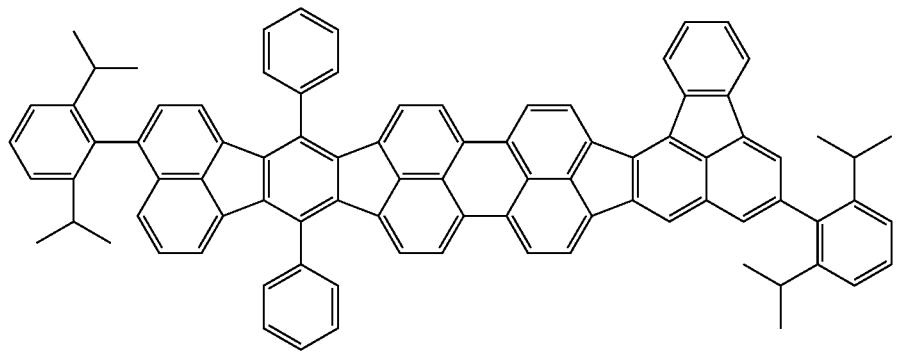
A28
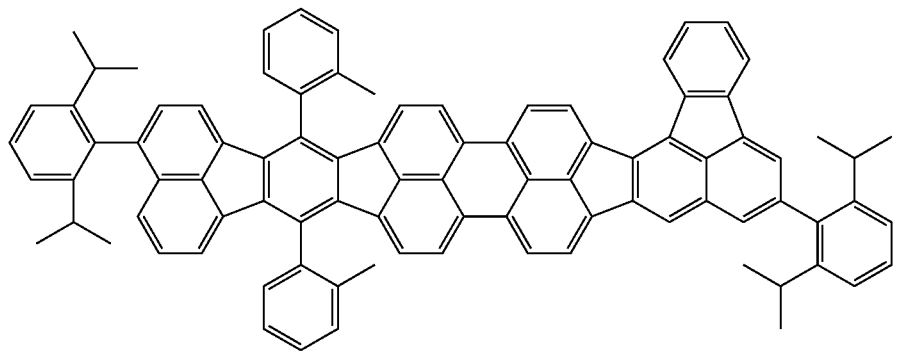
A29
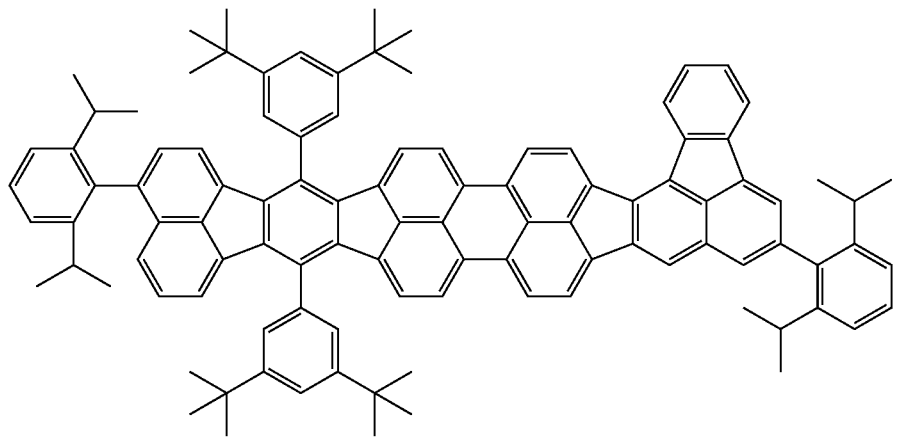
A30

-continued
A31
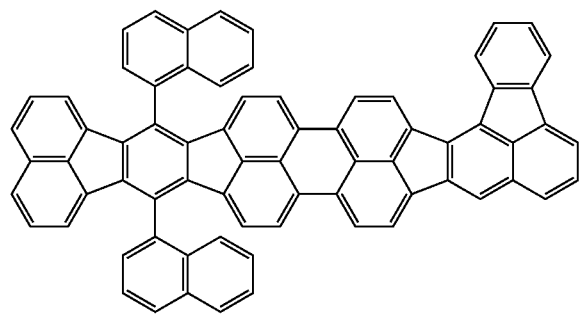
A32
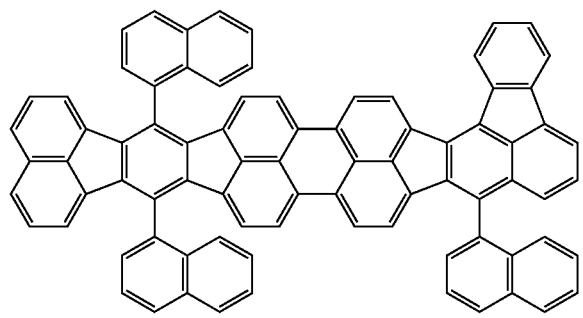
A33
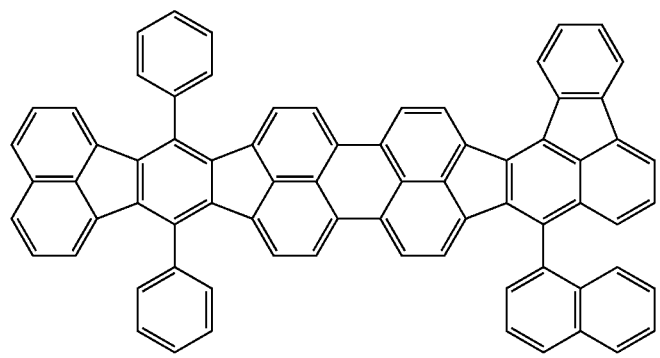
A34
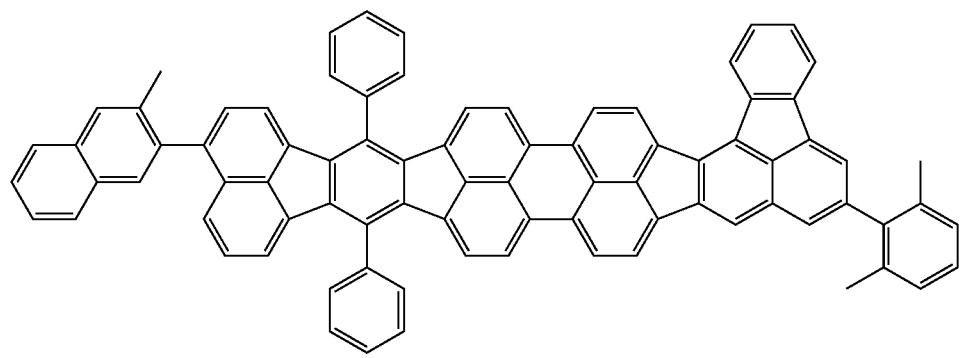
A35
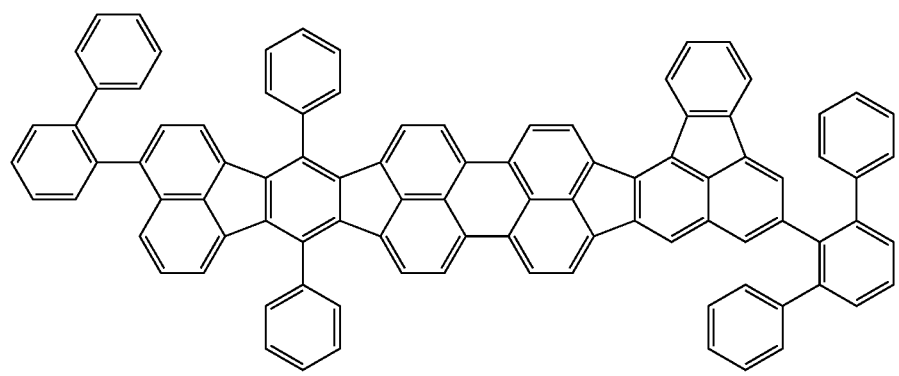

-continued
A36
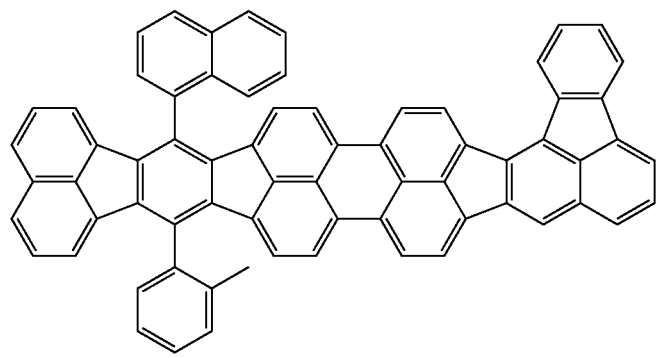
A37
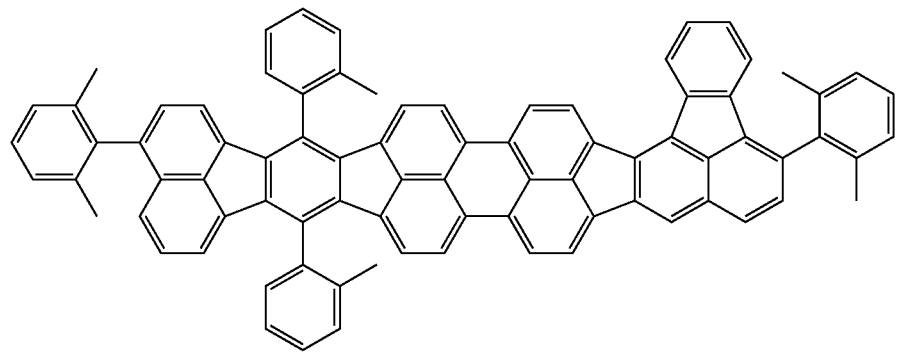
A38
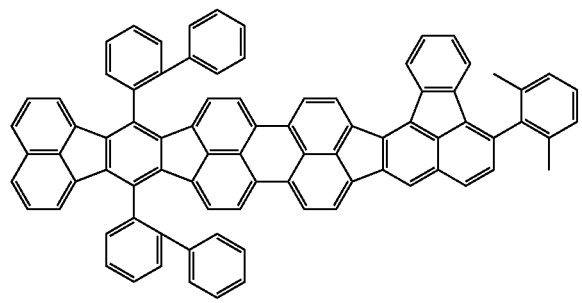
A39
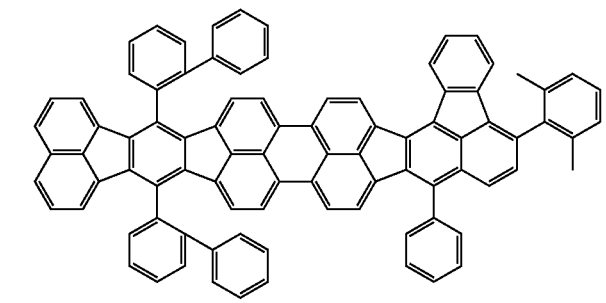
A41
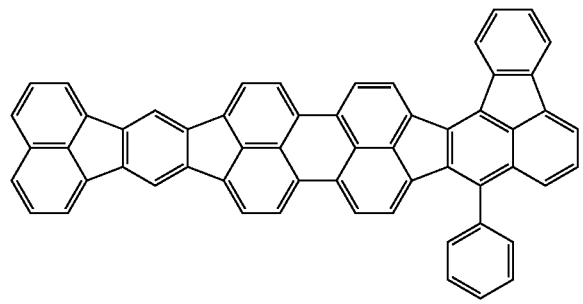
A42
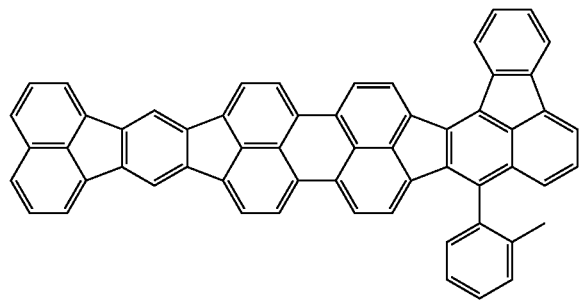

-continued
A43
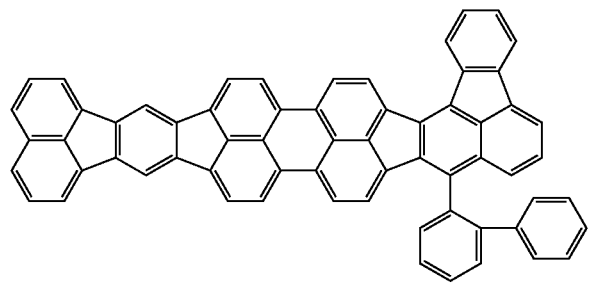
A44
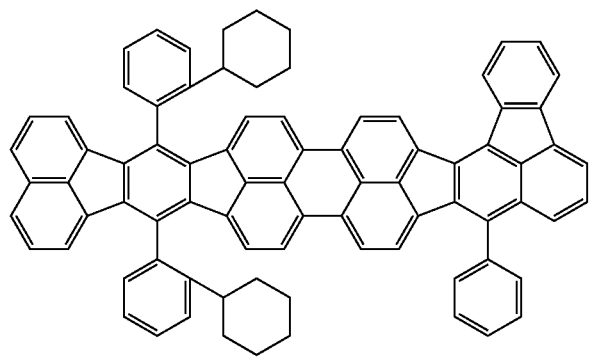
A45
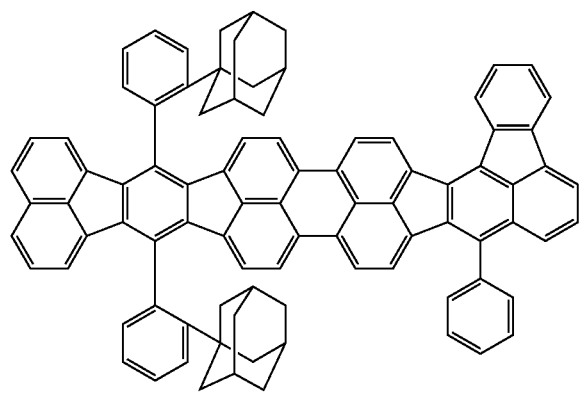
A46
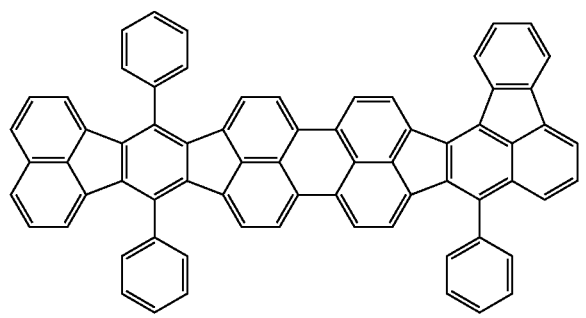
A47
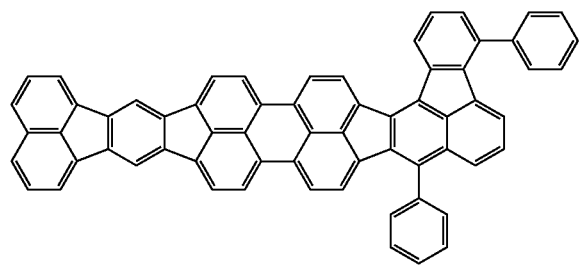
A48
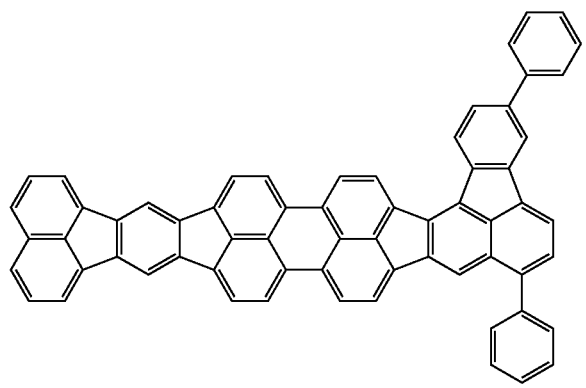
A49
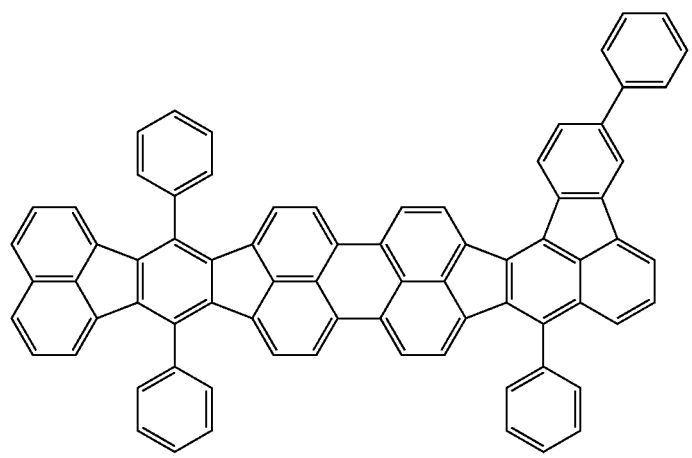

-continued
B1
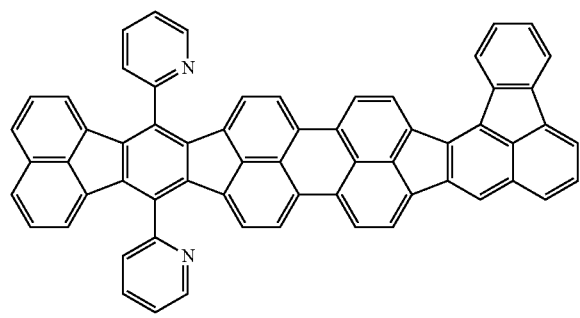
B2
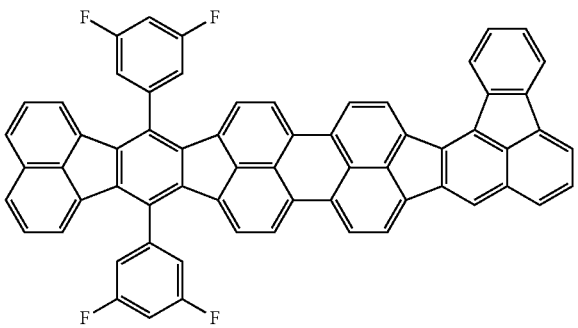
B3
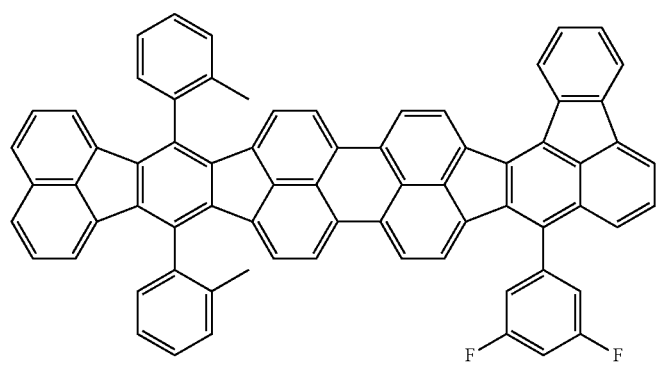
B4
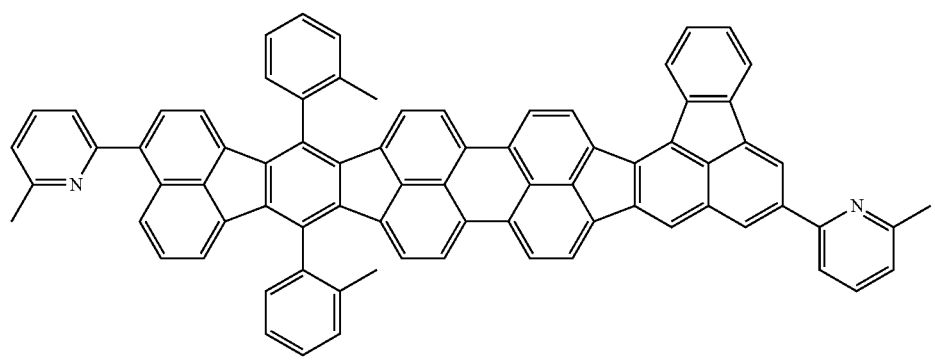
B5
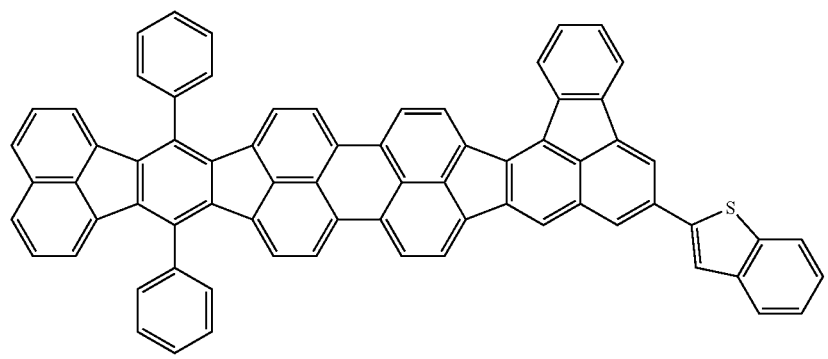

B6
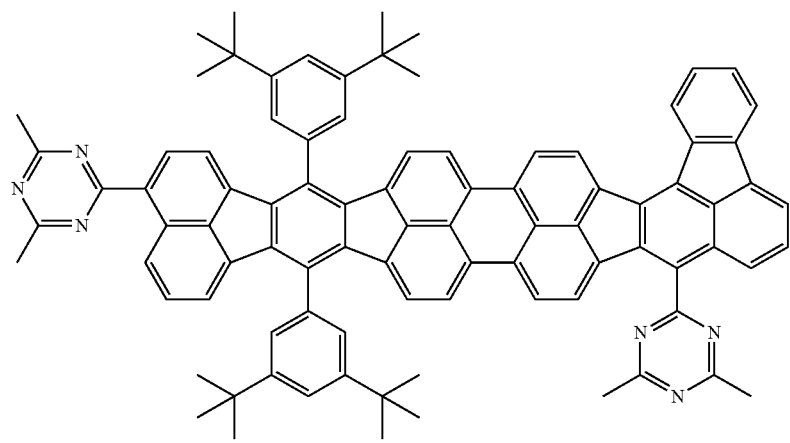
B7
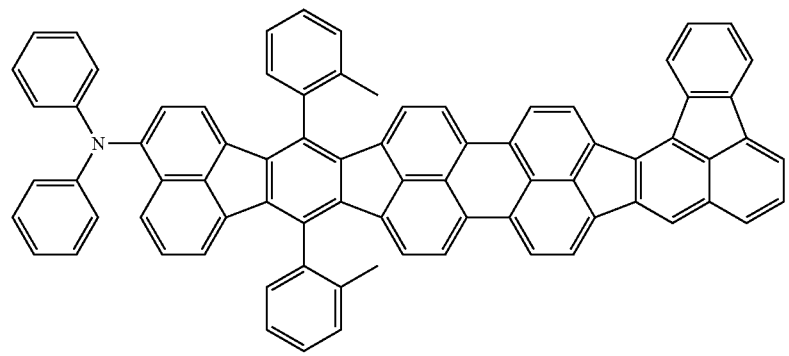
B8
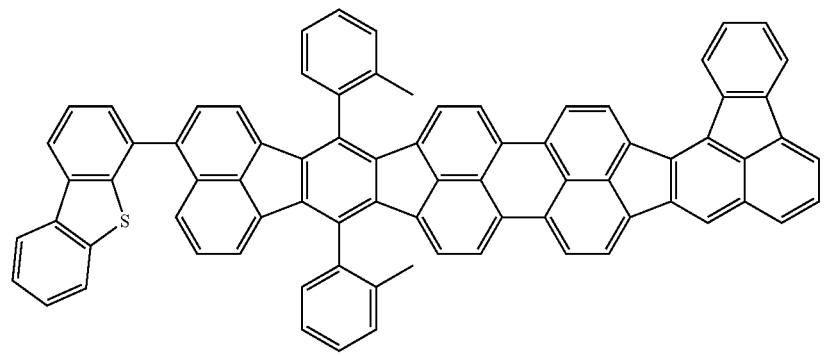
B9
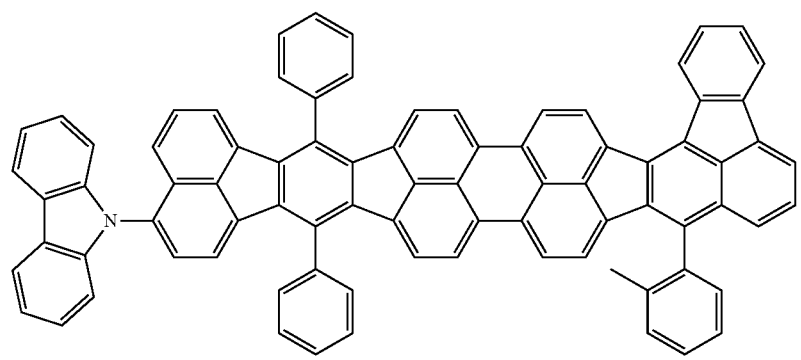

-continued
B10
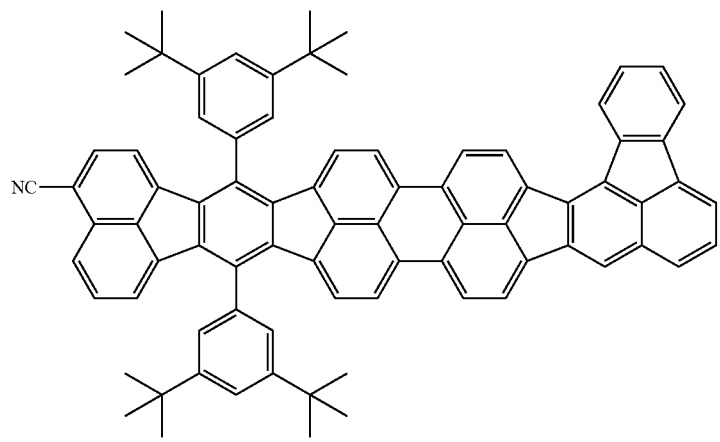
B11
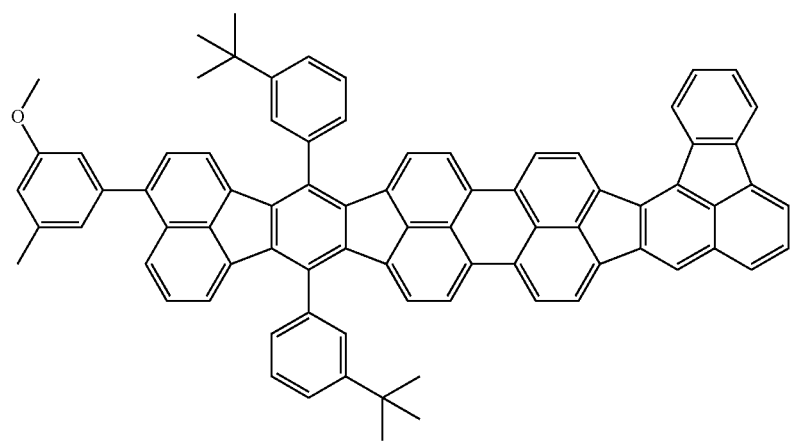
B12
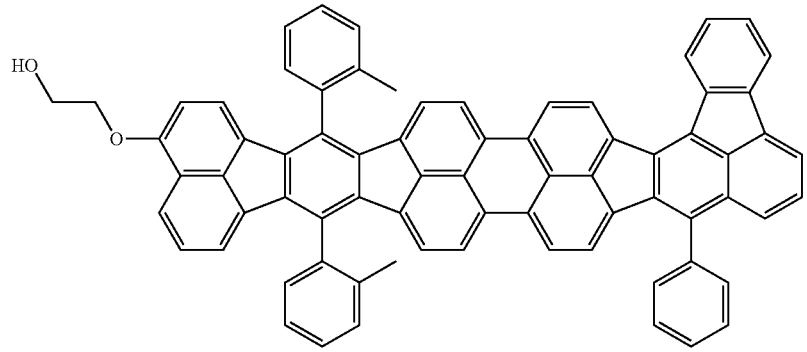
B13
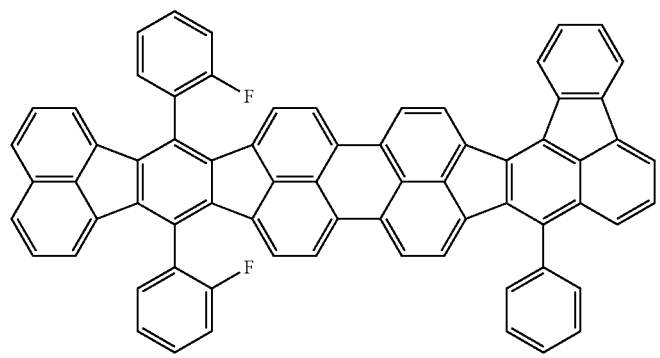

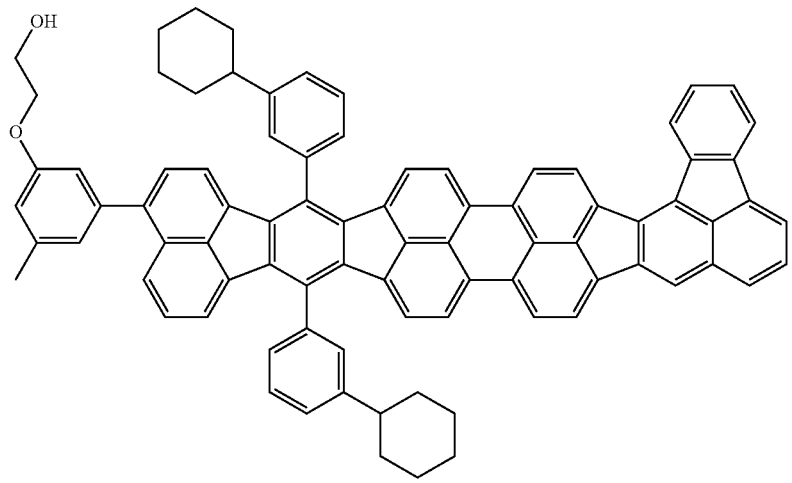
B14
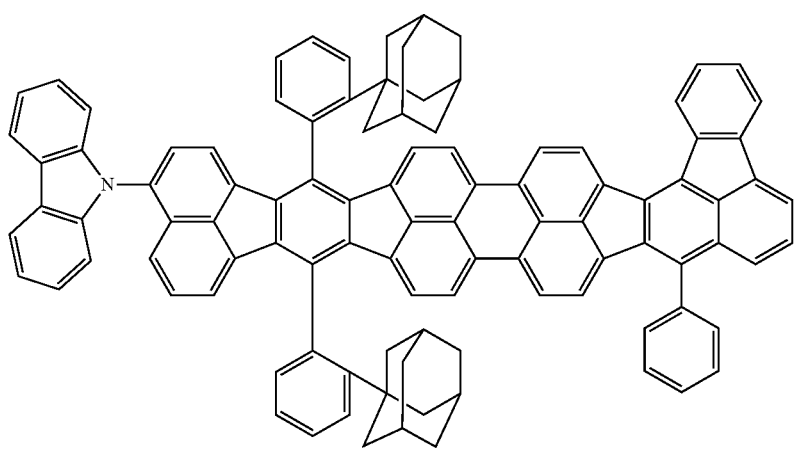
B15
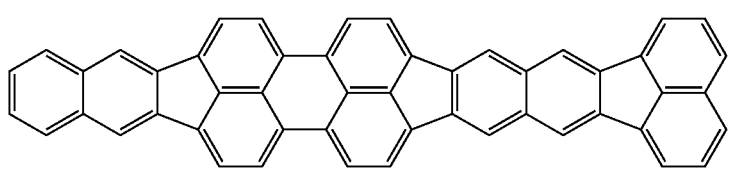
C1
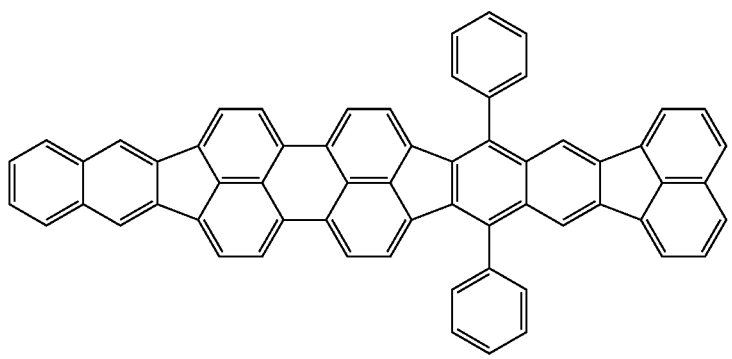
C2

C3
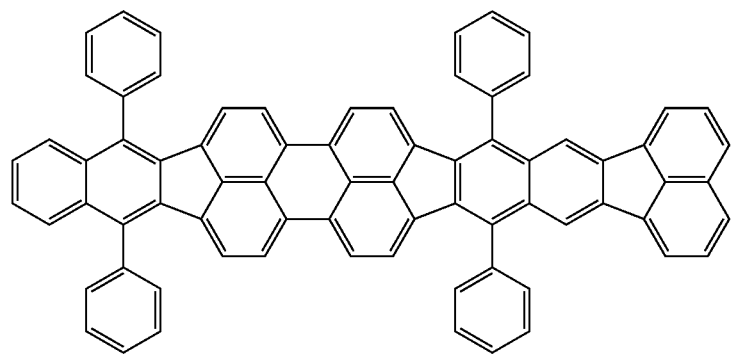
C4
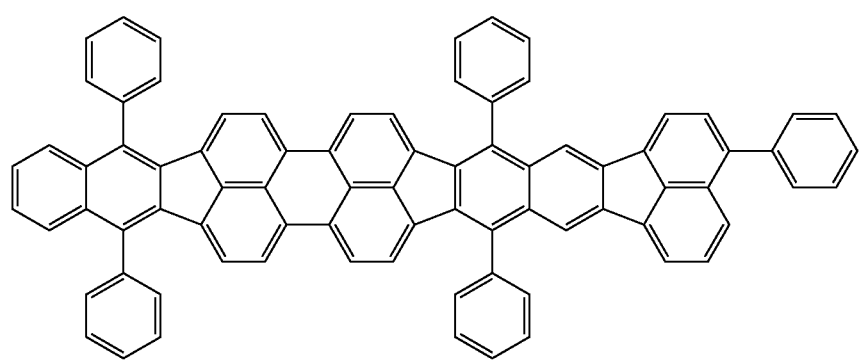
C5
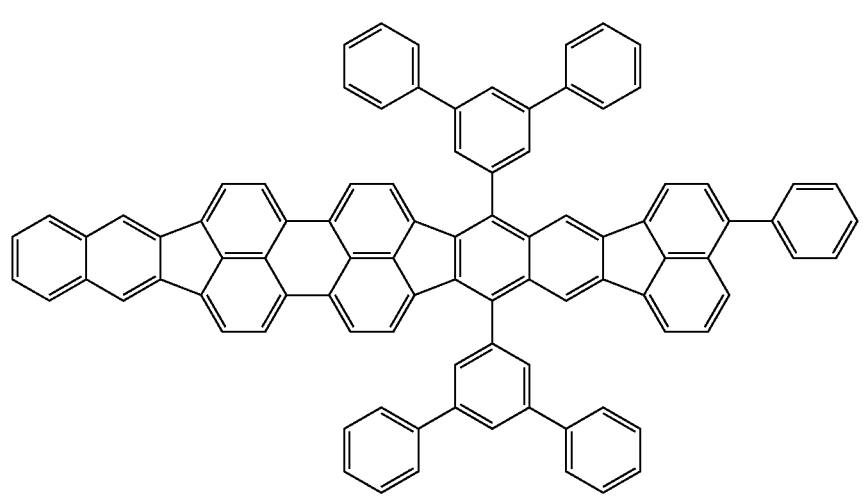
C6
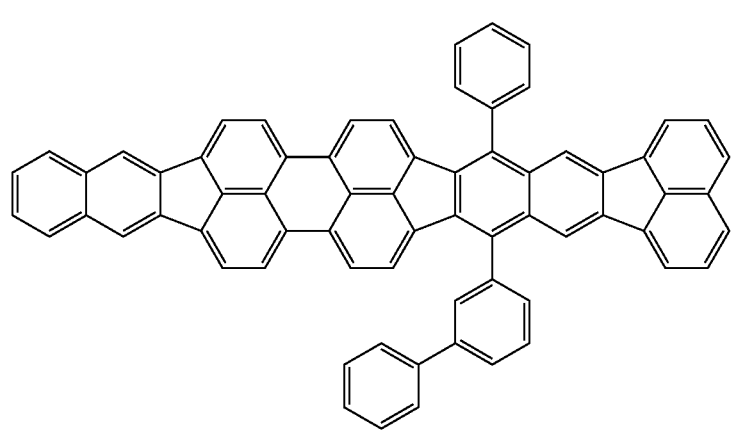

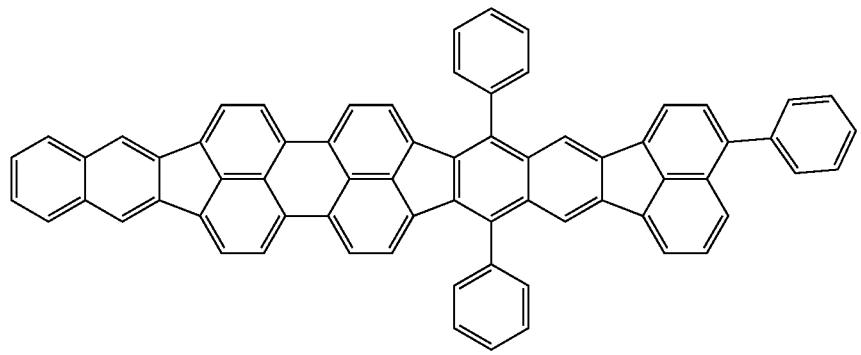
C7
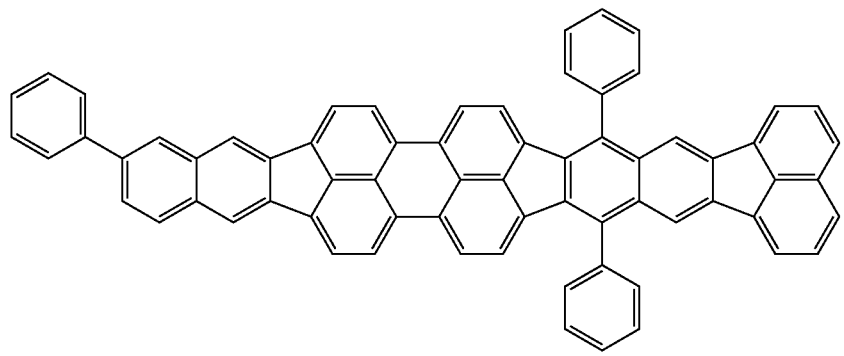
C8
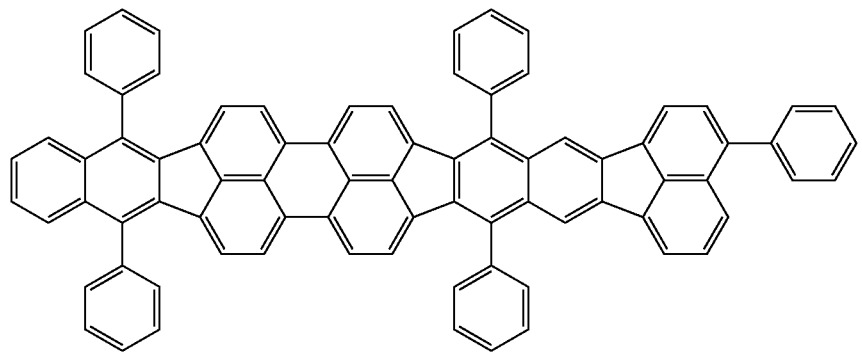
C9
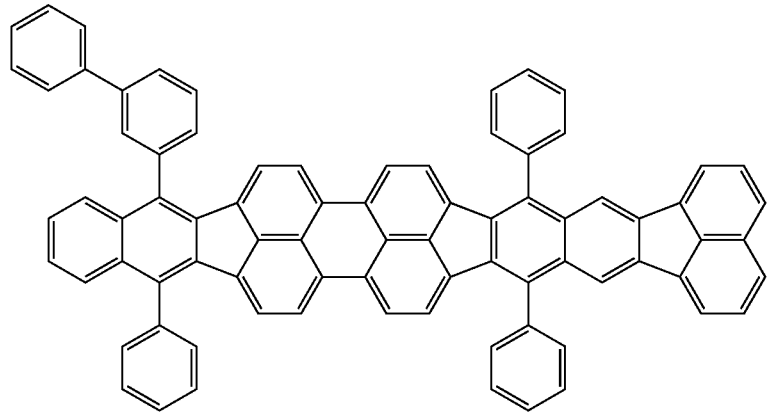
C10

-continued
C11
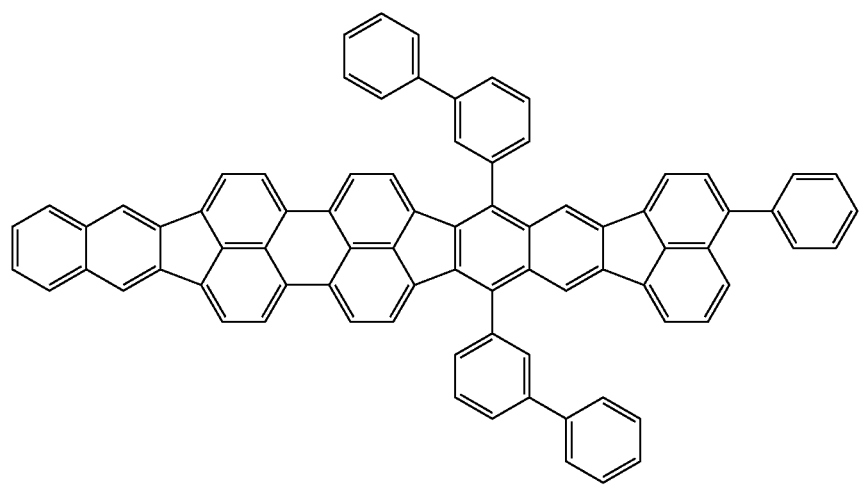
C12
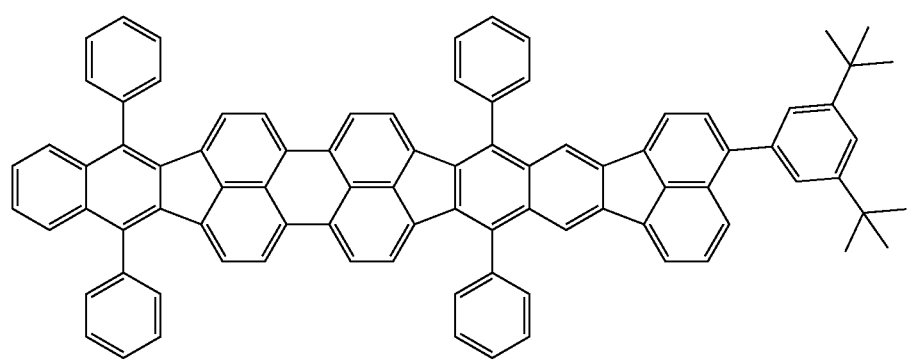
C13
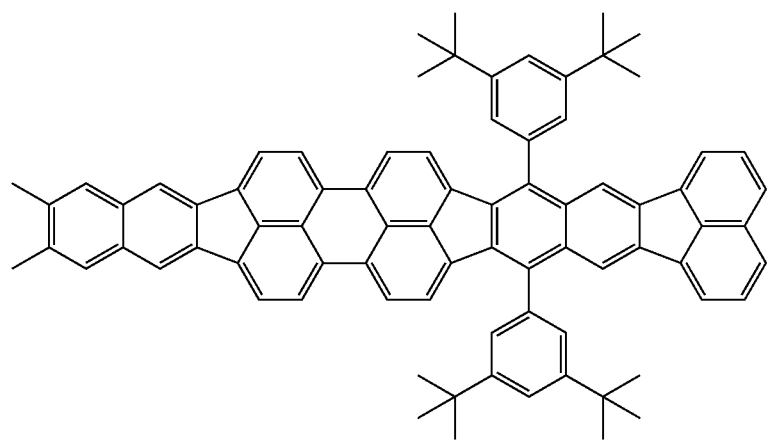

-continued
C14
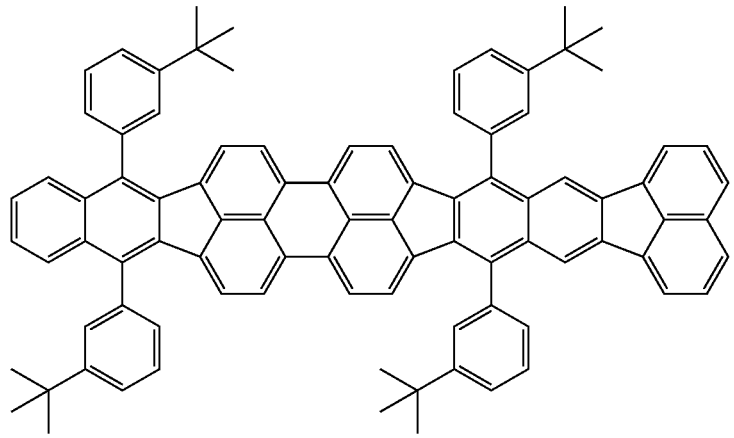
C15
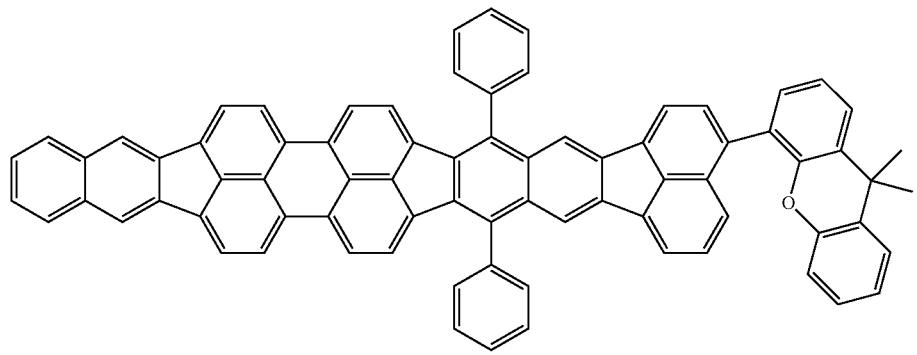
C16
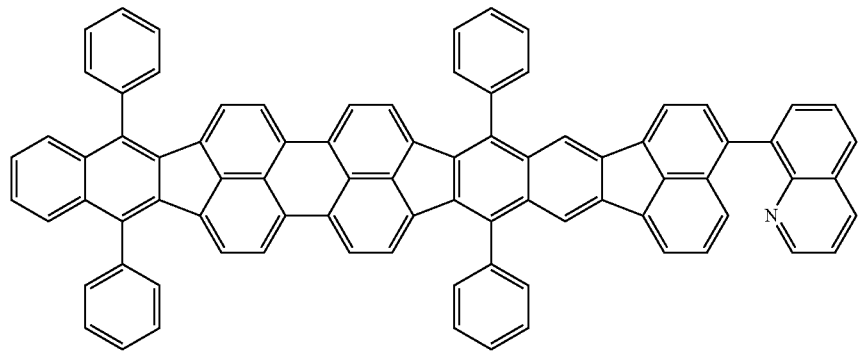
C17
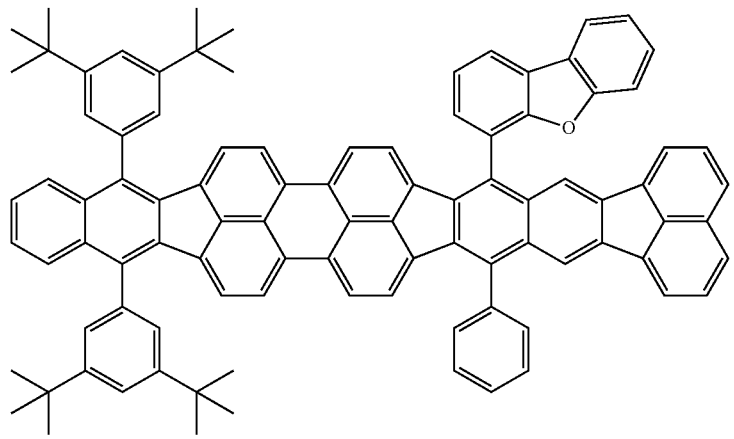

C18
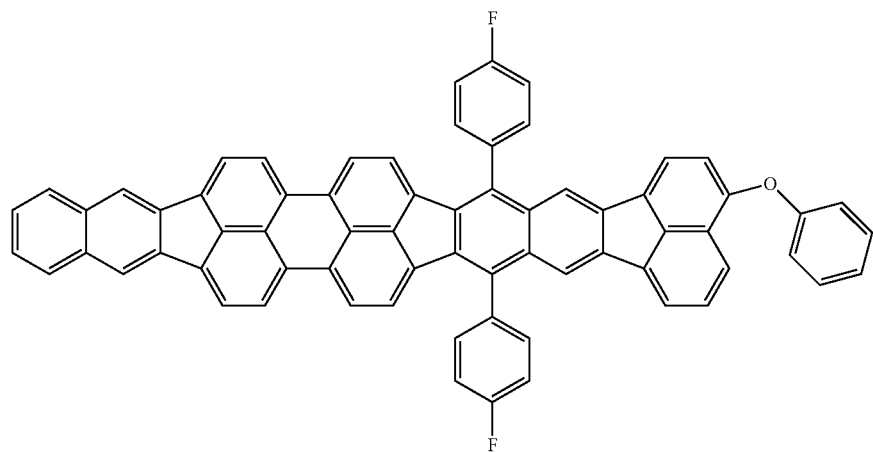
D1
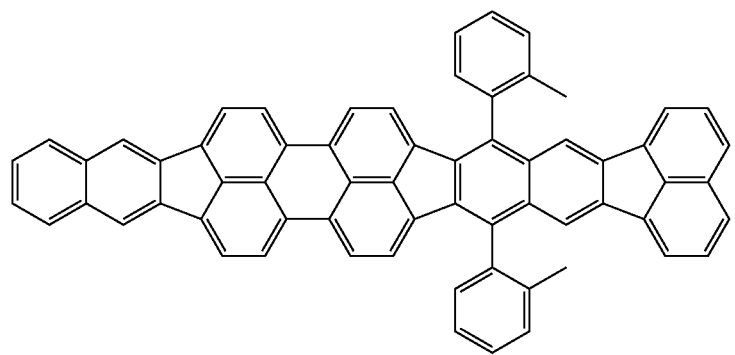
D2
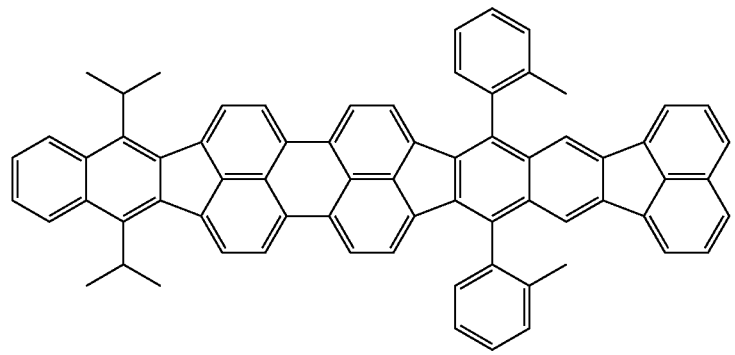
D3
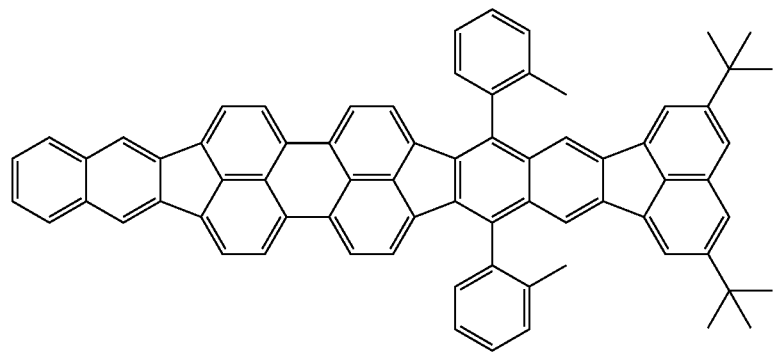

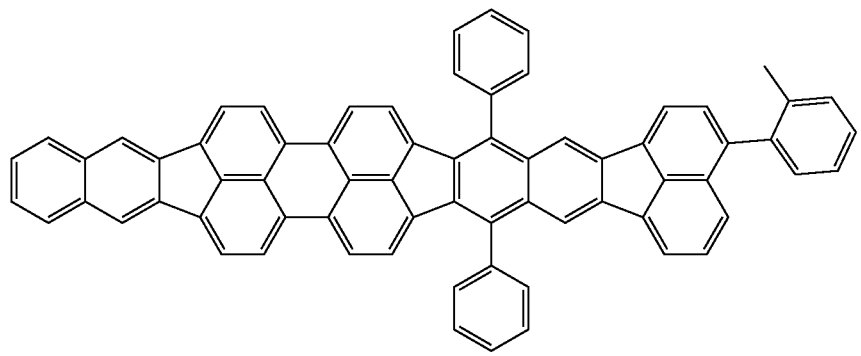
D4
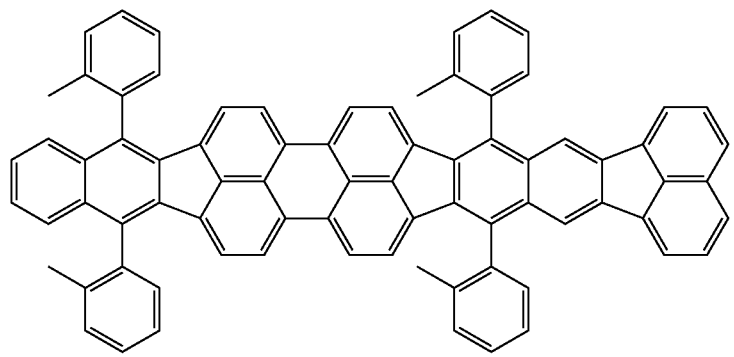
D5
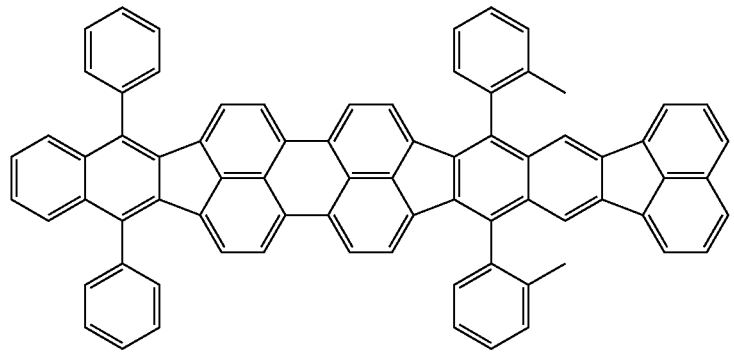
D6
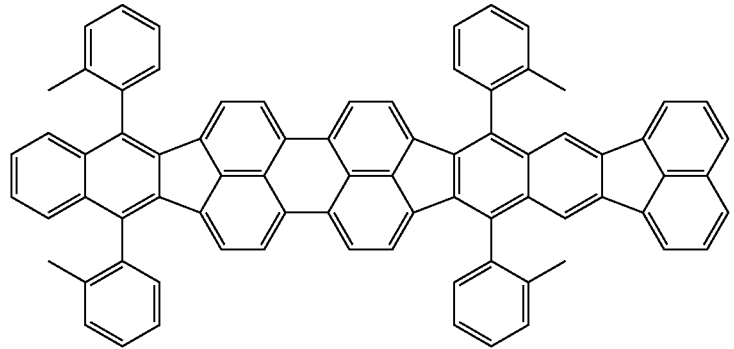
D7

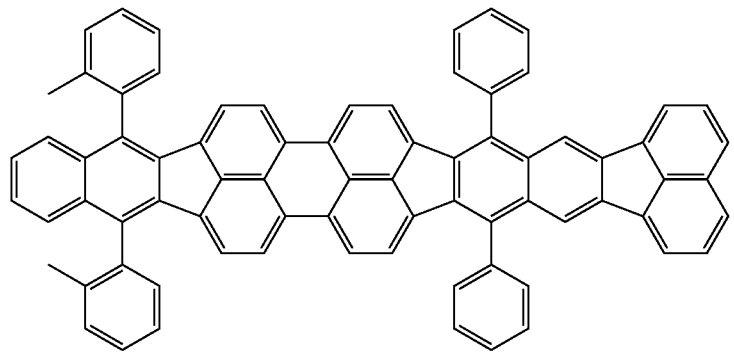
D8
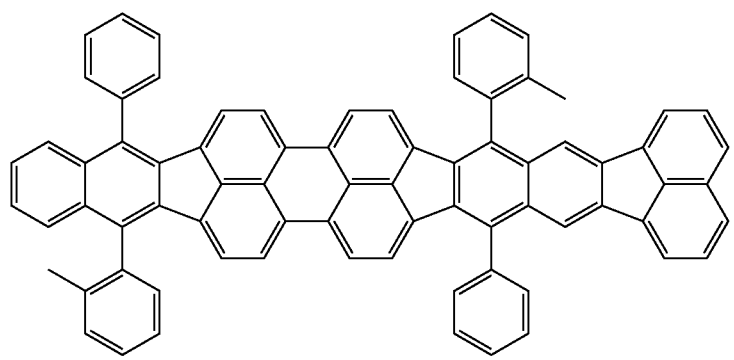
D9
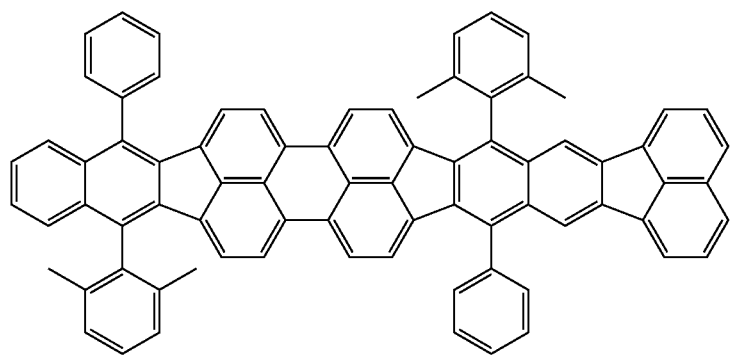
D10
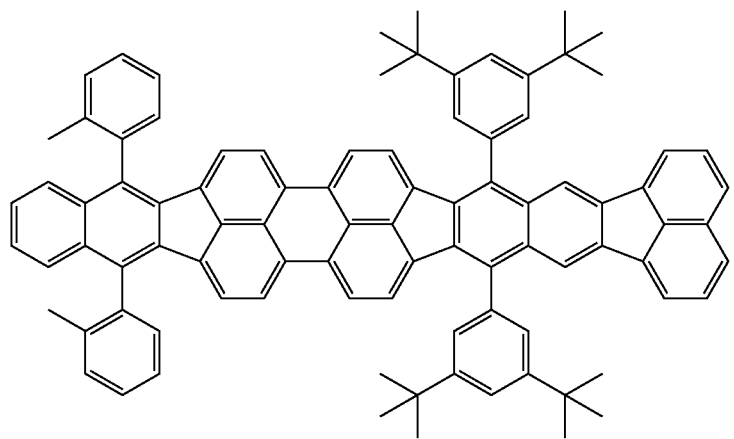
D11

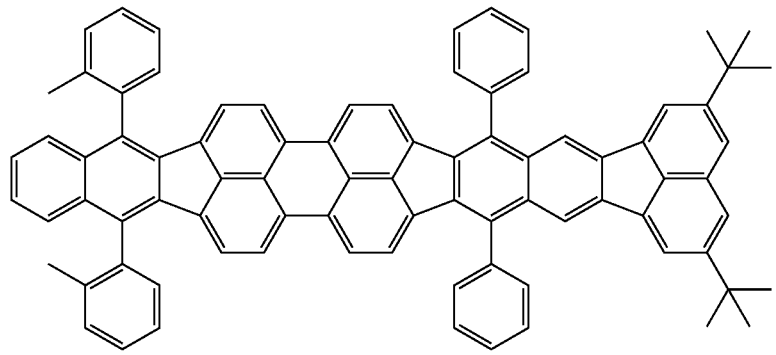
D12
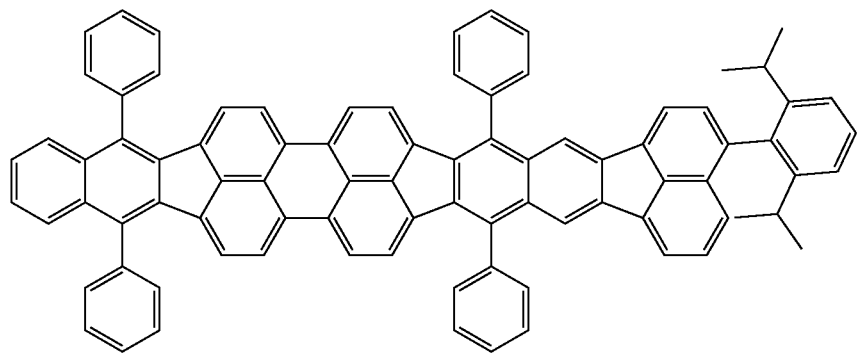
D13
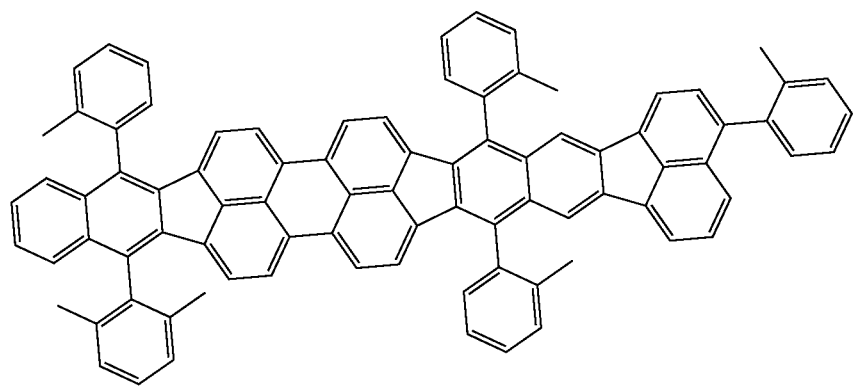
D14
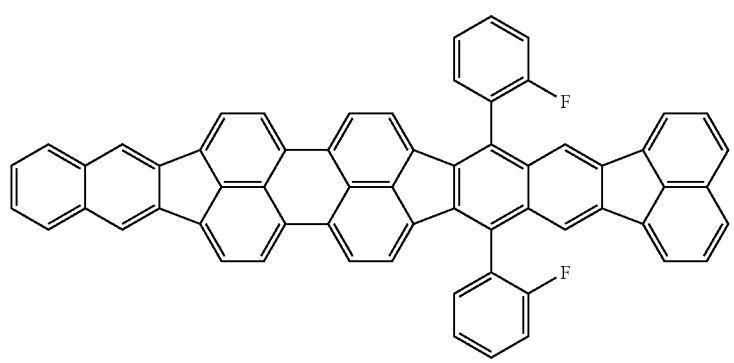
D15

-continued
D16
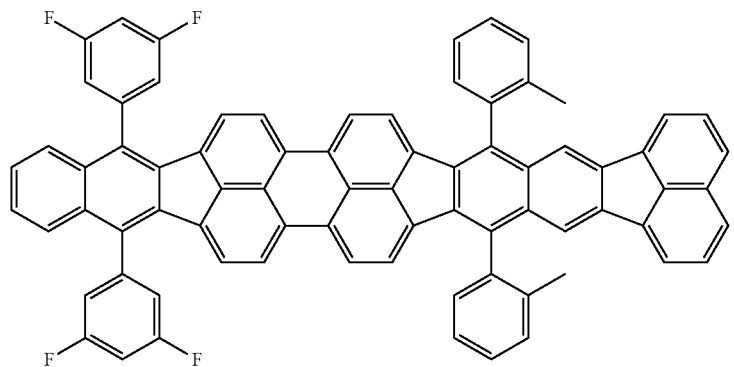
D17
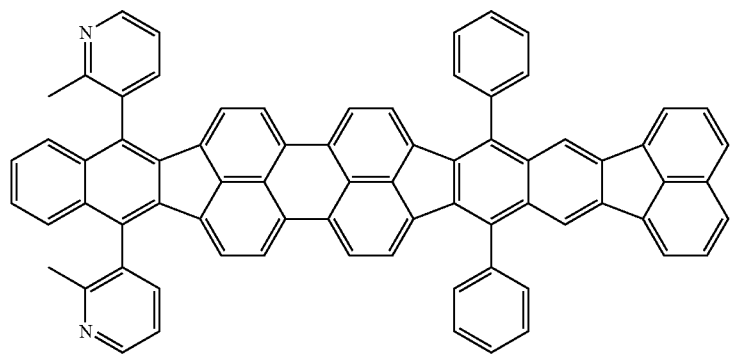
D18
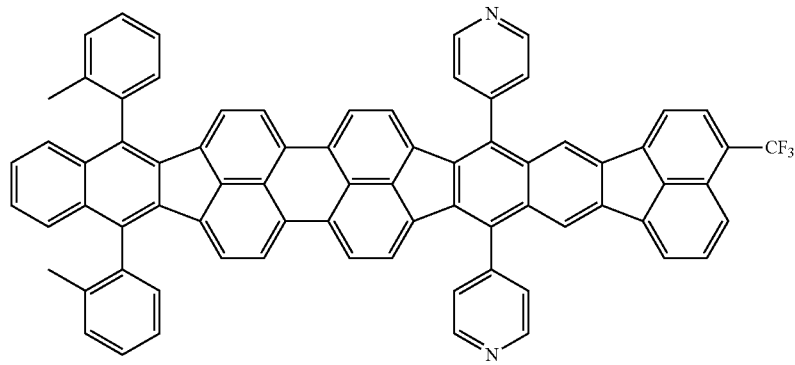
D19
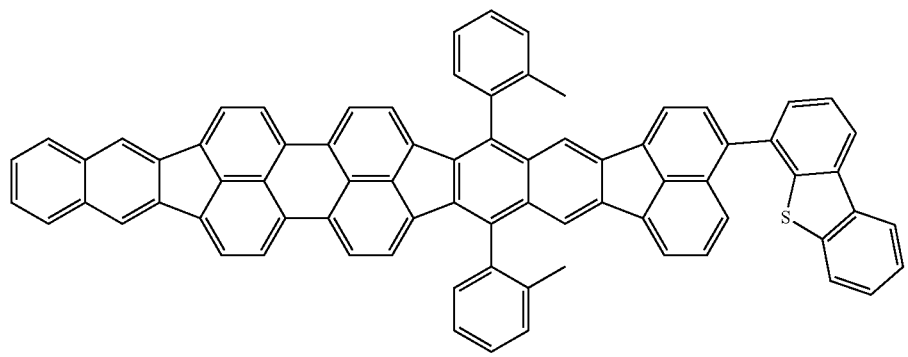

D20
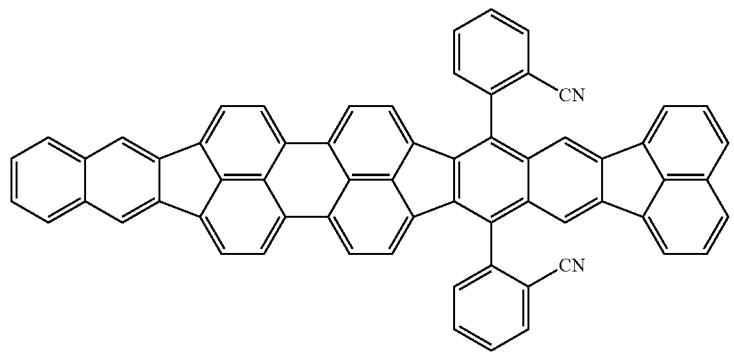
D21
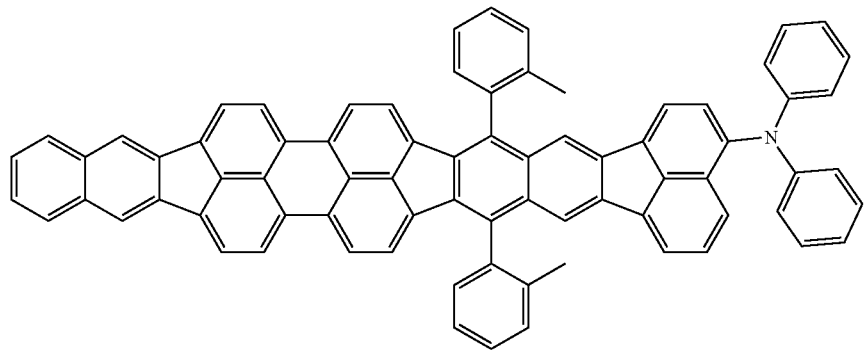
E1
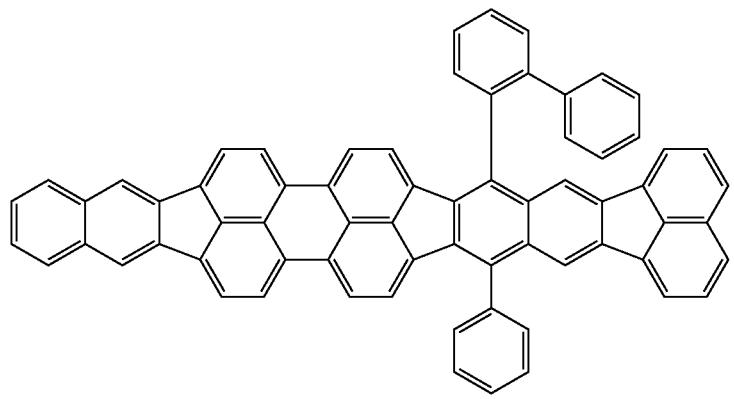
E2
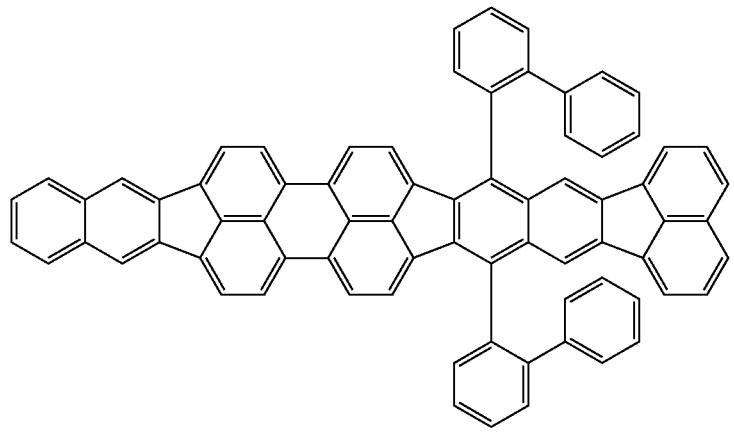

E3
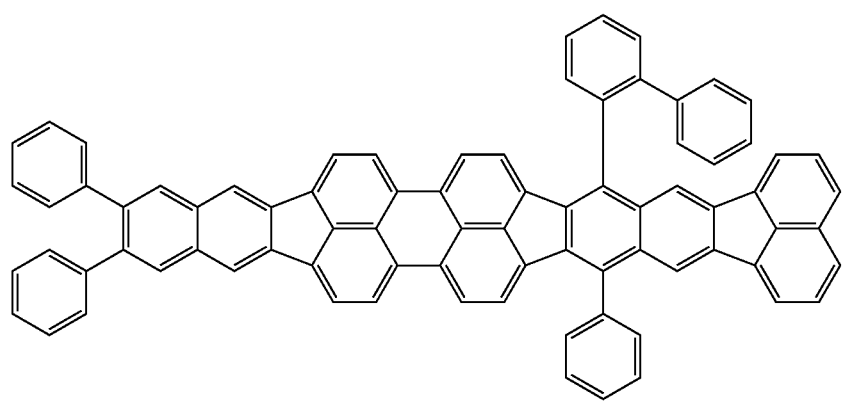
C4
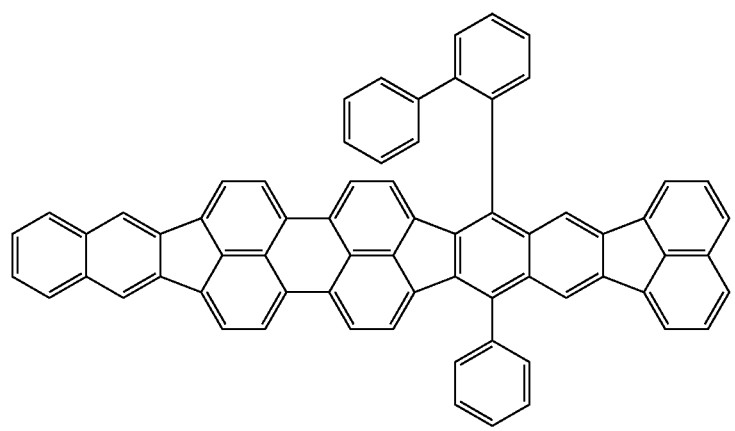
E5
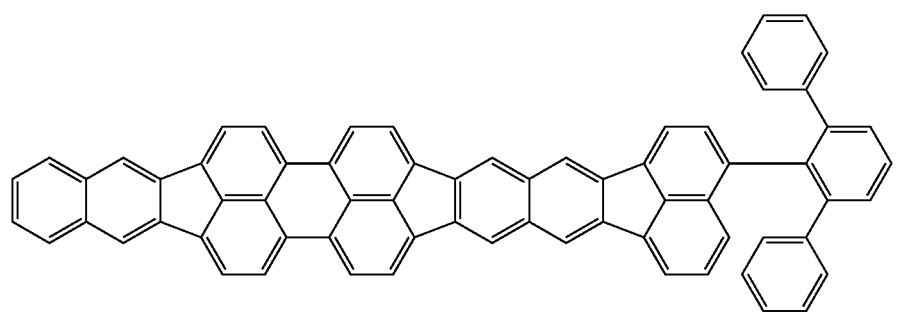
E6 E7
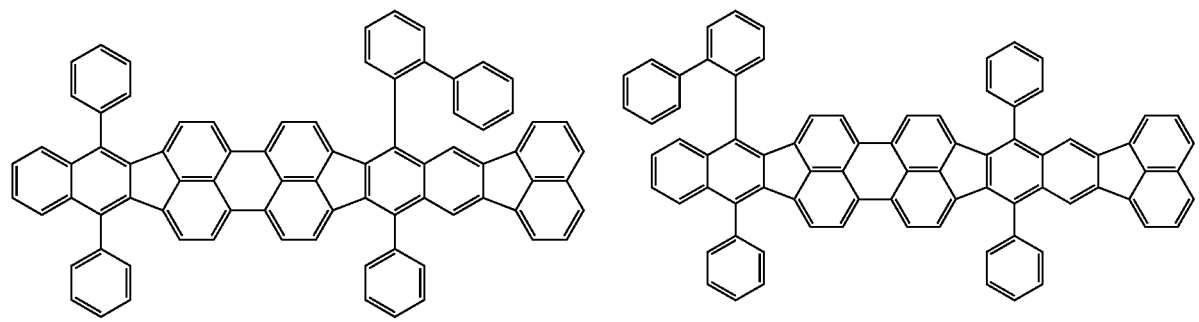

-continued
E8
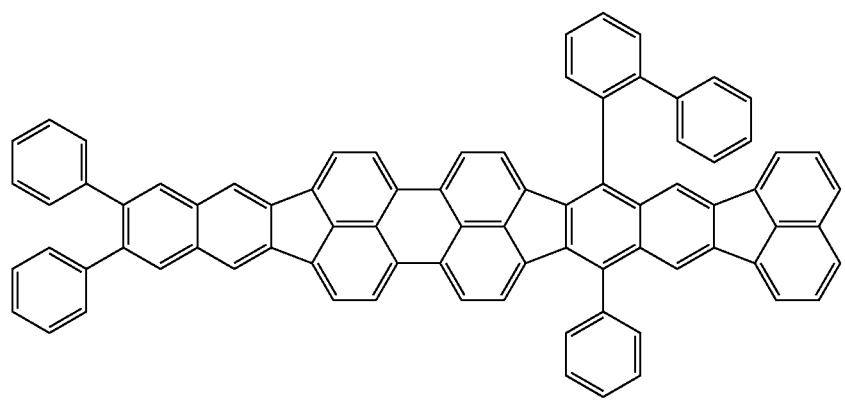
E9
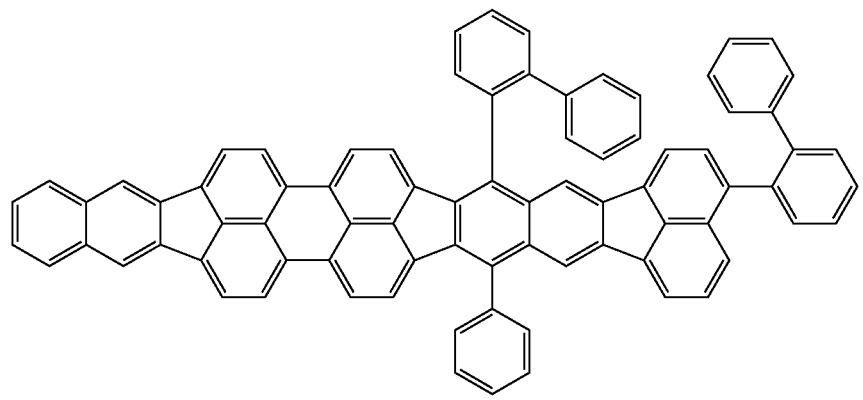
E10
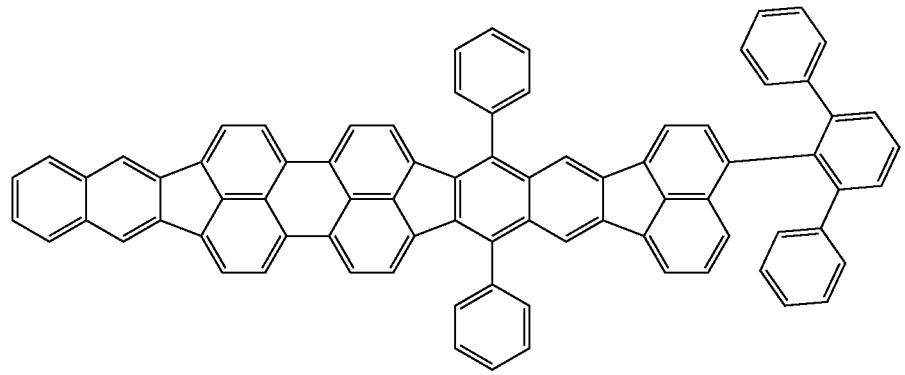
E11
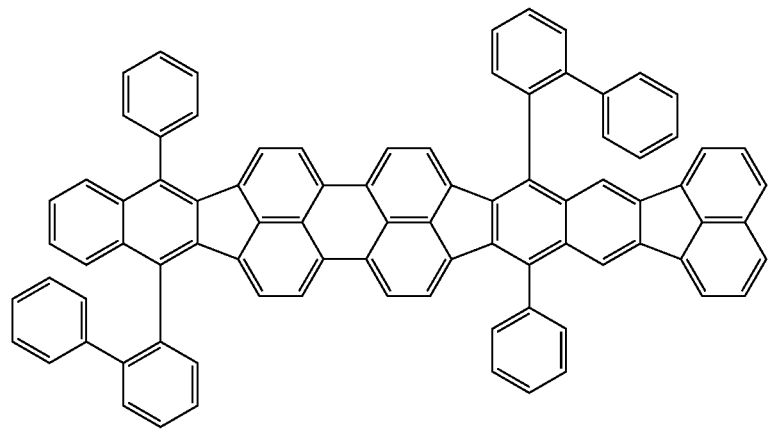

E12
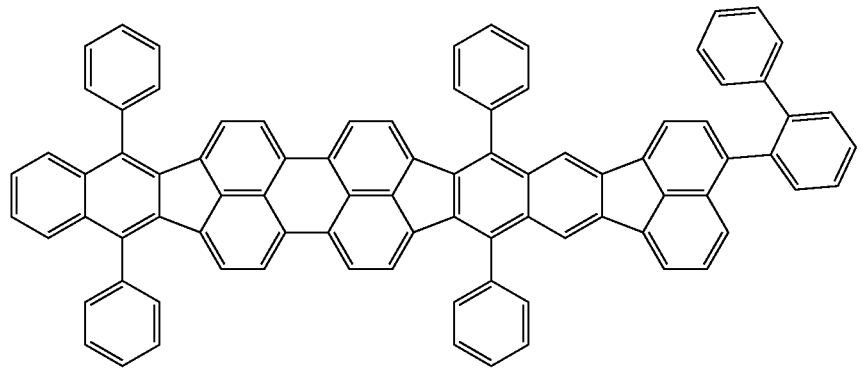
E13
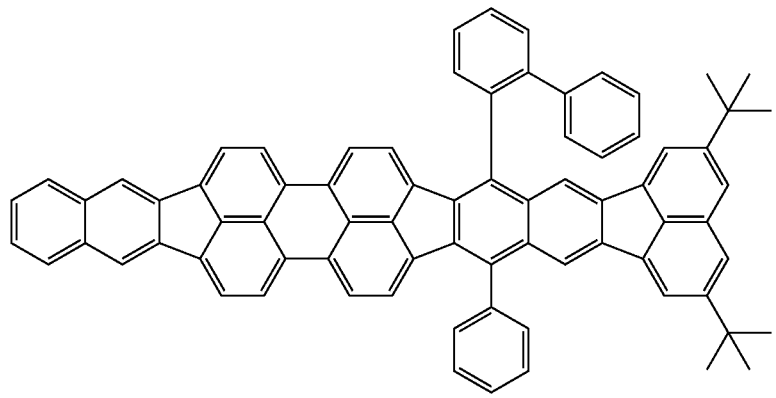
E14 E15
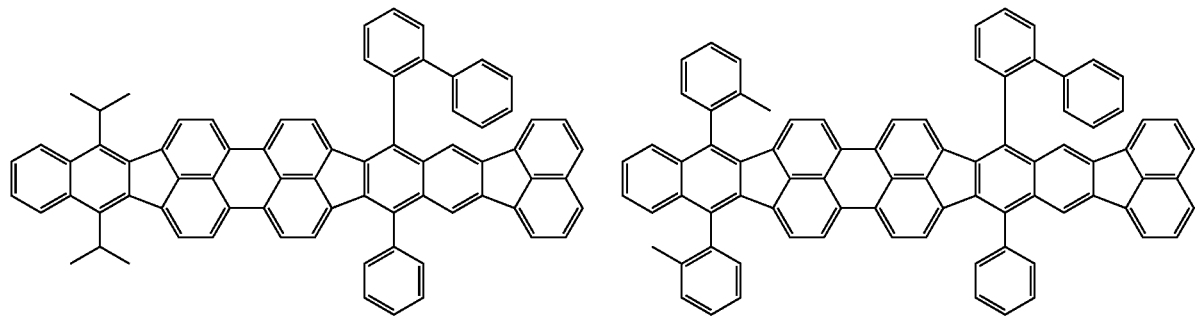
E16
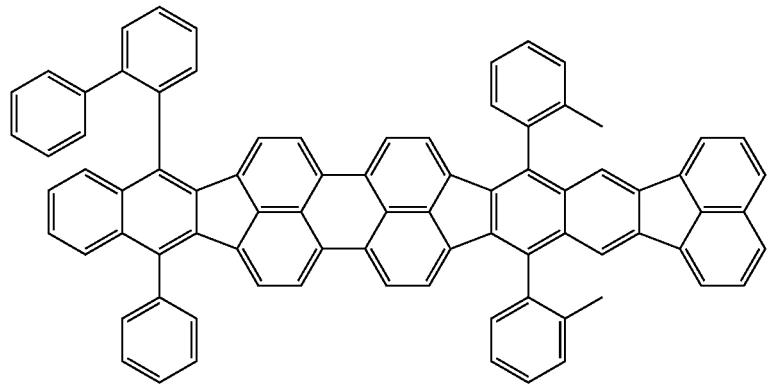

E17
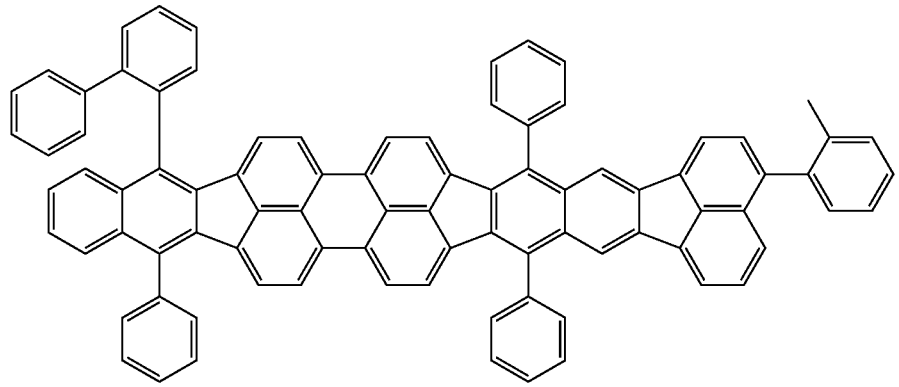
E18
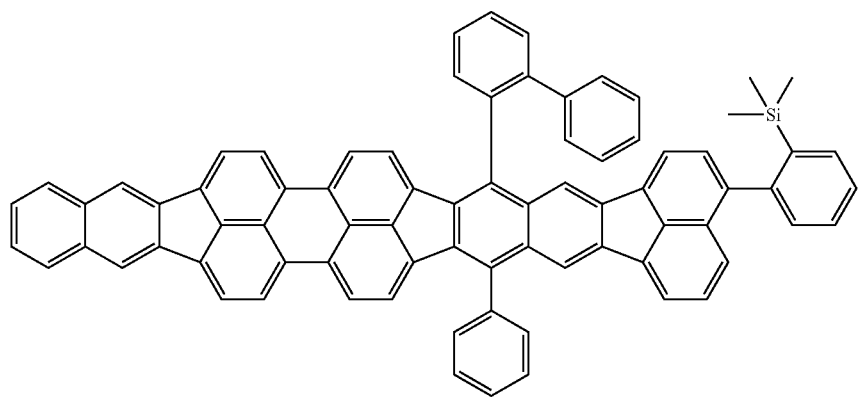
E19
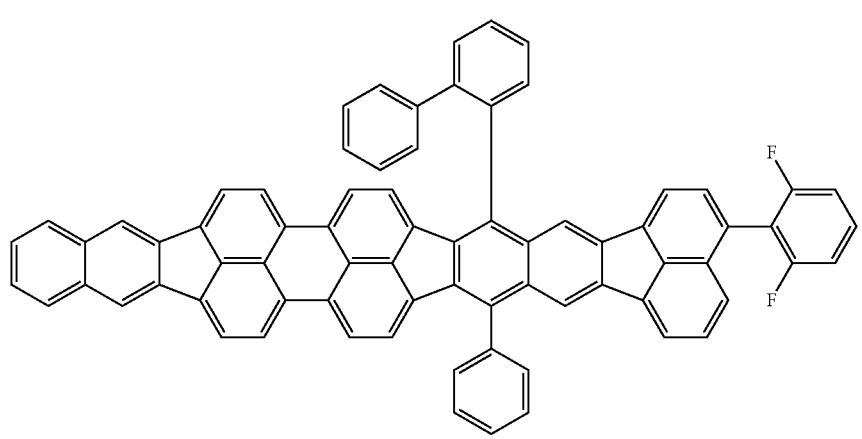

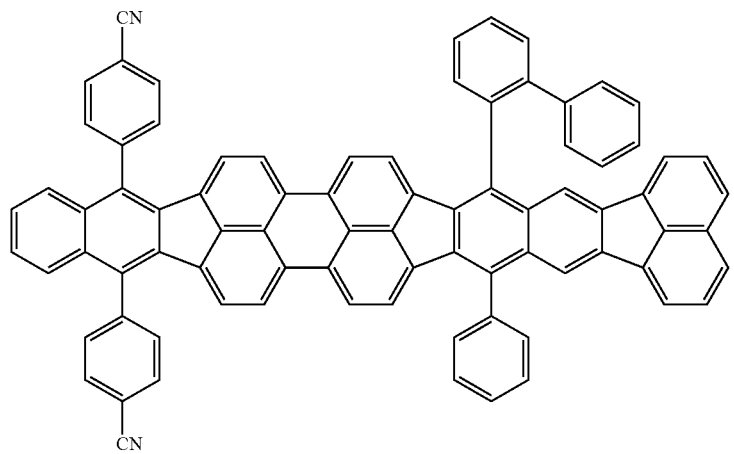

E20

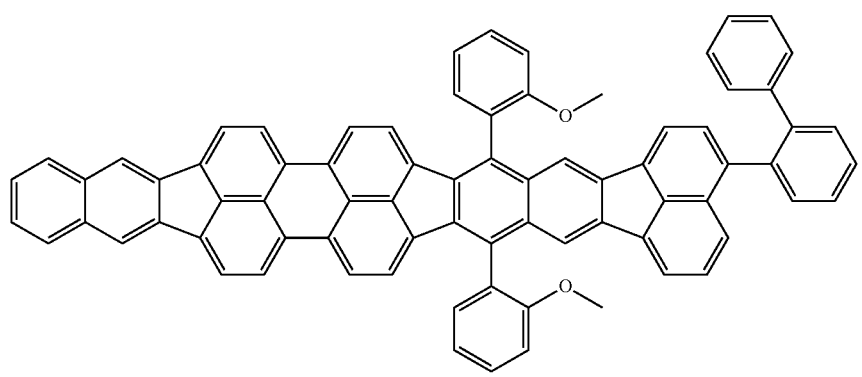

E21

Among the above exemplary compounds, those belonging to group A are compounds in each of which the whole molecule consists of a hydrocarbon. Compounds consisting of hydrocarbons have low HOMO energy levels. Compounds having low HOMO energy levels have low oxidation potentials and are stable against oxidation. Therefore, the compounds belonging to group A are organic compounds having low oxidation potentials, that is, being stable against oxidation.

Thus, among the exemplary compounds of the present disclosure, the exemplary compounds of group A are preferred for their high molecular stability. The organic compounds belonging to group A can also be used for light-emitting-layer host materials, transport layers, and injection layers.

Among the above exemplary compounds, those belonging to group B have substituents having heteroatoms. The exemplary compounds of group B have molecular oxidation potentials very different from those of compounds having no substituents. The organic compounds of group B, each having a substituent having a heteroatom, are useful as electron transport materials, hole transport materials, and hole-trapping luminescent materials. In particular, fluorine-substituted compounds have weak intermolecular interaction and thus can be expected to have improved sublimability.

Among the above exemplary compounds, compounds C1 to C11 and E1 to E12 are compounds in each of which the whole molecule consists of $SP^2$ hybridized carbon and hydrogen. Compounds consisting of $SP^2$ hybridized carbon and hydrogen typically have low HOMO energy levels. Therefore, compounds C1 to C11 and E1 to E12 are compounds having low oxidation potentials, that is, being stable against oxidation. Therefore, among the compounds according to this embodiment, organic compounds consisting of $SP^2$ hybridized carbon and hydrogen, that is, compounds C1 to C11 and E1 to E12, are preferred for their high molecular stability. More specifically, compounds C1 to C11 and E1 to E12 can also be used for light-emitting-layer host materials, transport layers, and injection layers.

Among the above exemplary compounds, compounds C12 to C18, D1 to D21, and E13 to E21 are examples in which an alkyl group, fluorine, an alkoxy group, an amino group, a heterocyclic group having 7 or more carbon atoms, a nitrogen-containing heterocyclic group, an aryloxy group, a silyl group, or a cyano group is introduced as $R_1$ to $R_{24}$ or as a substituent of $R_1$ to $R_{24}$. Compounds in which an alkyl group or fluorine is introduced can avoid intermolecular stacking and have low sublimation or vapor deposition onset temperatures, and when such compounds are used as light-emitting-layer guest materials, concentration quenching can be reduced. In addition, such compounds have improved solubility and thus can be used as coating materials. Compounds in which an alkoxy group, an aryloxy group, or a silyl group is introduced also have the effect of reducing concentration quenching and, in addition, can be used as coating materials. Compounds in which a nitrogen-containing heterocyclic group or a cyano group is introduced have the effect of withdrawing electrons from the basic skeleton, and thus have low HOMO energy levels and are more stable against oxidation among the compounds according to the present disclosure. Compounds in which an amino group is introduced have the effect of donating electrons to the basic skeleton, and thus have narrow band gaps and emit light having longer wavelengths. Compounds in which a heterocyclic group having 7 or more carbon atoms is introduced have higher glass transition temperatures than compounds in which a phenyl group is introduced, and when such a compound is used for a light-emitting-layer host material or a transport layer, a thermally stable amorphous film is formed.

Among the above exemplary compounds, compounds belonging to group D and compound E21 are examples which have at least one aryl group such as phenyl and pyridyl as $R_1$ to $R_{24}$ and in which at least one of an alkyl group, fluorine, an alkoxy group, and a cyano group is introduced at an ortho position of the aryl group. When a substituent is introduced at an ortho position of the aryl group, the aryl group is twisted with respect to the basic skeleton, and the substituent at the ortho position covers the π-conjugated plane of the basic skeleton, thus reducing molecular packing. As a result, intermolecular stacking is avoided more effectively than in the case of the compounds belonging to group C, leading to a low sublimation or vapor deposition onset temperature. When such a compound is used as a light-emitting-layer guest material, concentration quenching can be reduced.

Among the above exemplary compounds, those belonging to group E are examples which have a phenyl group as $R_1$ to $R_{24}$ and in which another phenyl group is further introduced at an ortho position of the phenyl group. The effect of covering the π-conjugated plane of the basic skeleton is greater than in the case of the compounds belonging to group D, and thus molecular packing is further reduced. As a result, intermolecular stacking is avoided more effectively than in the case of the compounds belonging to group D, leading to a low sublimation or vapor deposition onset temperature.

The organic compound according to one embodiment of the present disclosure is a compound that emits light suitable for red light emission. Thus, using the organic compound according to the present disclosure as a constituent material for an organic light-emitting element can provide an organic light-emitting element having good light-emitting properties and high durability.

Next, an organic light-emitting element according to one embodiment of the present disclosure will be described.

The organic light-emitting element according to one embodiment of the present disclosure includes a first electrode, a second electrode, and an organic compound layer disposed therebetween. The first electrode and the second electrode are, for example, an anode and a cathode, which are a pair of electrodes. In the organic light-emitting element according to one embodiment of the present disclosure, the organic compound layer may be a single layer or a layered body formed of a plurality of layers as long as the organic compound layer includes a light-emitting layer.

When the organic compound layer is a layered body formed of a plurality of layers, the organic compound layer may include, in addition to the light-emitting layer, a hole injection layer, a hole transport layer, an electron blocking layer, a hole/exciton blocking layer, an electron transport layer, an electron injection layer, and other layers. The light-emitting layer may be a single layer or a layered body formed of a plurality of layers.

In the organic light-emitting element according to one embodiment of the present disclosure, at least one layer in the organic compound layer contains the organic compound according to one embodiment of the present disclosure. Specifically, the organic compound represented by formula (1) is contained in any of the light-emitting layer, the hole injection layer, the hole transport layer, the electron blocking layer, the light-emitting layer, the hole/exciton blocking layer, the electron transport layer, the electron injection layer, and the other layers described above. The organic compound of formula (1) may be contained in the light-emitting layer. In this case, the emission color of the organic light-emitting element may be any color such as one of the three primary colors, white, or an intermediate color.

In the organic light-emitting element according to one embodiment of the present disclosure, when the organic compound represented by formula (1) is contained in the light-emitting layer, the light-emitting layer may be a layer formed only of the organic compound of formula (1) or a layer formed of the organic compound of formula (1) and other compounds. When the light-emitting layer is a layer formed of the organic compound of formula (1) and other compounds, the organic compound of formula (1) may be used as a host or guest of the light-emitting layer. The organic compound may also be used as an assist that can be contained in the light-emitting layer.

As used herein, the term "host" refers to a compound having the highest weight ratio among the compounds constituting the light-emitting layer. The term "guest" refers to a compound that has a lower weight ratio than the host among the compounds constituting the light-emitting layer and that mainly contributes to light emission. The term "assist" refers to a compound that has a lower weight ratio than the host among the compounds constituting the light-emitting layer and that assists the light emission of the guest. The assist is also referred to as a second host.

When the organic compound of formula (1) is used as a guest of the light-emitting layer, the concentration of the guest is preferably 0.01 wt % or more and 20 wt % or less, more preferably 0.1 wt % or more and 5.0 wt % or less, based on the total weight of the light-emitting layer.

When the organic compound represented by formula (1) is used as a guest of the light-emitting layer, a material having a higher LUMO energy level than the organic compound (a material having a LUMO energy level closer to the vacuum level) may be used as a host. This is due to the following: the organic compound represented by formula (1) has a low LUMO energy level, and thus using a material having a higher LUMO energy level than the organic compound of formula (1) as a host allows the guest to more readily receive electrons supplied to the host of the light-emitting layer.

The present inventors have conducted various studies and found that using the organic compound of formula (1) as a host or guest of the light-emitting layer, particularly, as a guest of the light-emitting layer provides an element that produces an optical output with high efficiency and high luminance and that has very high durability. This light-emitting layer may have a single-layer structure or a multilayer structure. The term "multilayer structure" means a state in which the light-emitting layer and another light-emitting layer are stacked on top of each other. In this case, the emission color of the organic light-emitting element is not limited to red. More specifically, the emission color may be white or an intermediate color. In the case of white, the other light-emitting layer emits light of a color other than red, that is, blue or green light. The light-emitting layer is formed by a method such as vapor deposition or coating.

In addition to the organic compound according to this embodiment, known low-molecular-weight and high-molecular-weight hole injection compounds or hole transport compounds, compounds serving as hosts, luminescent compounds, electron injection compounds or electron transport compounds, and the like may optionally be used in combination.

Examples of these compounds will be described below.

As hole injection and transport materials, materials that facilitate injection of holes from the anode and that have so high hole mobility that enables injected holes to be transported to the light-emitting layer may be used. To prevent deterioration of film quality, such as crystallization, in the organic light-emitting element, materials having high glass-transition temperatures may be used. Examples of low-molecular-weight and high-molecular-weight materials having hole injection and transport properties include triarylamine derivatives, arylcarbazole derivatives, phenylenediamine derivatives, stilbene derivatives, phthalocyanine derivatives, porphyrin derivatives, poly(vinylcarbazole), poly(thiophene), and other conductive polymers. These hole injection and transport materials are also suitable for use in the electron blocking layer.

Non-limiting specific examples of compounds usable as hole injection and transport materials are shown below.

HT1
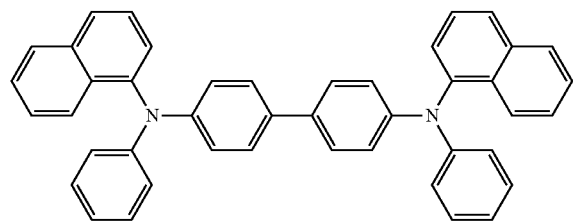

HT2
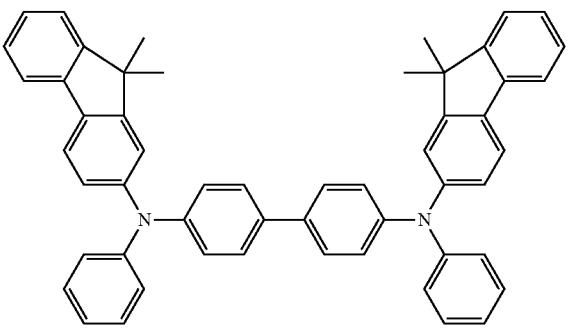

HT3
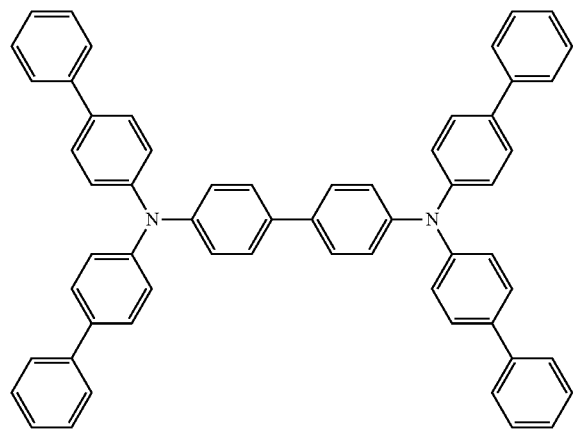

HT4
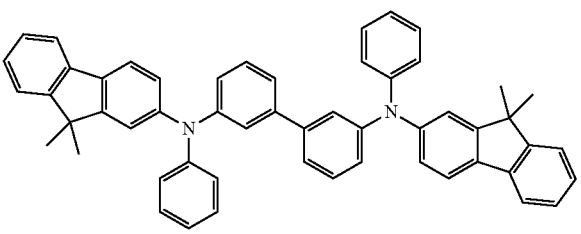

HT5
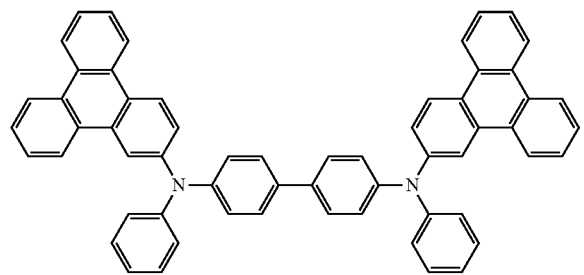

HT6
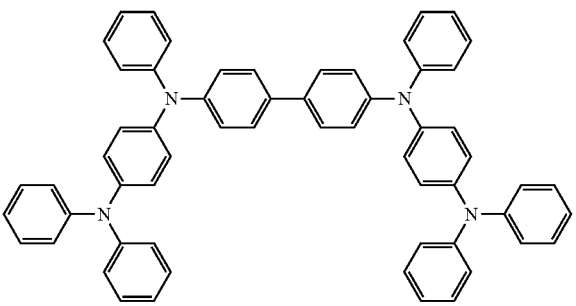

-continued
HT7
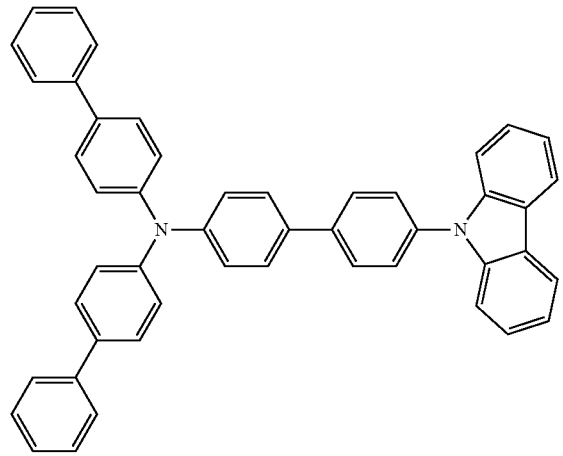
HT8
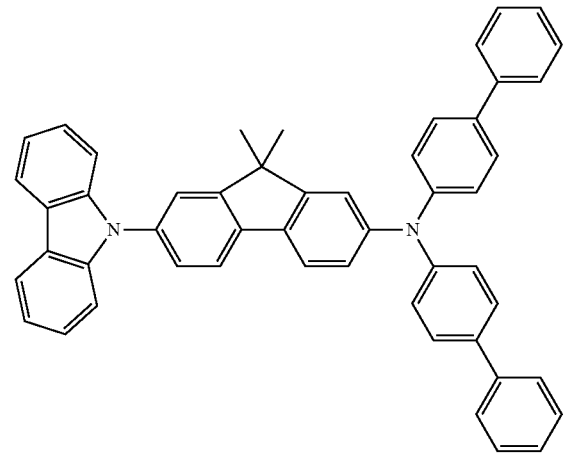
HT9
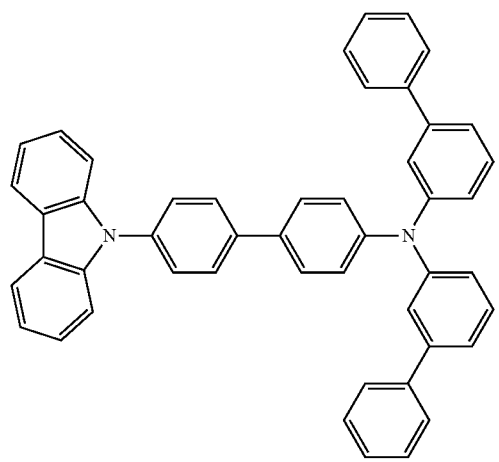
HT10
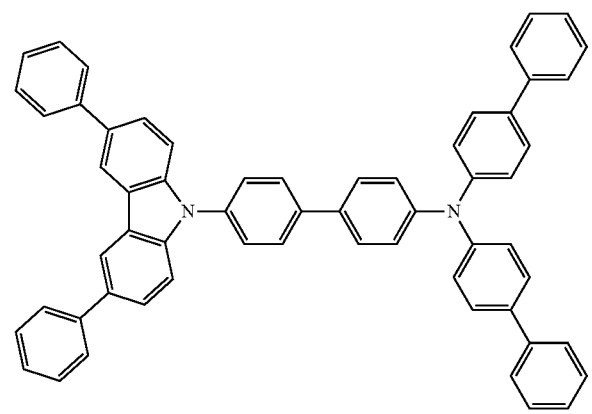
HT11
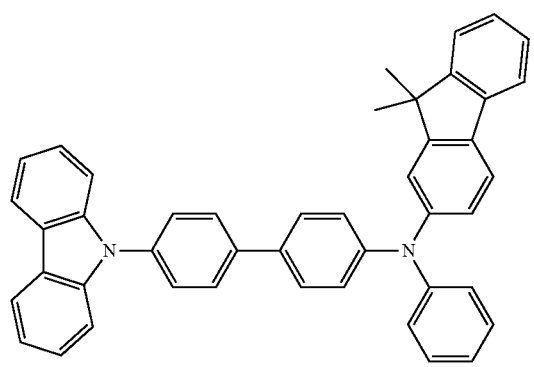
HT12
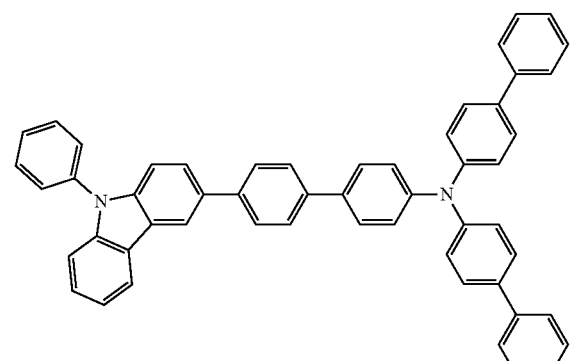

-continued

HT13

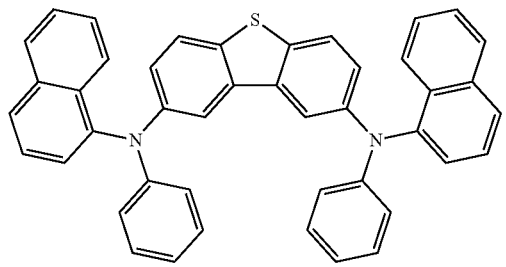

HT14

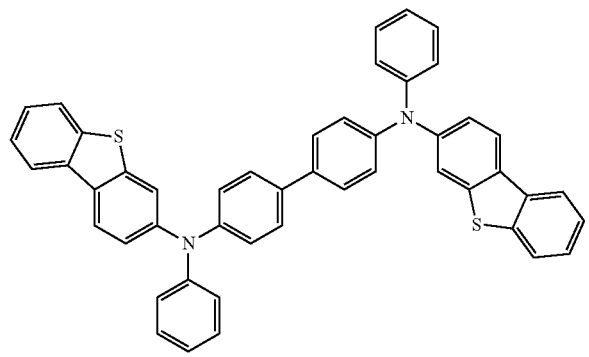

HT15

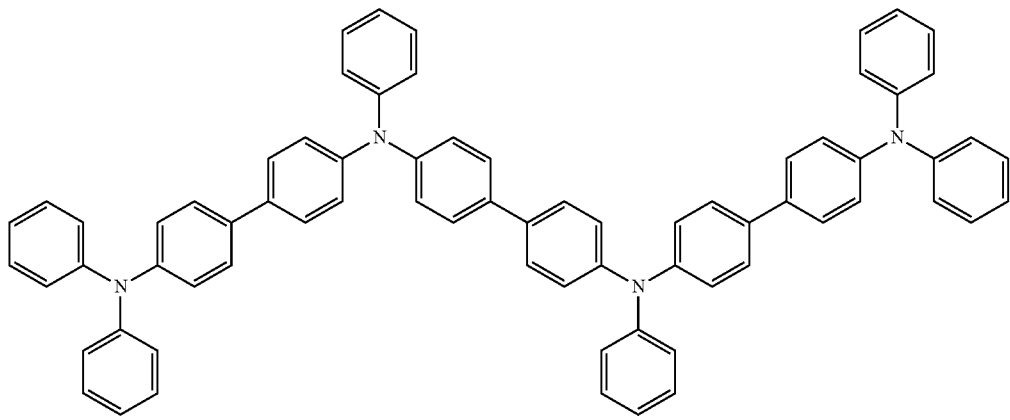

HT16

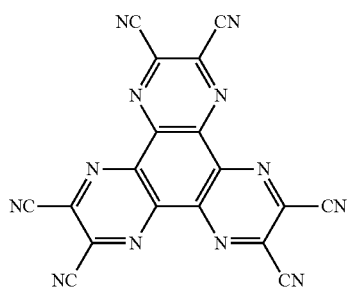

HT17

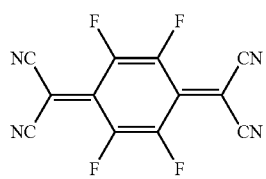

HT18

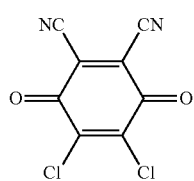

HT19

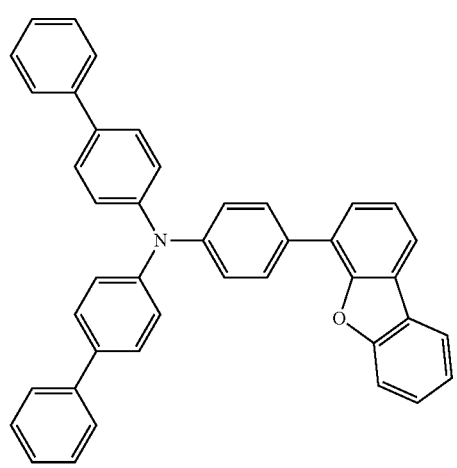

Examples of luminescent materials mainly contributing to the light-emitting function include the organic compound represented by formula (1), condensed-ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato)aluminum, iridium complexes, platinum complexes, rhenium complexes, copper complexes, europium complexes, ruthenium complexes, and polymer derivatives such as poly(phenylenevinylene) derivatives, poly(fluorene) derivatives, and poly(phenylene) derivatives.

The organic compound of the present disclosure is a compound having a narrow band gap and a low HOMO/LUMO energy level. Therefore, when a mixture layer is formed with another luminescent material or when light-emitting layers are stacked on top of each other, the other luminescent material may also have a low HOMO/LUMO energy level. This is because if the HOMO/LUMO energy level is high, a quenching component or a trap level may be formed; for example, the other luminescent material may form an exciplex together with the organic compound of the present disclosure.

Non-limiting specific examples of compounds usable as luminescent materials are shown below.

BD1

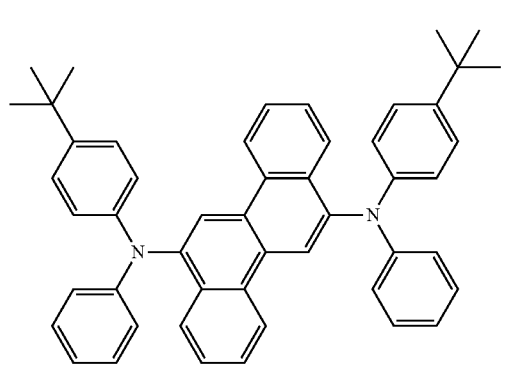

BD2

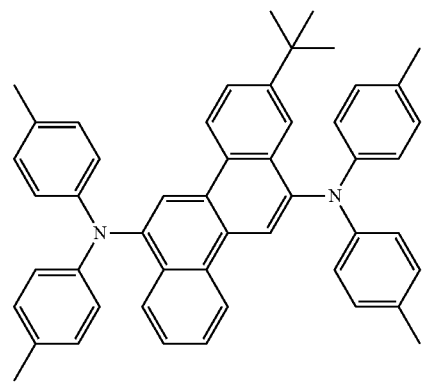

BD3

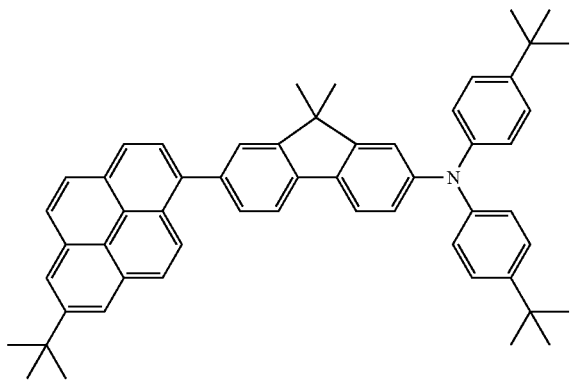

BD4

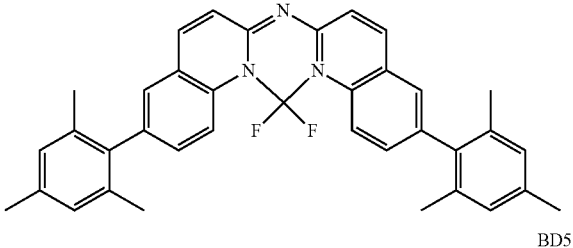

BD5

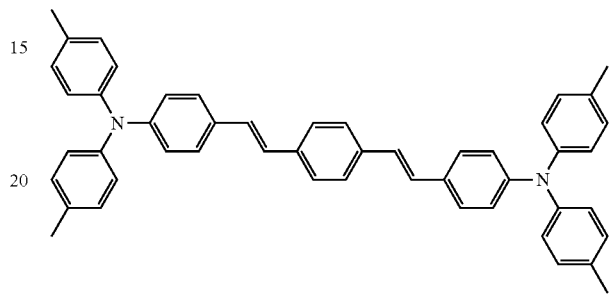

BD6

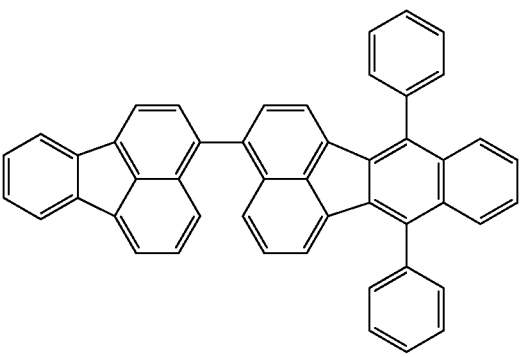

BD7

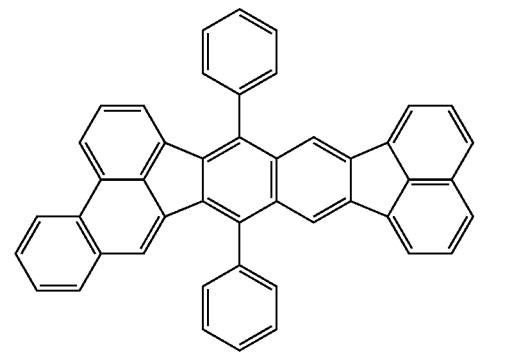

BD8

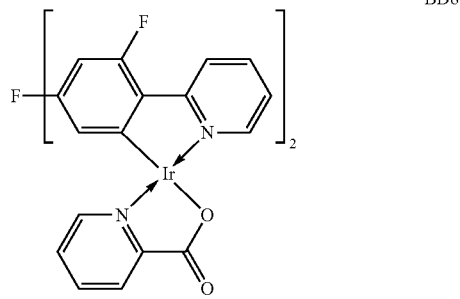

GD1 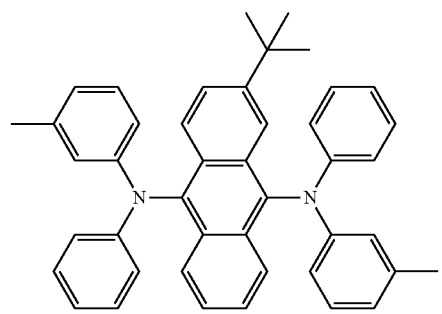
GD2 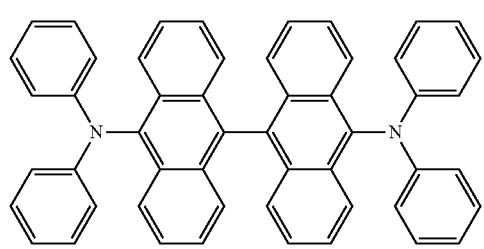
GD3 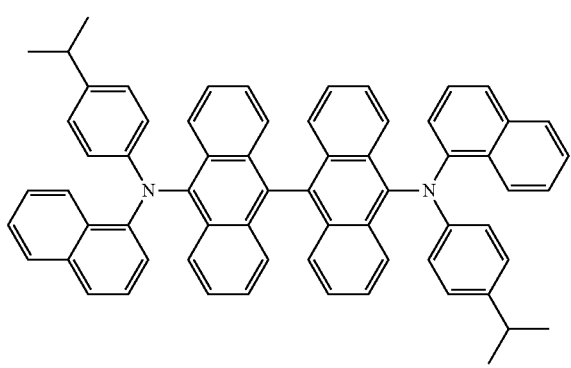
GD4 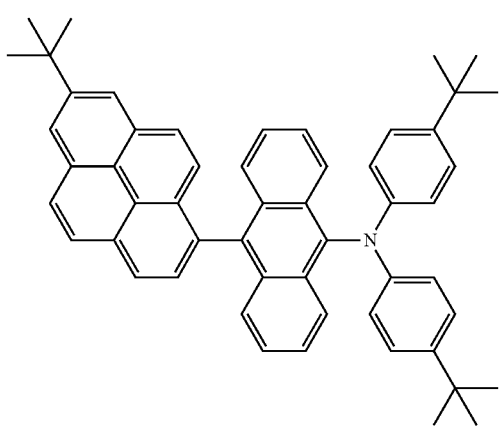
GD5 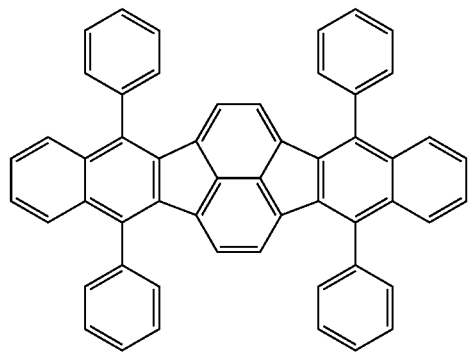
GD6 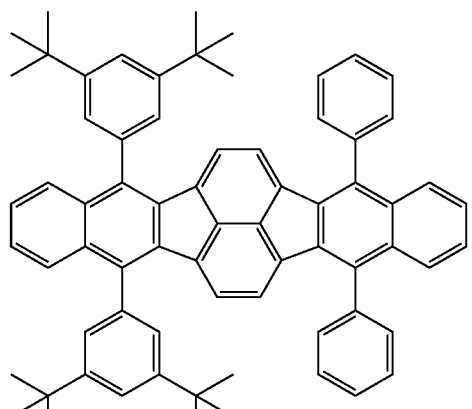
GD7 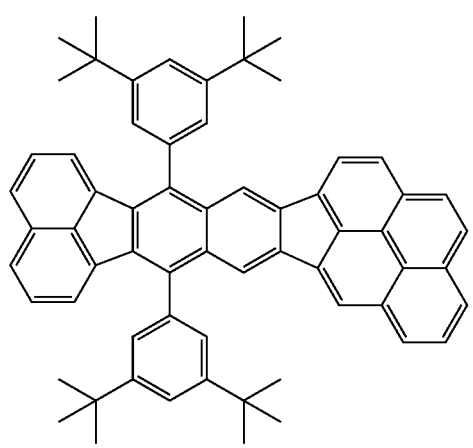
GD8 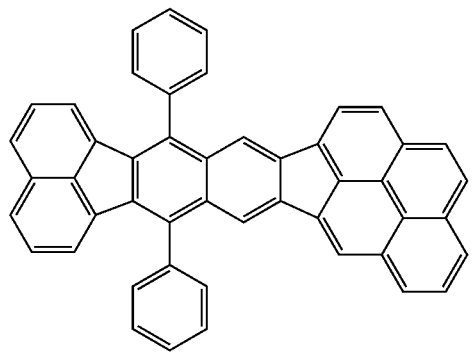

GD9

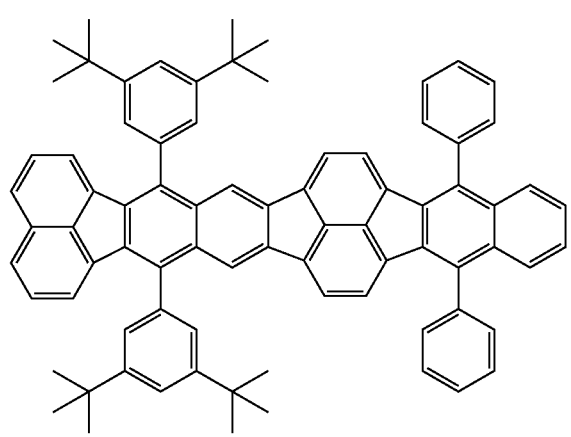

GD10

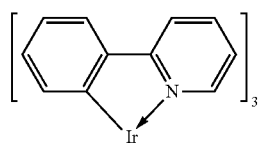

GD11

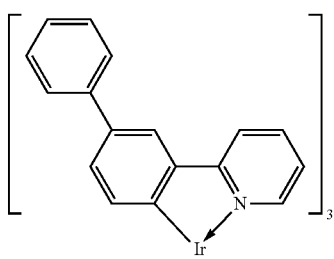

GD12

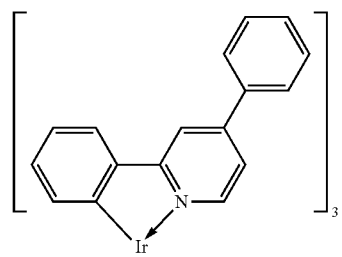

Examples of light-emitting-layer host materials and light emission assist materials contained in the light-emitting layer include aromatic hydrocarbon compounds and derivatives thereof, carbazole derivatives, dibenzofuran derivatives, dibenzothiophene derivatives, organic aluminum complexes such as tris(8-quinolinolato)aluminum, and organic beryllium complexes.

The organic compound according to one embodiment of the present disclosure is a compound having a narrow band gap and a low HOMO/LUMO energy level. Therefore, the host material may also be formed of a hydrocarbon and have a low HOMO/LUMO energy level. This is because if the host material contains a heteroatom such as nitrogen, the HOMO/LUMO energy level will be high, and a quenching component or a trap level may be formed; for example, the other luminescent material may form an exciplex together with the organic compound of the present disclosure.

In particular, the host material may have an anthracene, tetracene, perylene, or pyrene skeleton in its molecular skeleton. This is because the host is formed of a hydrocarbon as described above and also has an S1 energy capable of causing sufficient energy transfer in the organic compound of the present disclosure.

Non-limiting specific examples of compounds usable as light-emitting-layer host or light emission assist materials contained in the light-emitting layer are shown below.

EM1

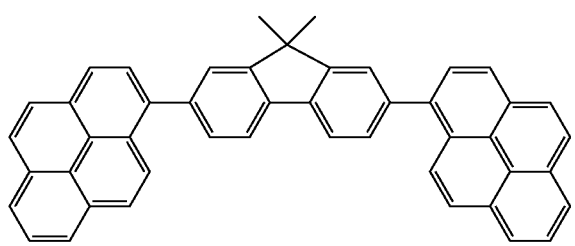

EM2

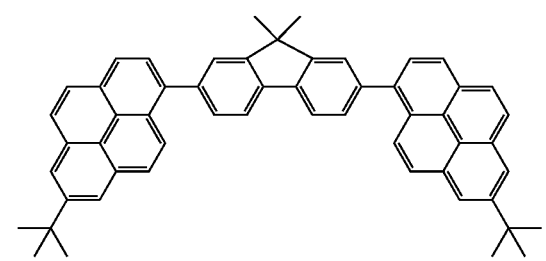

EM3

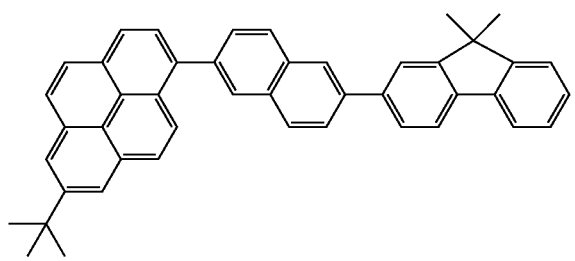

EM4

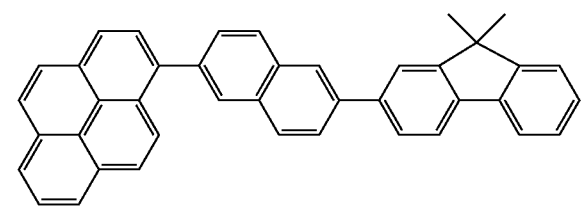

-continued
EM5
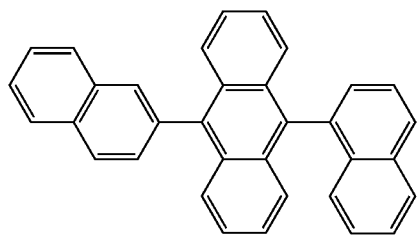
EM6
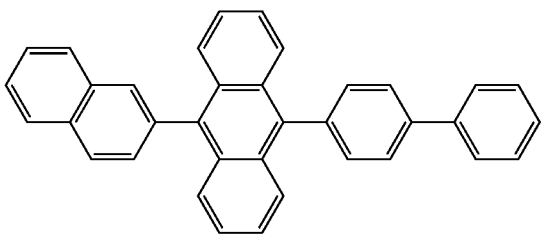
EM7
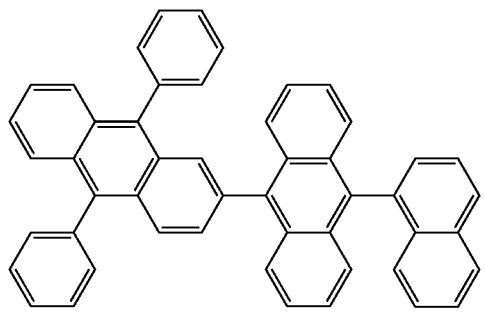
EM8
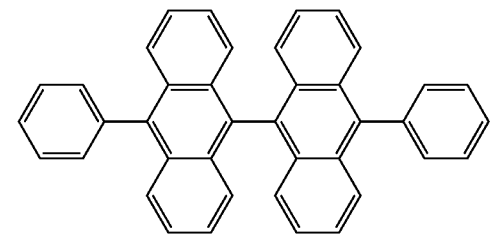
EM9
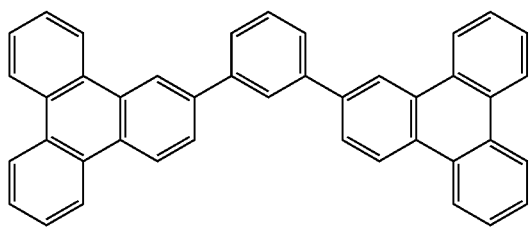
EM10
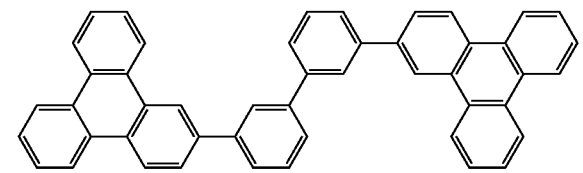
EM11
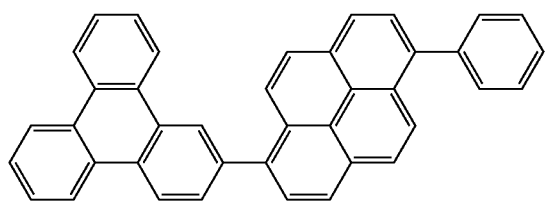
EM12
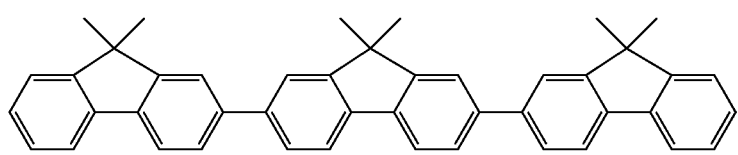
EM13
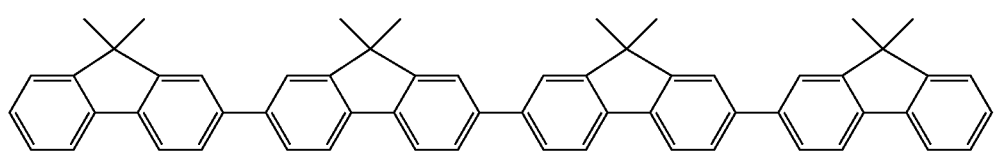
EM14
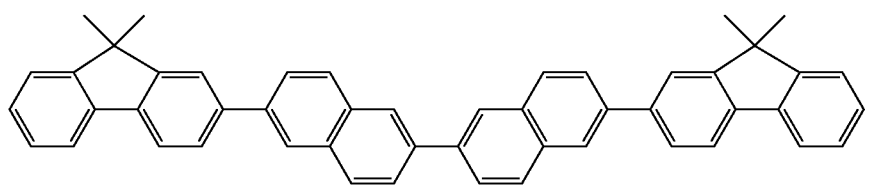

-continued
EM15
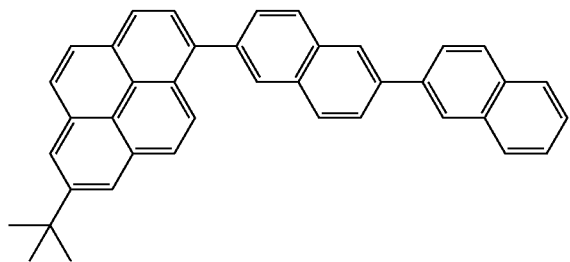
EM16
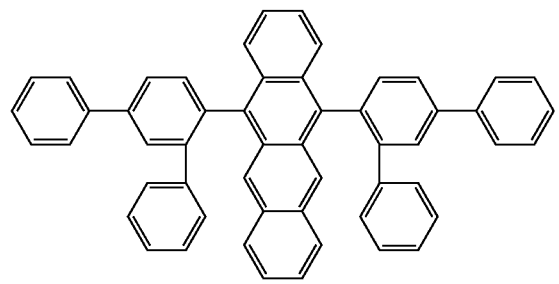
EM17
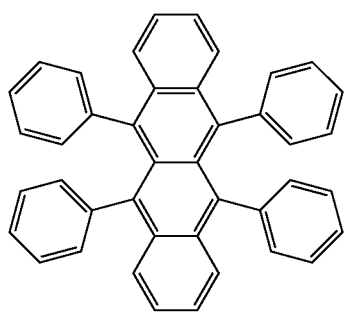
EM18
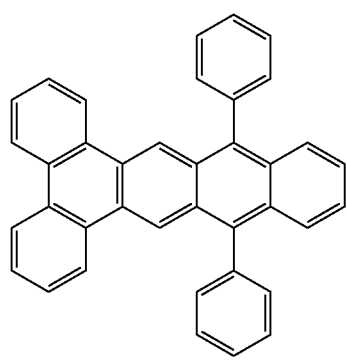
EM19
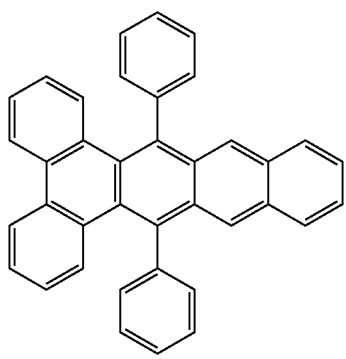
EM20
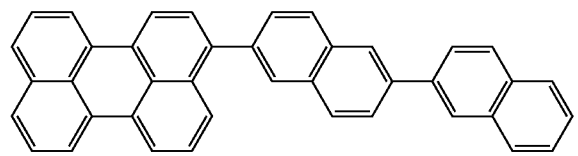
EM21
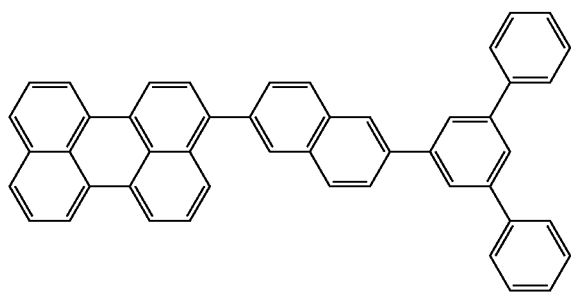
EM22
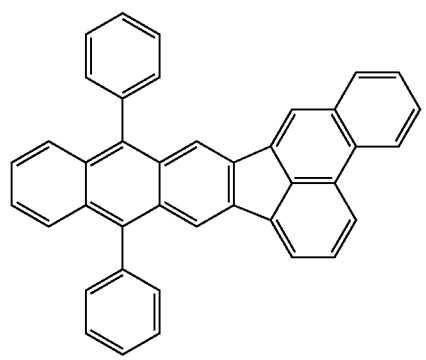

EM23 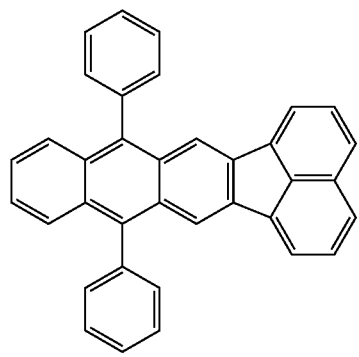
EM24 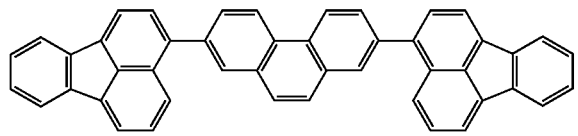
EM25 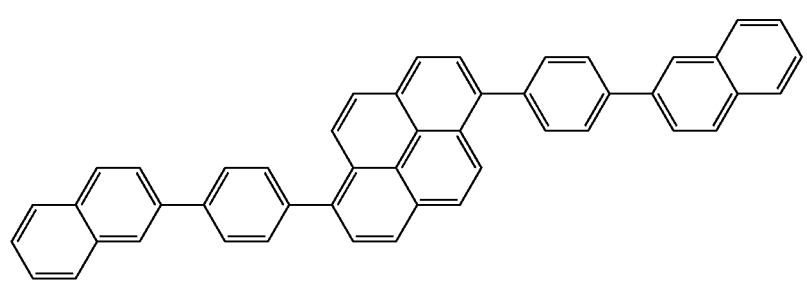
EM26 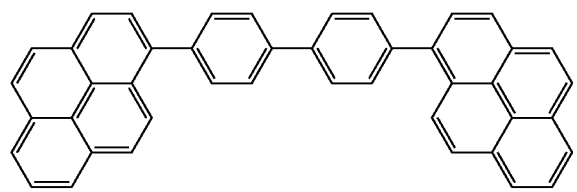
EM27 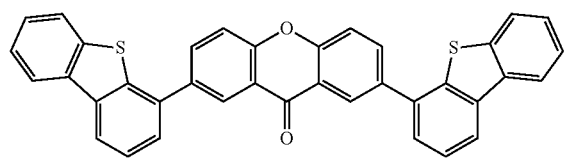
EM28 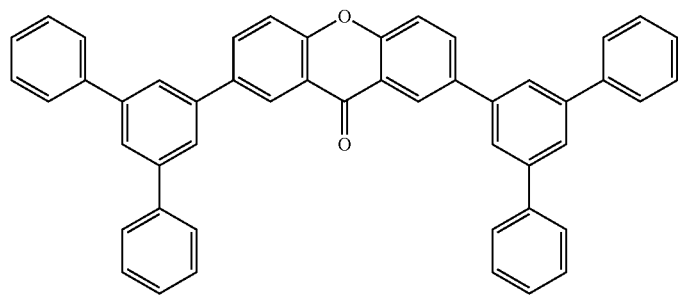
EM29 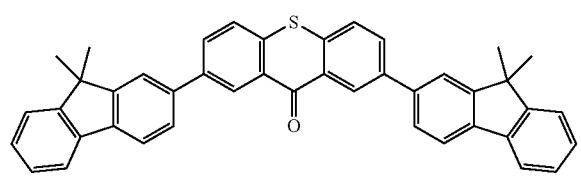
EM30 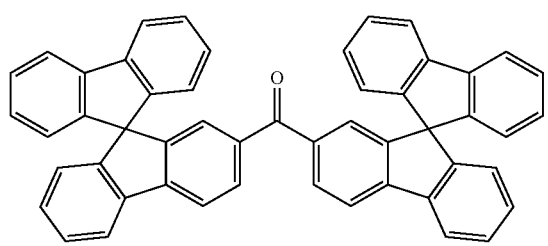

-continued

EM31

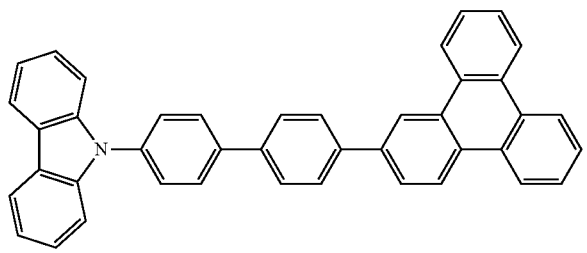

EM32

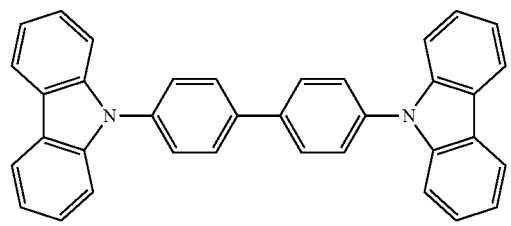

Any electron transport material capable of transporting electrons injected from the cathode to the light-emitting layer can be freely selected taking into account, for example, the balance with the hole mobility of a hole transport material. Examples of materials capable of transporting electrons include oxadiazole derivatives, oxazole derivatives, pyrazine derivatives, triazole derivatives, triazine derivatives, quinoline derivatives, quinoxaline derivatives, phenanthroline derivatives, organic aluminum complexes, and condensed-ring compounds (e.g., fluorene derivatives, naphthalene derivatives, chrysene derivatives, and anthracene derivatives). These electron transport materials are also suitable for use for the hole blocking layer.

Non-limiting specific examples of compounds usable as electron transport materials are shown below.

-continued

ET4

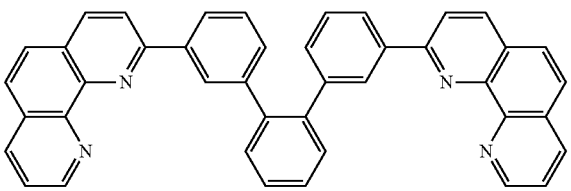

ET5

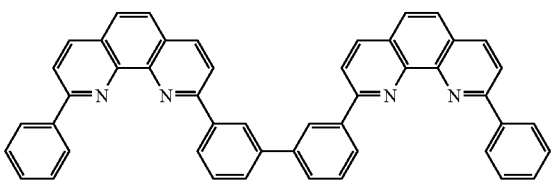

ET1

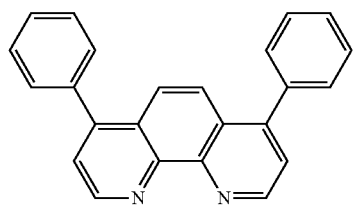

ET6

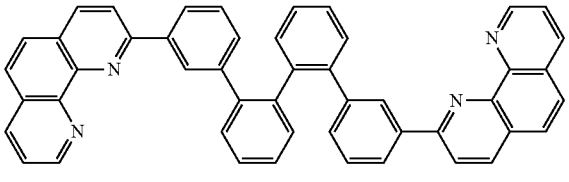

ET2

ET3

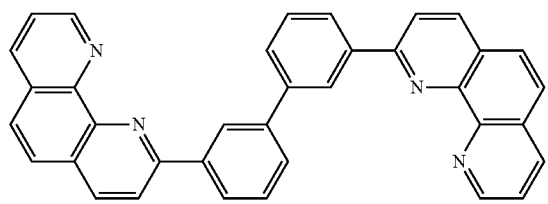

ET7

ET8

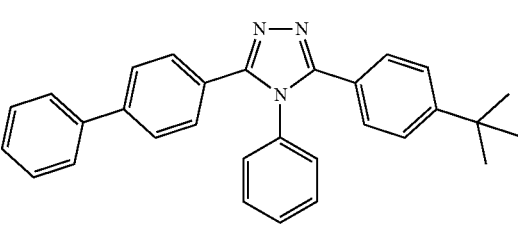

ET9
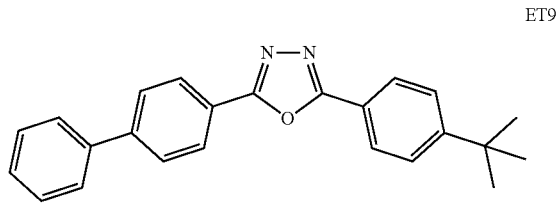
ET10
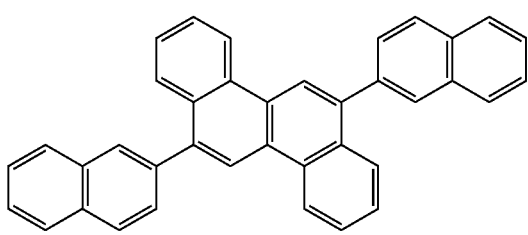
ET11
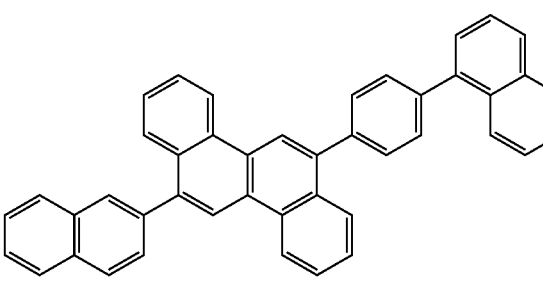
ET12
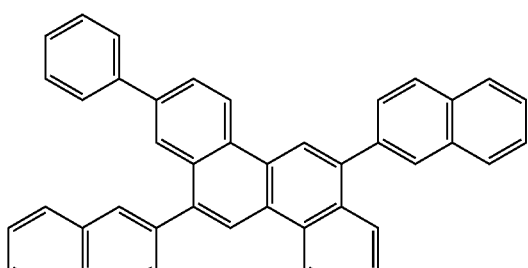
ET13
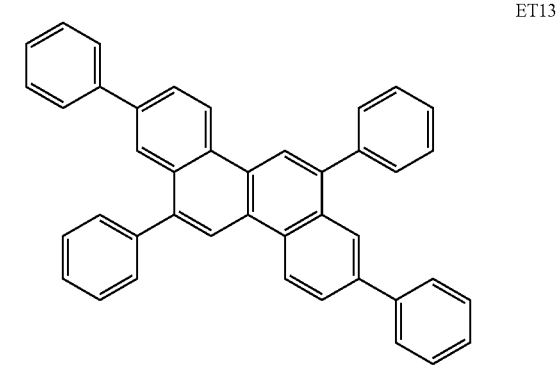
ET14
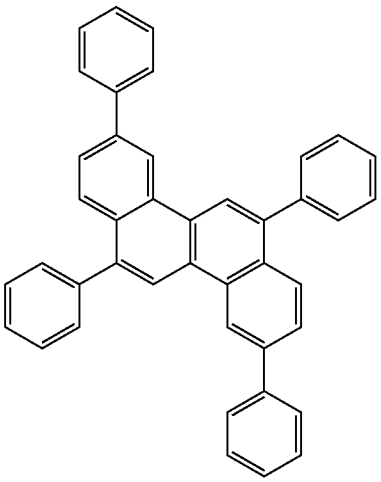
ET15
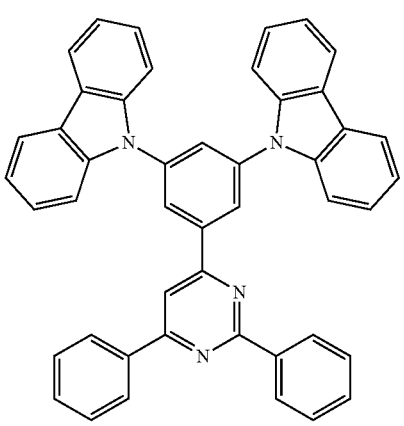
ET16
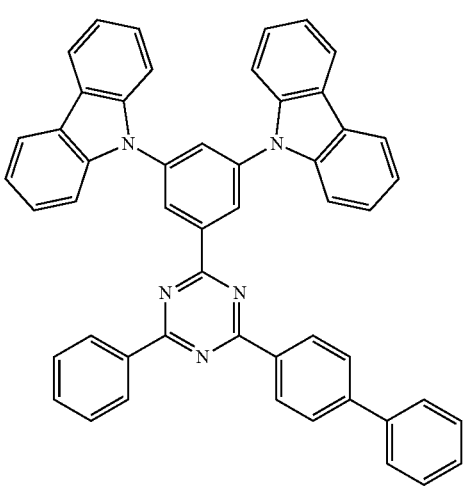

ET17
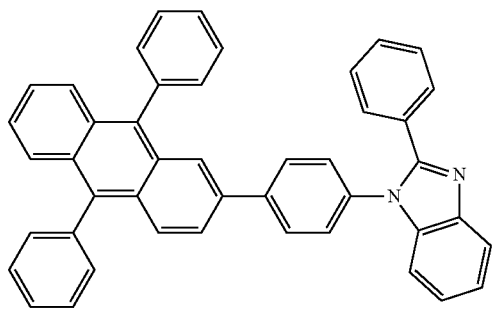

ET18
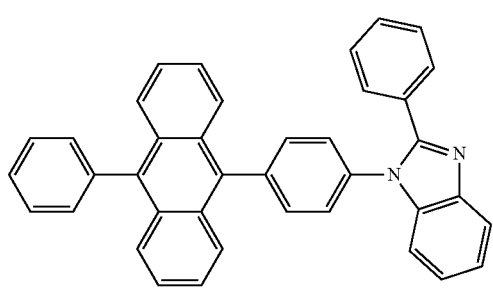

ET19
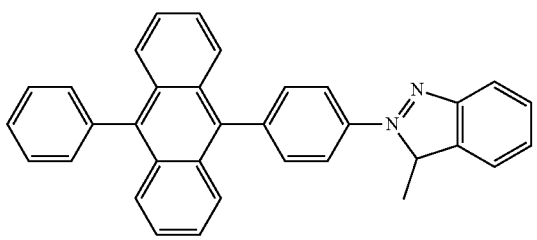

ET20
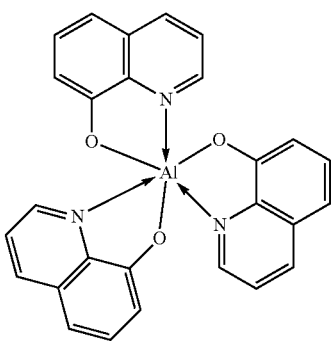

ET21
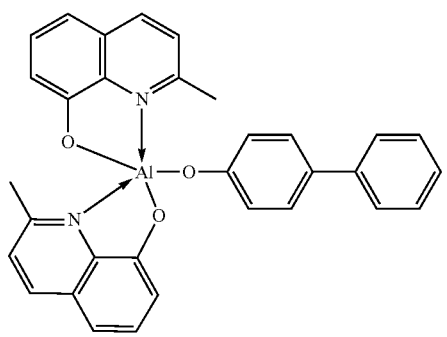

ET22
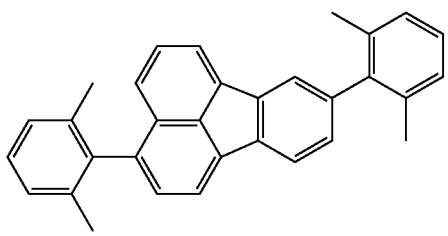

ET23
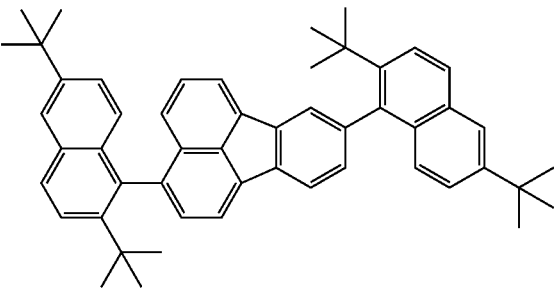

Configuration of Organic Light-Emitting Element According to One Embodiment of Present Disclosure An organic light-emitting element is obtained by forming an anode, an organic compound layer, and a cathode on a substrate. A protective layer, a color filter, and the like may be disposed on the cathode. If a color filter is disposed, a planarizing layer may be disposed in advance.

The organic light-emitting element according to this embodiment may be of top-emission type or bottom-emission type. When the organic light-emitting element is of top-emission type, the substrate and the electrode on the substrate side may be transparent. When the organic light-emitting element is of bottom-emission type, the electrode on the side opposite the substrate may be transparent.

Outgoing light may be enhanced by adjusting the optical length between the electrodes. To enhance the outgoing light, the optical length may be ¼ or ¾ of the wavelength of the light to be enhanced. More generally, the optical length may be $(2m-1)/4$, where m is a natural number.

The substrate may be made of, for example, quartz, glass, a silicon wafer, a resin, or a metal. The substrate may have lines and switching elements such as transistors disposed thereon, and an insulating layer may be disposed thereon. The insulating layer may be made of any material as long as a contact hole can be formed in order to provide an electrical connection between the anode and a line and insulation for an unconnected line can be provided. For example, resins such as polyimide, silicon oxide, and silicon nitride can be used.

The anode may be made of a material having as high a work function as possible. For example, metals such as gold, platinum, silver, copper, nickel, palladium, cobalt, selenium, vanadium, and tungsten, mixtures containing these metals, alloys of these metals, and metal oxides such as tin oxide, zinc oxide, indium oxide, indium tin oxide (ITO), and indium zinc oxide can be used. Conductive polymers such as polyaniline, polypyrrole, and polythiophene can also be used.

These electrode materials can be used alone or in combination. The anode may be formed of a single layer or multiple layers.

When the anode is used as a reflection electrode, chromium, aluminum, silver, titanium, tungsten, molybdenum, an alloy thereof, or a laminate thereof can be used, for example. When the anode is used as a transparent electrode, a transparent conductive oxide layer of, for example, indium tin oxide (ITO) or indium zinc oxide can be used, but these are not limiting examples. Photolithography can be used for electrode formation.

The cathode may be made of a material having as low a work function as possible. Examples of such materials include alkali metals such as lithium; alkaline earth metals such as calcium; metals such as aluminum, titanium, manganese, silver, lead, and chromium; and mixtures containing these metals. Alloys of these metals can also be used. For example, magnesium-silver, aluminum-lithium, aluminum-magnesium, silver-copper, and zinc-silver alloys can be used. Metal oxides such as indium tin oxide (ITO) can also be used. These electrode materials can be used alone or in combination. The cathode may be formed of a single layer or multiple layers.

The cathode may be formed by any method. For example, DC and AC sputtering advantageously provides good film coverage to readily reduce resistance.

After the cathode is formed, a sealing member may be disposed. For example, bonding a glass plate provided with a moisture absorbent to the cathode can reduce permeation of water into organic EL layers, thus reducing the occurrence of a display failure. In another embodiment, a passivation film made of, for example, silicon nitride may be disposed on the cathode to reduce permeation of water into organic EL layers. For example, a protective layer may be formed in such a manner that the cathode, after being formed, is conveyed to another chamber without breaking the vacuum, and a silicon nitride film having a thickness of 2 µm is formed thereon by CVD.

Color filters may be disposed on pixels. For example, color filters sized to fit pixels may be disposed on another substrate and bonded to a substrate provided with an organic EL element. Alternatively, color filters may be patterned on a sealing film of, for example, silicon oxide by photolithography.

The organic compound layers (e.g., the hole injection layer, the hole transport layer, the electron blocking layer, the light-emitting layer, the hole blocking layer, the electron transport layer, and the electron injection layer) constituting the organic light-emitting element according to this embodiment are formed by the following method.

The organic compound layers constituting the organic light-emitting element according to this embodiment can each be formed using a dry process such as vacuum deposition, ionized deposition, sputtering, or plasma deposition. Alternatively, the organic compound layers can each be formed using a wet process by applying a solution of an organic compound in an appropriate solvent by a known coating method (e.g., spin coating, dipping, casting, the LB technique, or ink-jet coating).

Layers formed by vacuum deposition or solution coating are unlikely to undergo deterioration such as crystallization and are highly stable over time. When a coating method is used, an appropriate binder resin can be used in combination to form a film.

Examples of binder resins include, but are not limited to, polyvinylcarbazole resins, polycarbonate resins, polyester resins, ABS resins, acrylic resins, polyimide resins, phenol resins, epoxy resins, silicone resins, and urea resins.

These binder resins may be used alone as a homopolymer or copolymer or may be used as a mixture of two or more.

In addition, known additives such as plasticizers, antioxidants, and UV absorbers may optionally be used in combination. Applications of organic light-emitting element according to one embodiment of present disclosure The organic light-emitting element according to this embodiment can be used as a component of a display apparatus or a lighting apparatus. Other applications include an exposure light source in an electrophotographic image-forming apparatus, a backlight in a liquid-crystal display apparatus, and a light-emitting apparatus including a white light source with a color filter.

The display apparatus may be an image information processing apparatus including an image input unit that receives image information from, for example, an area CCD, a linear CCD, and a memory card, an information-processing unit that processes the input information, and a display unit that displays the input image.

The display unit of an image pickup apparatus or an ink-jet printer may have a touch panel function. The touch panel function may be activated by any system, such as an infrared system, an electrostatic capacitive system, a resistive film system, or an electromagnetic induction system. The display apparatus may also be used in a display unit of a multifunctional printer.

Figure 3:
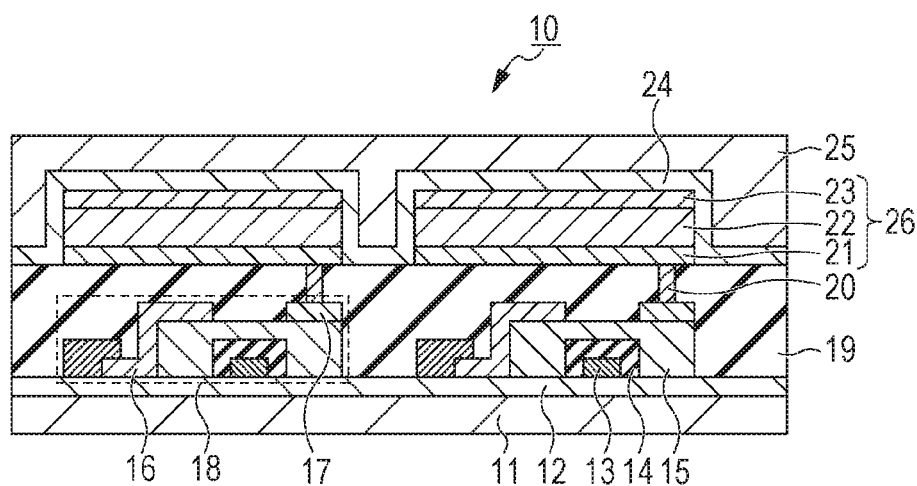
FIG. 3 is a schematic sectional view illustrating an example of a display apparatus including an organic light-emitting element according to one embodiment of the present disclosure and a transistor electrically connected to the organic light-emitting element.

Next, a display apparatus according to one embodiment will be described with reference to the drawings. FIG. 3 is a schematic sectional view illustrating an example of a display apparatus including an organic light-emitting element and a TFT element connected to the organic light-emitting element. The TFT element is an example of an active element.

A display apparatus 10 in FIG. 3 includes a substrate 11 made of, for example, glass and a moisture-proof film 12 thereon for protecting a TFT element or an organic compound layer. Reference numeral 13 is a gate electrode 13 made of metal. Reference numeral 14 is a gate insulating film 14, and reference numeral 15 is a semiconductor layer.

The TFT element 18 includes a semiconductor layer 15, a drain electrode 16, and a source electrode 17. An insulating film 19 is disposed on the TFT element 18. An anode 21 constituting an organic light-emitting element and the source electrode 17 are connected to each other through a contact hole 20.

The electrodes (anode, cathode) in the organic light-emitting element and the electrodes (source electrode, drain electrode) in the TFT need not necessarily be electrically connected to each other in the manner illustrated in FIG. 3. It is only required that either the anode or the cathode be electrically connected to either the source electrode or the drain electrode in the TFT element.

Although the organic compound layer is illustrated as a single layer in the display apparatus 10 in FIG. 3, the organic compound layer 22 may be composed of multiple layers. A first protective layer 24 and a second protective layer 25 for preventing deterioration of the organic light-emitting element are disposed over the cathode 23.

Although a transistor is used as a switching element in the display apparatus 10 in FIG. 3, an MIM element may be used as a switching element instead.

The transistor used in the display apparatus 10 in FIG. 3 may not only be a transistor obtained using a single-crystal silicon wafer but also a thin-film transistor including a substrate and an active layer on an insulating surface of the substrate. The active layer may be made of, for example, single-crystal silicon, non-single-crystal silicon such as amorphous silicon or microcrystalline silicon, or a non-single-crystal oxide semiconductor such as indium zinc oxide or indium gallium zinc oxide. The thin-film transistor is also referred to as a TFT element.

The transistor in the display apparatus 10 in FIG. 3 may be formed in a substrate such as a Si substrate. The phrase "formed in a substrate" means producing a transistor by processing a substrate itself, such as a Si substrate. That is, having a transistor in a substrate can also mean that a substrate and a transistor are integral with each other.

Whether the transistor is provided in a substrate is selected according to the level of resolution. For example, in the case of 1-inch size and about a QVGA resolution, the transistor may be disposed in a Si substrate.

Figure 4:
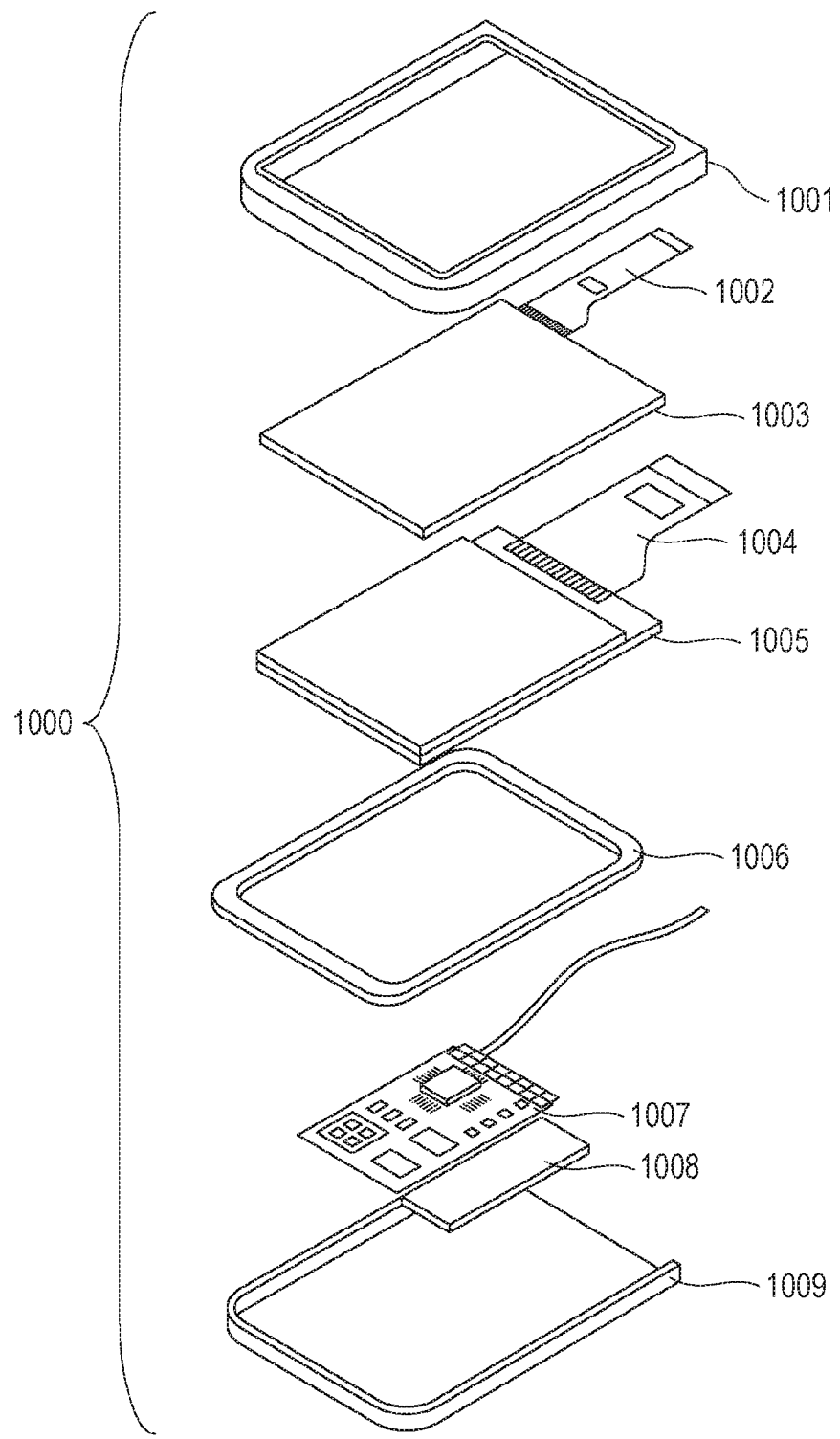
FIG. 4 is a schematic view illustrating an example of a display apparatus according to one embodiment of the present disclosure.

FIG. 4 is a schematic view illustrating an example of a display apparatus according to this embodiment. A display apparatus 1000 may include an upper cover 1001, a lower cover 1009, and a touch panel 1003, a display panel 1005, a frame 1006, a circuit board 1007, and a battery 1008 disposed between the upper cover 1001 and the lower cover 1009. Flexible print circuits (FPCs) 1002 and 1004 are connected to the touch panel 1003 and the display panel 1005, respectively. A transistor is printed on the printed circuit board 1007. The battery 1008 may be omitted if the display apparatus is not a mobile device. If the display apparatus is a mobile device, the battery 1008 need not necessarily be disposed at this position.

The display apparatus according to this embodiment may be used in a display unit of an image pickup apparatus that includes an optical unit including a plurality of lenses and an image capture element that receives light that has passed through the optical unit. The image pickup apparatus may include a display unit that displays information acquired by the image capture element. The display unit may be exposed to the outside of the image pickup apparatus or disposed in a viewfinder. The image pickup apparatus may be a digital camera or a digital camcorder.

Figure 5A:
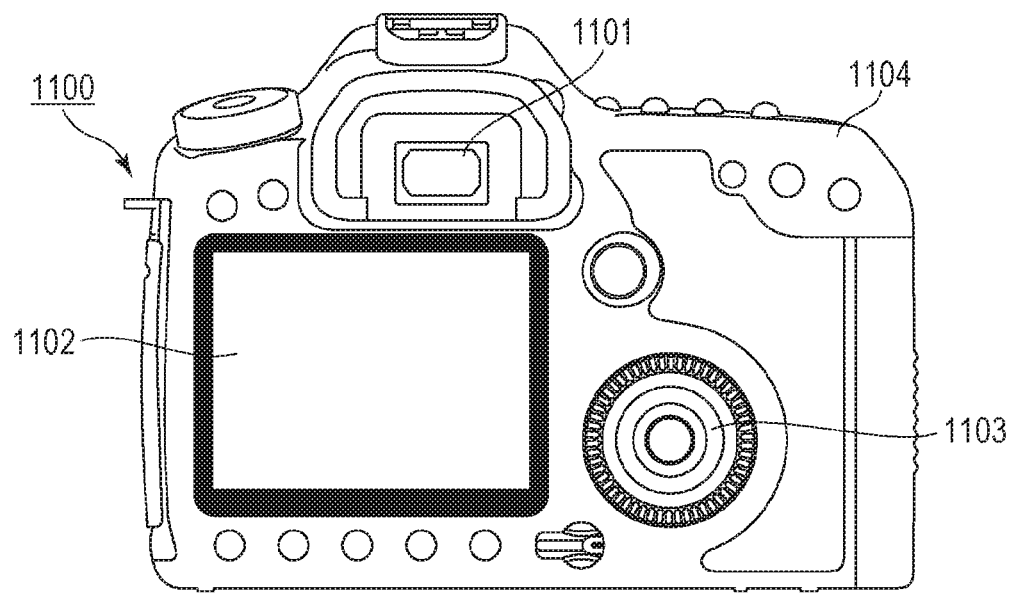
FIG. 5A is a schematic view illustrating an example of an image pickup apparatus according to one embodiment of the present disclosure.

FIG. 5A is a schematic view illustrating an example of an image pickup apparatus according to this exemplary embodiment. An image pickup apparatus 1100 may include a viewfinder 1101, a rear display 1102, an operation unit 1103, and a housing 1104. The viewfinder 1101 may include the display apparatus according to this embodiment. In this case, the display apparatus may display not only an image to be captured but also environmental information, image capture instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Thus, the display apparatus including the organic light-emitting element according to one embodiment of the present disclosure may be used. This is because the organic light-emitting element has a high response speed. The display apparatus including the organic light-emitting element is more suitable for use than such apparatuses and liquid crystal display apparatuses that are required to have high display speeds.

The image pickup apparatus 1100 includes an optical unit (not illustrated). The optical unit includes a plurality of lenses and focuses an image on the image capture element accommodated in the housing 1104. By adjusting the relative positions of the plurality of lenses, the focal point can be adjusted. This operation can also be performed automatically.

The display apparatus according to this embodiment may include red, green, and blue color filters. The red, green, and blue color filters may be disposed in a delta arrangement or a stripe arrangement.

The display apparatus according to this embodiment may be used in a display unit of a mobile terminal. In this case, the display apparatus may have both a display function and an operating function. Examples of mobile terminals include cellular phones such as smart phones, tablets, and head mount displays.

Figure 5B:
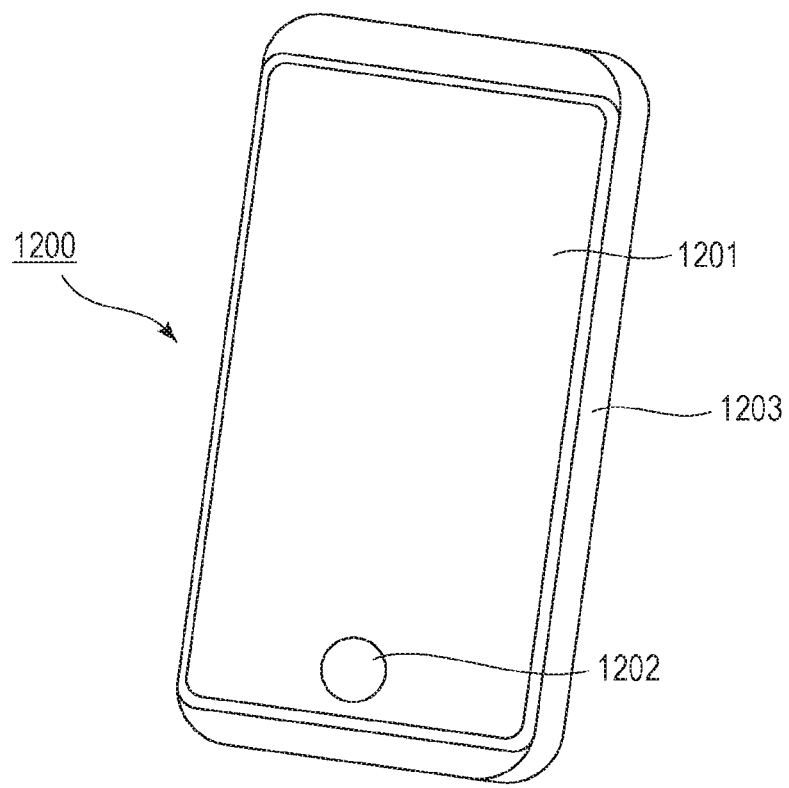
FIG. 5B is a schematic view illustrating an example of a mobile device according to one embodiment of the present disclosure.

FIG. 5B is a schematic view illustrating an example of an electronic device according to this embodiment. An electronic device 1200 includes a display unit 1201, an operation unit 1202, and a housing 1203. The housing 1203 may include a circuit, a printed board including the circuit, a battery, and a communication unit. The operation unit 1202 may be a button or a touch-sensitive response unit. The operation unit may be a biometric recognition unit that, for example, releases a lock through recognition of fingerprints. An electronic device including a communication unit can also be referred to as a communication device.

Figure 6A:
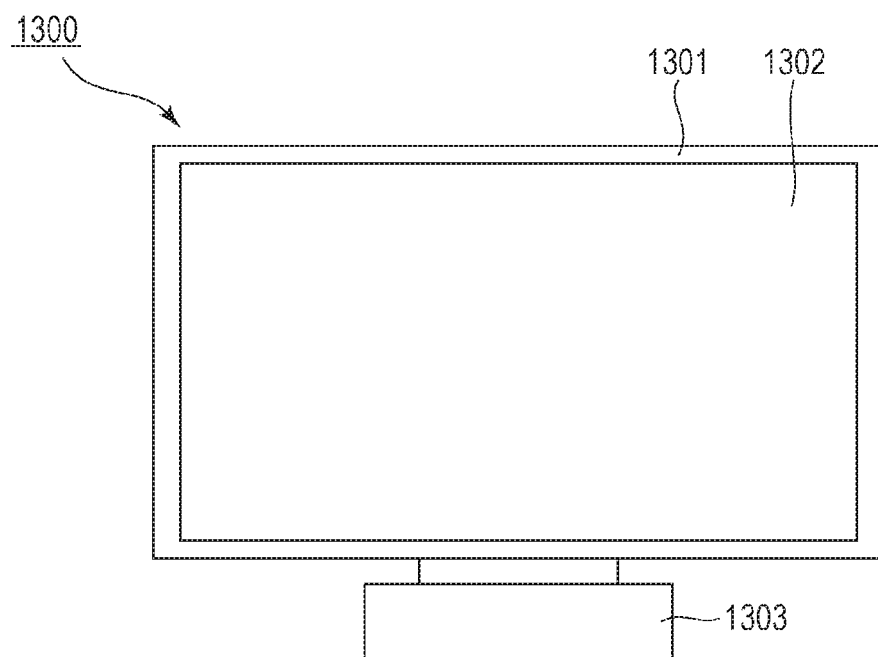
FIG. 6A is a schematic view illustrating an example of a display apparatus according to one embodiment of the present disclosure.
Figure 6B:
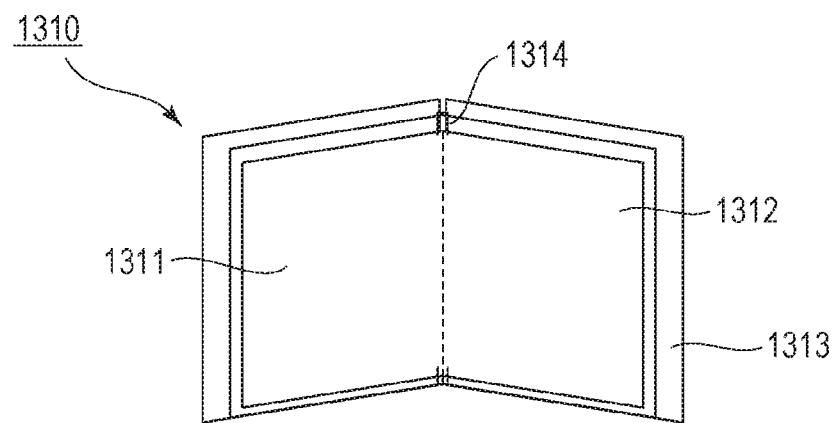
FIG. 6B is a schematic view illustrating an example of a foldable display apparatus.

FIGS. 6A and 6B are schematic views illustrating examples of display apparatuses according to this embodiment. FIG. 6A illustrates a display apparatus, for example, a television monitor or a PC monitor. A display apparatus 1300 includes a frame 1301 and a display unit 1302. The light-emitting apparatus according to this embodiment may be used in the display unit 1302.

The display apparatus 1300 includes a base 1303 that supports the frame 1301 and the display unit 1302. The base 1303 need not necessarily be in the form illustrated in FIG. 6A. The lower side of the frame 1301 may serve as a base.

The frame 1301 and the display unit 1302 may be curved. The radius of curvature may be 5,000 mm or more and 6,000 mm or less.

FIG. 6B is a schematic view illustrating another example of a display apparatus according to this embodiment. A display apparatus 1310 in FIG. 6B is configured to be foldable and is what is called a foldable display apparatus. The display apparatus 1310 includes a first display unit 1311, a second display unit 1312, a housing 1313, and a bending point 1314. The first display unit 1311 and the second display unit 1312 may each include the light-emitting apparatus according to this embodiment. The first display unit 1311 and the second display unit 1312 may be a seamless, monolithic display apparatus. The first display unit 1311 and the second display unit 1312 can be divided by the bending point. The first display unit 1311 and the second display unit 1312 may display different images, or the first and second display units may together display a single image.

Figure 7A:
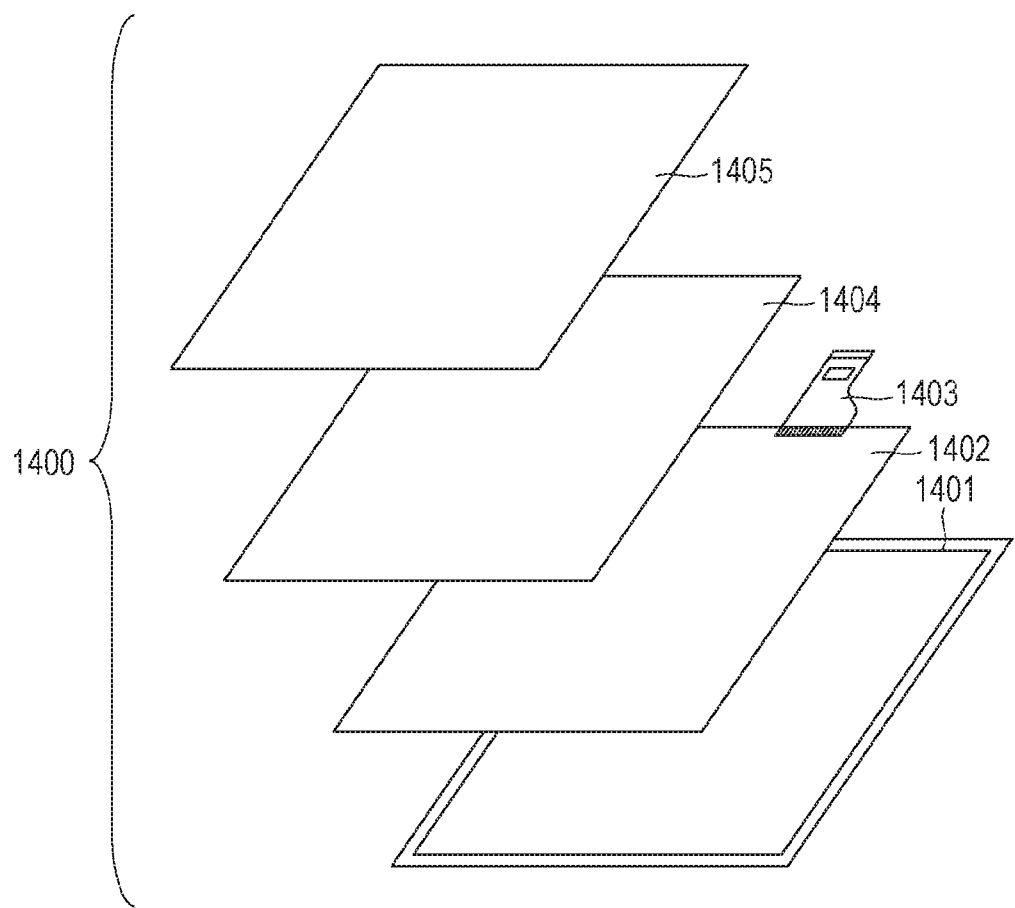
FIG. 7A is a schematic view illustrating an example of a lighting apparatus according to one embodiment of the present disclosure.

FIG. 7A is a schematic view illustrating an example of a lighting apparatus according to this embodiment. A lighting apparatus 1400 may include a housing 1401, a light source 1402, a circuit board 1403, an optical film 1404, and a light diffusion unit 1405. The light source may include the organic light-emitting element according to this embodiment. The optical filter may be a filter for improving the color rendering properties of the light source. The light diffusion unit effectively diffuses light from the light source and helps the light reach a wide region for, for example, lighting up. The optical filter and the light diffusion unit may be disposed on the light-emitting side of the lighting apparatus. Optionally, a cover may be disposed at an outermost portion.

The lighting apparatus is, for example, an apparatus that lights a room. The lighting apparatus may emit light of cool white, day white, or any other color from blue to red. The lighting apparatus may include a modulation circuit that modulates the light. The lighting apparatus may include the organic light-emitting element of the present disclosure and a power supply circuit connected thereto. The power supply circuit is a circuit that converts AC voltage to DC voltage. Cool white has a color temperature of 4200 K, and day white has a color temperature of 5000 K. The lighting apparatus may include a color filter.

The lighting apparatus according to this embodiment may also include a heat dissipation unit. The heat dissipation unit dissipates heat out of the apparatus and may be made of, for example, a metal of high specific heat or liquid silicon.

Figure 7B:
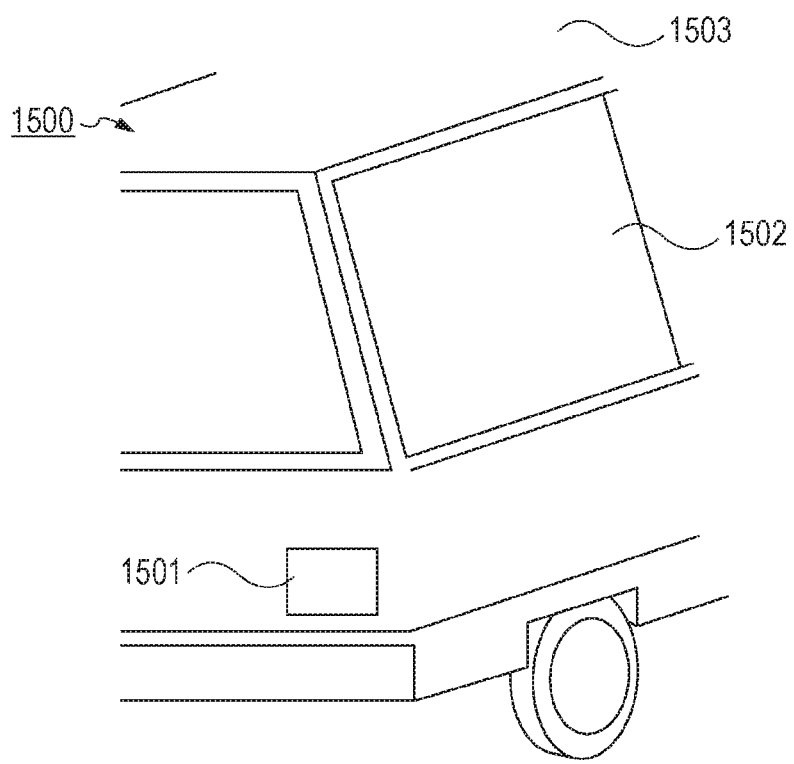
FIG. 7B is a schematic view illustrating an automobile that is an example of a moving object according to one embodiment of the present disclosure.

FIG. 7B is a schematic view of an automobile that is an example of a moving object according to this embodiment. The automobile includes a tail lamp that is an example of a lighting fixture. An automobile 1500 includes a tail lamp 1501, and the tail lamp may be configured to be turned on in response to, for example, brake operation.

The tail lamp 1501 may include the organic light-emitting element according to this embodiment. The tail lamp may include a protective member that protects the organic EL element. The protective member may be made of any material that is strong to some extent and transparent, preferably a polycarbonate or the like. A mixture of a polycarbonate with, for example, a furandicarboxylic acid derivative or an acrylonitrile derivative may be used.

The automobile 1500 may include a car body 1503 and a window 1502 attached thereto. The window may be a transparent display unless it is a window for checking the front and rear of an automobile. The transparent display may include the organic light-emitting element according to this embodiment. In this case, components, such as electrodes, of the organic light-emitting element are made of transparent materials.

The moving object according to this embodiment may be, for example, a ship, an aircraft, or a drone. The moving object may include a body and a lighting fixture disposed on the body. The lighting fixture may emit light for allowing the position of the body to be recognized. The lighting fixture includes the organic light-emitting element according to this embodiment.

The organic light-emitting element according to this embodiment has an emission luminance that is controlled by a TFT, which is an example of a switching element. Disposing a plurality of the organic light-emitting elements in a plane enables a display of an image with different emission luminances. The switching element according to this embodiment need not necessarily be a TFT and may be a transistor formed of low-temperature polysilicon or an active matrix driver formed on a substrate such as a Si substrate. The active matrix driver may also be formed in the substrate. This is selected according to the level of resolution. For example, in the case of 1-inch size and about a QVGA resolution, the organic light-emitting element may be disposed on a Si substrate. Driving the display apparatus including the organic light-emitting element according to this embodiment enables a stable display with high image quality over a long period of time.

EXAMPLES

The present disclosure will now be described with reference to Examples, but the present disclosure is not limited to these Examples.

Example 1: Synthesis of Exemplary Compound A10

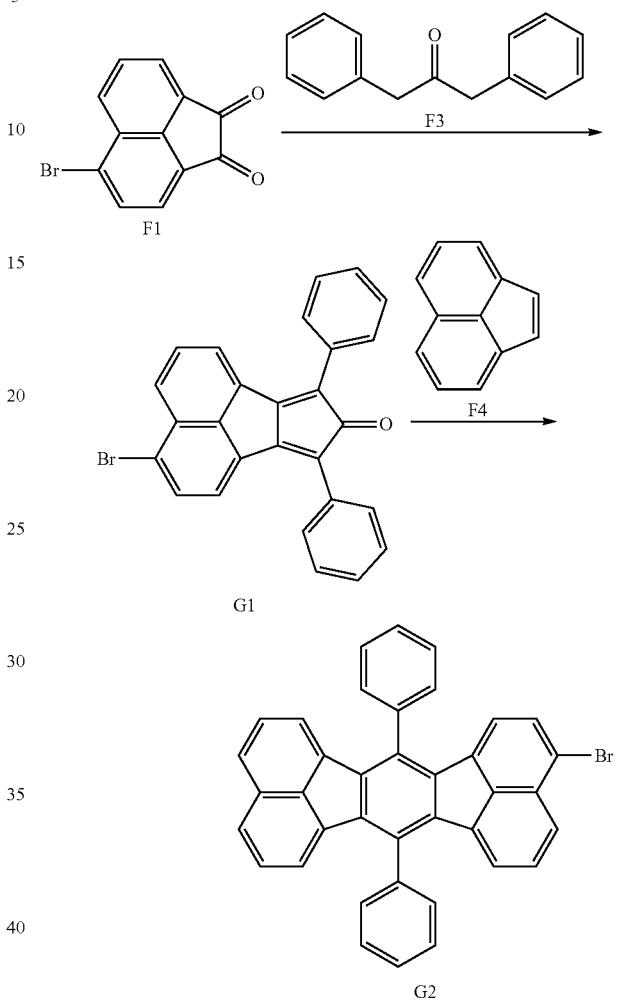

(1) Synthesis of Compound G2

The following reagents and solvent were loaded into a 300 ml recovery flask.
Compound F1: 13.1 g (50 mmol)
Compound F3: 10.5 g (50 mmol)
Ethanol: 200 ml Next, the reaction solution was heated to 60° C. under a stream of nitrogen, and then 20 ml of a 5M aqueous sodium hydroxide solution was added dropwise. After completion of the addition, the resulting solution was heated to 80° C., stirred for 2 hours, and then cooled to form a precipitate. The precipitate was filtered, and the residue was washed with water and ethanol and then dried by heating at 80° C. under reduced pressure to obtain 18.7 g of G1 as a dark green solid (yield: 86%).

Next, 4.35 g (10 mmol) of G1, 1.52 g (10 mmol) of F4, 100 ml of o-xylene were placed in a 200 ml recovery flask, and stirring was performed for 8 hours under heating at reflux. After cooling, the resulting solution was concentrated to obtain a dark brown liquid. The liquid was purified by column chromatography (toluene/heptane=2:3) and then recrystallized from chloroform/methanol to obtain 4.68 g of G2 as a yellow crystal (yield: 84%).

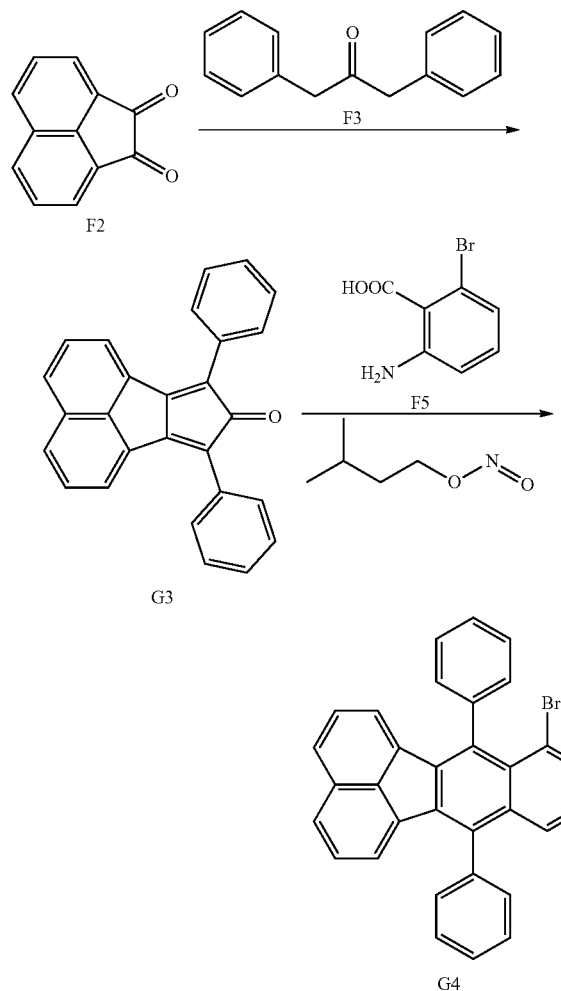

(2) Synthesis of Compound G4

The following reagents and solvent were loaded into a 300 ml recovery flask.
Compound F2: 9.1 g (50 mmol)
Compound F3: 10.5 g (50 mmol)
Ethanol: 200 ml Next, the reaction solution was heated to 60° C. under a stream of nitrogen, and then 20 ml of a 5M aqueous sodium hydroxide solution was added dropwise. After completion of the addition, the resulting solution was heated to 80° C., stirred for 2 hours, and then cooled to form a precipitate. The precipitate was filtered, and the residue was washed with water and ethanol and then dried by heating at 80° C. under reduced pressure to obtain 15.7 g of G3 as a dark green solid (yield: 88%).

Next, 7.12 g (20 mmol) of G3, 5.18 g (24 mmol) of F5, and 100 ml of toluene were placed in a 200 ml recovery flask and heated to 80° C. Thereafter, 2.80 g (24 mmol) of isoamyl nitrite was gradually added dropwise, and then stirring was performed at 110° C. for 3 hours. After cooling, the mixture was washed twice with 200 ml of water. The organic layer was washed with saturated saline and dried over magnesium sulfate. The solution was then filtered, and the filtrate was then concentrated to obtain a dark brown liquid. The liquid was purified by column chromatography (toluene/heptane=2:3) and then recrystallized from chloroform/methanol to obtain 7.74 g of G4 (isomer mixture) as a yellow crystal (yield: 80%).

(3) Synthesis of Compound G5

The following reagents and solvent were loaded into a 200 ml recovery flask.
Compound G4: 4.84 g (10 mmol)
Pd(PPh$_3$)$_2$Cl$_2$: 0.50 g (1 mmol)
1,8-Diazabicyclo[5.4.0]undec-7-ene: 4.56 g (30 mmol)
DMF: 80 ml Next, the reaction solution was heated to 150° C. under a stream of nitrogen and stirred for 4 hours. After the resulting solution was cooled, 60 ml of methanol was added to form a precipitate. The precipitate was then filtered to obtain a yellow solid. The solid was purified by column chromatography (chloroform/heptane=1:4) and then recrystallized from chloroform/methanol to obtain 2.78 g of compound G5 as a yellow crystal (yield: 69%).

(4) Synthesis of Compound G6

The following reagents and solvent were loaded into a 200 ml recovery flask.
Compound G5: 2.4 g (6 mmol)
N-Bromosuccinimide: 1.07 g (6 mmol)
Acetonitrile: 100 ml Next, the reaction solution was heated to 60° C. under a stream of nitrogen and stirred at this temperature (60° C.) for 8 hours. After the solution was cooled and concentrated, the resulting solid was purified by column chromatography (chloroform/heptane=1:4) and then recrystallized twice from chloroform/methanol to obtain 2.43 g of compound G6 as a yellow crystal (yield: 84%).

(5) Synthesis of Compound G7

The following reagents and solvent were loaded into a 100 ml recovery flask.
Compound G6: 1.93 g (4 mmol)
Triethylamine: 1.21 g (12 mmol)
Pd(PPh$_3$)$_2$Cl$_2$: 0.056 g (0.08 mmol)
4,4,5,5-Tetramethyl-1,3,2-dioxaborolane: 1.54 g (12 mmol)
Toluene: 30 ml Next, the reaction solution was stirred under heating at reflux for 4 hours under a stream of nitrogen. After the resulting solution was cooled, 5 ml of methanol was added, and then the solution was filtered. The filtrate was concentrated to obtain a green solid. The solid was washed by dispersion with methanol and then purified by column chromatography (chloroform/heptane=1:2) to obtain 1.61 g of compound G7 as a yellow crystal (yield: 76%).

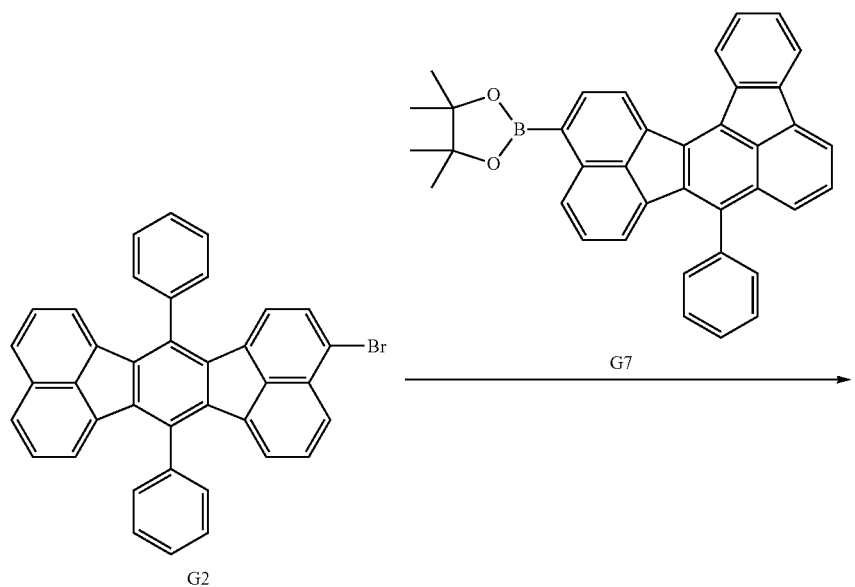

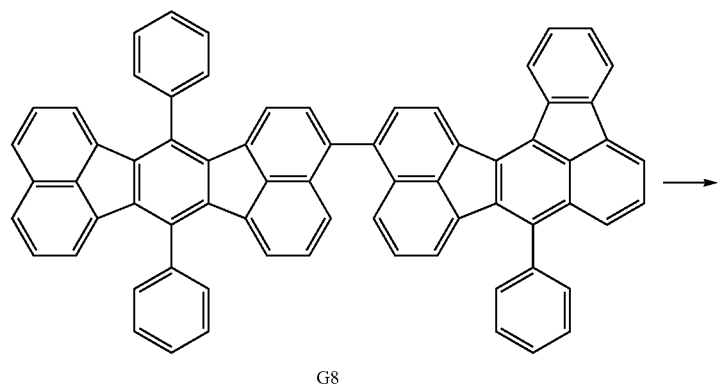

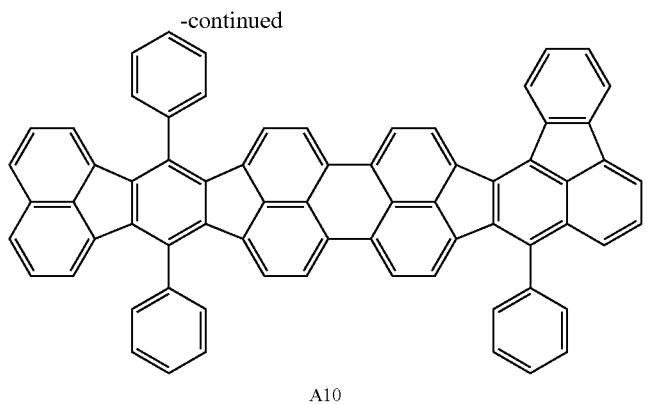

A10

(6) Synthesis of Compound G8

The following reagents and solvents were loaded into a 50 ml recovery flask.
Compound G2: 1.11 g (2 mmol)
Compound G7: 1.06 g (2 mmol)
Pd(PPh$_3$)$_4$: 0.04 g
Toluene: 20 ml
Ethanol: 8 ml
2M-Aqueous sodium carbonate solution: 20 ml Next, the reaction solution was heated to 80° C. under a stream of nitrogen and stirred at this temperature (80° C.) for 8 hours. After completion of the reaction, ethanol was added to precipitate a crystal. The crystal was then separated by filtration and washed by dispersion sequentially with water, ethanol, and heptane. Next, the crystal obtained was dissolved by heating in chlorobenzene, filtered hot, and then recrystallized to obtain 1.32 g of compound G8 as a green crystal (yield: 75%).

(7) Synthesis of Exemplary Compound A10

The following reagent and solvents were loaded into a 300 ml reaction vessel.
Compound G8: 0.88 g (1 mmol)
Trifluoroacetic acid: 6 ml
Methylene chloride: 60 ml Next, the following reagent was placed in the reaction vessel in a water bath.
BF$_3$.OEt: 2 ml Next, the reaction solution was stirred for 10 minutes, and then 0.47 g of DDQ (2,3-dichloro-5,6-dicyano-p-benzoquinone, 2.1 mmol) was added. Next, the reaction solution was stirred for 10 minutes, and then 0.39 g (2.1 mmol) of ferrocene was added in a water bath at 20° C. After stirring for 5 minutes, 60 ml of methanol was added. The resulting red precipitate was filtered to obtain a red solid. Next, the solid was dissolved in chlorobenzene and recrystallized from heptane to obtain 0.80 g of A10 as a red crystal (yield: 90%).

The purity of this compound was determined to be 99% or more by high-performance liquid chromatography (HPLC).

The emission spectrum of a toluene solution of exemplary compound A10 at a concentration of 1×10$^{-5}$ mol/L was measured by photoluminescence spectroscopy at an excitation wavelength of 360 nm by using an F-4500 manufactured by Hitachi, Ltd. The spectrum showed a maximum intensity at 616 nm.

Exemplary compound A10 was subjected to mass spectrometry using MALDI-TOF-MS (Autoflex LRF manufactured by Bruker Corporation).
MALDI-TOF-MS
Measured value: m/z=876
Calculated value: C$_{70}$H$_{36}$=876

Example 2: Synthesis of Exemplary Compound A16

Exemplary compound A16 was obtained in the same manner as in Example 1 except that compound G9 shown below was used in place of compound F3 in (1) of Example 1.

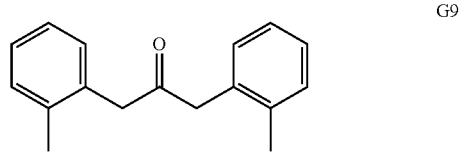 [SMILES: Cc1ccccc1CC(=O)Cc1ccccc1C]

G9

The purity of the compound obtained was determined by HPLC to be 98% or more.

Exemplary compound A16 was further subjected to mass spectrometry using MALDI-TOF-MS (Autoflex LRF manufactured by Bruker Corporation).
MALDI-TOF-MS
Measured value: m/z=904
Calculated value: C$_{72}$H$_{40}$=904

Example 3: Synthesis of Exemplary Compound A17

Exemplary compound A17 was obtained in the same manner as in Example 1 except that compound G10 shown below was used in place of compound F3 in (1) of Example 1.

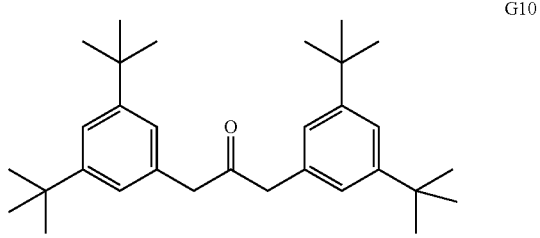 [SMILES: CC(C)(C)c1cc(CC(=O)Cc2cc(C(C)(C)C)cc(C(C)(C)C)c2)cc(C(C)(C)C)c1]

G10

The purity of the compound obtained was determined by HPLC to be 98% or more.

Exemplary compound A17 was further subjected to mass spectrometry using MALDI-TOF-MS (Autoflex LRF manufactured by Bruker Corporation).

MALDI-TOF-MS
Measured value: m/z=1100
Calculated value: $C_{86}H_{68}$=1100

Example 4: Synthesis of Exemplary Compound A18

Exemplary compound A18 was obtained in the same manner as in Example 1 except that compound G11 shown below was used in place of compound F3 in (1) of Example 1.

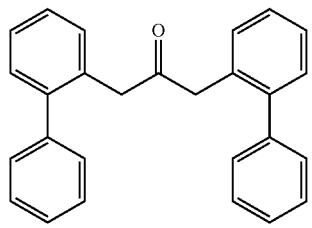

G11

The purity of the compound obtained was determined by HPLC to be 98% or more.

Exemplary compound A18 was further subjected to mass spectrometry using MALDI-TOF-MS (Autoflex LRF manufactured by Bruker Corporation).

MALDI-TOF-MS
Measured value: m/z=1028
Calculated value: $C_{82}H_{44}$=1028

Example 5: Synthesis of Exemplary Compound A21

Exemplary compound A21 was obtained in the same manner as in Example 1 except that compound G12 shown below was used in place of compound F3 in (2) of Example 1.

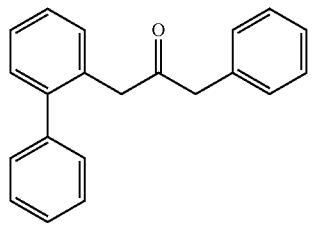

G12

The purity of the compound obtained was determined by HPLC to be 98% or more.

Exemplary compound A21 was further subjected to mass spectrometry using MALDI-TOF-MS (Autoflex LRF manufactured by Bruker Corporation).

MALDI-TOF-MS
Measured value: m/z=951
Calculated value: $C_{82}H_{44}$=951

Example 6: Synthesis of Exemplary Compound A23

Exemplary compound A23 was obtained in the same manner as in Example 1 except that compound G11 was used in place of compound F3 in (1) of Example 1 and compound G12 was used in place of compound F3 in (2) of Example 1.

The purity of the compound obtained was determined by HPLC to be 98% or more.

Exemplary compound A23 was further subjected to mass spectrometry using MALDI-TOF-MS (Autoflex LRF manufactured by Bruker Corporation).

MALDI-TOF-MS
Measured value: m/z=1042
Calculated value: $C_{88}H_{48}$=1042

Example 7: Synthesis of Exemplary Compound B2

Exemplary compound B2 was obtained in the same manner as in Example 1 except that compound G13 shown below was used in place of compound F3 in (1) of Example 1.

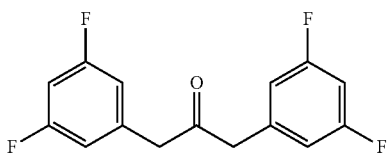

G13

The purity of the compound obtained was determined by HPLC to be 98% or more.

Exemplary compound B2 was further subjected to mass spectrometry using MALDI-TOF-MS (Autoflex LRF manufactured by Bruker Corporation).

MALDI-TOF-MS
Measured value: m/z=872
Calculated value: $C_{64}H_{28}F_4$=872

Example 8: Synthesis of Exemplary Compound B9

Exemplary compound B9 was obtained in the same manner as in Example 1 except that compound G12 shown below was used in place of compound F4 in (1) of Example 1.

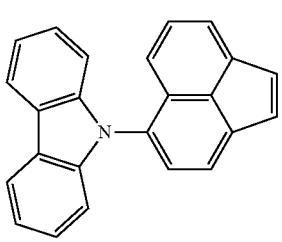

G12

The purity of the compound obtained was determined by HPLC to be 98% or more.

Exemplary compound B9 was further subjected to mass spectrometry using MALDI-TOF-MS (Autoflex LRF manufactured by Bruker Corporation).

MALDI-TOF-MS
Measured value: m/z=1055
Calculated value: $C_{83}H_{45}N$=1055

Example 9

In this Example, a bottom-emission-type organic EL element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, an ITO film was formed on a glass substrate and subjected to desired patterning to form an ITO electrode (anode). At this time, the thickness of the ITO electrode was set to 100 nm. The substrate on which the ITO electrode was formed in this manner was used as an ITO substrate in the following process. Next, organic EL layers and an electrode layer shown in Table 7 below were continuously formed on the ITO substrate by performing vacuum deposition by resistance heating in a vacuum chamber at $1.33 \times 10^{-4}$ Pa. At this time, the electrode area of the counter electrode (metal electrode layer, cathode) was set to 3 mm$^2$.

TABLE 7

| | Material | | | Thickness (nm) |
|---|---|---|---|---|
| Cathode | Al | | | 100 |
| Electron injection layer (EIL) | LiF | | | 1 |
| Electron transport layer (ETL) | ET5 | | | 30 |
| Hole blocking layer (HBL) | ET17 | | | 10 |
| Light-emitting layer (EML) | Host<br>Guest | EM1<br>A10 | Weight ratio<br>EM1:A10 =<br>99.5:0.5 | 30 |
| Electron blocking layer (EBL) | HT12 | | | 10 |
| Hole transport layer (HTL) | HT3 | | | 30 |
| Hole injection layer (HIL) | HT16 | | | 10 |

The element obtained was measured and evaluated for its characteristics. The light-emitting element had a maximum peak wavelength of 617 nm and emitted red light with a chromaticity of (X, Y)=(0.69, 0.31). The current-voltage characteristics of the organic light-emitting element were measured with a 4140B microammeter manufactured by Hewlett-Packard Company. The emission luminance of the organic light-emitting element was measured with a BM7 manufactured by TOPCON Corporation. Furthermore, a continuous driving test at a current density of 100 mA/cm$^2$ was performed to measure the time taken for a decrease in luminance to reach 5%. The time exceeded 500 hours. The measurement results are shown in Table 8.

Example 10 to 16 and Comparative Example 1

Organic light-emitting elements were produced in the same manner as in Example 9 except that the compounds in Example 9 were appropriately changed to those shown in Table 8. The elements obtained were measured and evaluated for their characteristics in the same manner as in Example 9. The measurement results are shown in Table 8.

TABLE 8

| | HIL | HTL | EBL | EML Host | Guest | HBL | ETL | E.Q.E [%] | Chromaticity coordinates of red (x, y) |
|---|---|---|---|---|---|---|---|---|---|
| Example 9 | HT16 | HT6 | HT11 | EM17 | A10 | ET12 | ET2 | 4.7 | (0.69, 0.31) |
| Example 10 | HT16 | HT6 | HT8 | EM17 | A7 | ET10 | ET2 | 4.7 | (0.68, 0.32) |
| Example 11 | HT16 | HT3 | HT11 | EM16 | A18 | ET12 | ET2 | 4.8 | (0.69, 0.31) |
| Example 12 | HT2 | HT1 | HT11 | EM18 | A21 | ET15 | ET2 | 4.8 | (0.69, 0.31) |
| Example 13 | HT15 | HT6 | HT11 | EM22 | B2 | ET13 | ET2 | 4.6 | (0.68, 0.32) |
| Example 14 | HT17 | HT6 | HT11 | EM18 | A10 | ET12 | ET3 | 4.7 | (0.69, 0.31) |
| Example 15 | HT15 | HT2 | HT11 | EM16 | A16 | ET12 | ET2 | 4.8 | (0.69, 0.31) |
| Example 16 | HT17 | HT2 | HT8 | EM17 | A1 | ET17 | ET2 | 4.6 | (0.68, 0.31) |
| Comparative Example 1 | HT16 | HT2 | HT11 | EM17 | Comparative compound (1) | ET12 | ET2 | 4.4 | (0.67, 0.33) |

Table 8 shows that the chromaticity coordinates of red in Comparative Example 1 were (0.67, 0.33). Red-light-emitting elements in which the organic compound of formula (1) was used for a red-light-emitting layer, that is, the organic light-emitting elements of Examples, and a red-light-emitting element in which comparative compound (1) was used for a red-light-emitting layer, that is, the organic light-emitting element of Comparative Example, were compared with each other. As is clear from Table 8, the organic light-emitting elements of Examples emitted longer-wavelength red light. That is, the organic light-emitting elements of Examples have chromaticity coordinates closer to those (0.71, 0.29) in BT-2020 and thus are elements having higher color reproducibility. The reason why the organic light-emitting elements of Examples emit longer-wavelength red light is that the organic compound according to one embodiment of the present disclosure emits red light at a longer wavelength.

Example 17

In this Example, a top-emission-type organic light-emitting element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film with a thickness of 40 nm was formed on a glass substrate by sputtering and patterned by photolithography to form an anode. At this time, the electrode area of the counter electrode (metal electrode layer, cathode) was set to 3 mm$^2$.

Subsequently, the cleaned substrate on which the electrode had been formed and materials were placed in a vacuum deposition apparatus (manufactured by ULVAC, Inc.). The apparatus was evacuated to $1.33 \times 10^{-4}$ Pa ($1 \times 10^{-6}$ Torr), and UV/ozone cleaning was then performed. Thereafter, layers were formed so as to be configured as shown in Table 9 below. Lastly, sealing was performed in a nitrogen atmosphere.

TABLE 9

|  | Material |  | | Thickness (nm) |
|---|---|---|---|---|
| Cathode | Mg Ag | | Weight ratio Mg:Ag = 50:50 | 10 |
| Electron injection layer (EIL) | LiF | | | 1 |
| Electron transport layer (ETL) | ET2 | | | 30 |
| Hole blocking layer (HBL) | ET12 | | | 70 |
| Second light-emitting layer (2nd EML) | Second host Second guest (blue dopant) | EM1 BD5 | Weight ratio EM1:BD5 = 99.4:0.6 | 10 |
| First light-emitting layer (1st EML) | First host First guest (red dopant) Third guest (green dopant) | EM1 A10 GD8 | Weight ratio EM1:A10:GD8 = 96.5:0.5:3.0 | 10 |

TABLE 9-continued

| | Material | Thickness (nm) |
|---|---|---|
| Electron blocking layer (EBL) | HT7 | 10 |
| Hole transport layer (HTL) | HT2 | 20 |
| Hole injection layer (HIL) | HT16 | 5 |

The element obtained was measured and evaluated for its characteristics. The element obtained exhibited good white-light emission. The chromaticity coordinates of red after transmission through an RGB color filter were estimated from the white-light emission spectrum obtained. The results are shown in Table 10 together with other Examples.

Example 18 to 23 and Comparative Example 2

Organic light-emitting elements were produced in the same manner as in Example 17 except that the compounds in Example 17 were appropriately changed to those shown in Table 10. The elements obtained were measured and evaluated for their characteristics in the same manner as in Example 17. The measurement results are shown in Table 10.

TABLE 10

| | 1st EML | | | 2nd EML | | Chromaticity |
|---|---|---|---|---|---|---|
| | First host | First guest | Third guest | Second host | Second guest | coordinates of red (x, y) |
| Example 17 | EM5 | A10 | GD9 | EM5 | BD6 | (0.69, 0.31) |
| Example 18 | EM5 | A21 | GD7 | EM1 | BD4 | (0.70, 0.30) |
| Example 19 | EM1 | A10 | GD7 | EM1 | BD7 | (0.69, 0.31) |
| Example 20 | EM5 | A1 | GD4 | EM6 | BD5 | (0.69, 0.31) |
| Example 21 | EM5 | A16 | GD2 | EM6 | BD6 | (0.69, 0.31) |
| Example 22 | EM5 | A18 | GD1 | EM1 | BD3 | (0.70, 0.31) |
| Example 23 | EM6 | A16 | GD4 | EM5 | BD1 | (0.69, 0.31) |
| Comparative Example 2 | EM5 | Comparative compound (3) | GD4 | EM5 | BD6 | (0.68, 0.32) |

Table 10 shows that the chromaticity coordinates of red in Comparative Example 2 were (0.68, 0.32). White-light-emitting elements in which the organic compound of formula (1) was used for a red-light-emitting layer, that is, the white-light-emitting elements of Examples, and a white-light-emitting element in which comparative compound (3) was used for a red-light-emitting layer, that is, the white-light-emitting element of Comparative Example, were compared with each other. As is clear from Table 10, the white-light-emitting elements of Examples emitted longer-wavelength red light. That is, the white-light-emitting elements of Examples emit red light with chromaticity coordinates closer to those (0.71, 0.29) in BT-2020 and thus have higher color reproducibility. The reason why the white-light-emitting elements of Examples emit longer-wavelength red light is that the organic compound according to one embodiment of the present disclosure emits red light at a longer wavelength.

The organic compound represented by formula (2), which is an organic compound according to one embodiment of the present disclosure, was synthesized and evaluated.

Example 24: Synthesis of Exemplary Compound C2

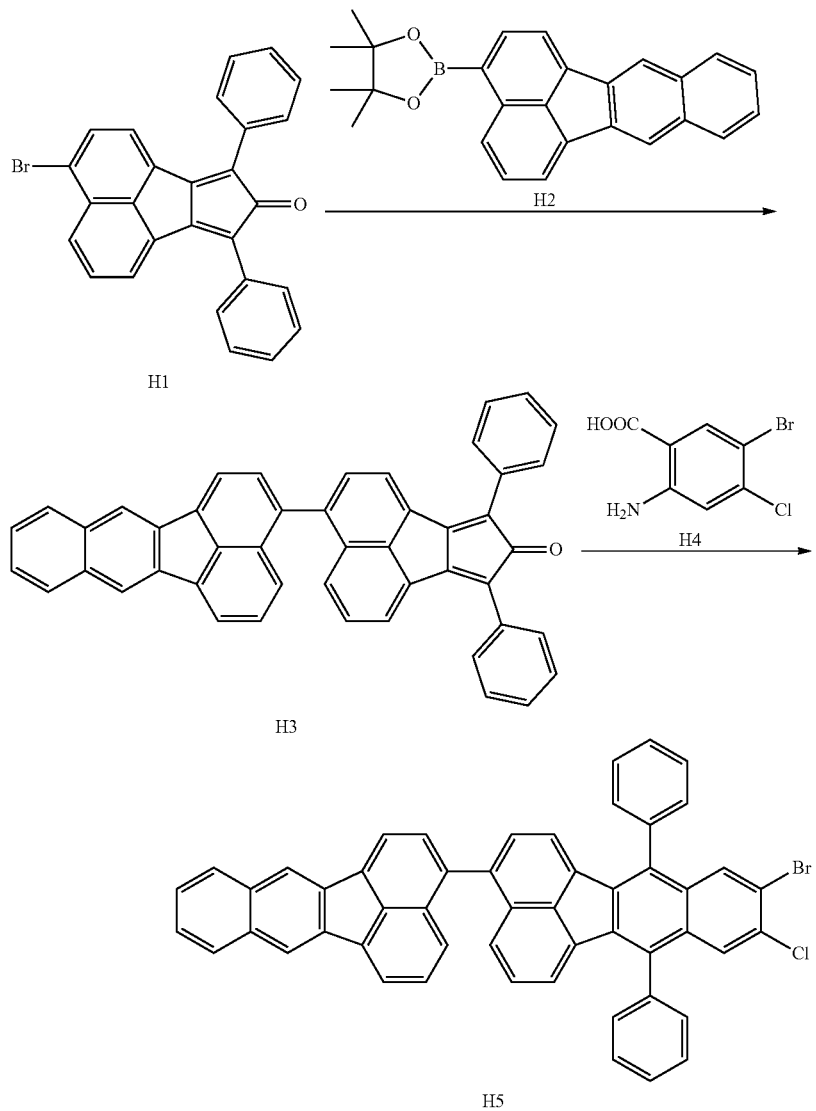

(1) Synthesis of Compound H3

The following reagents and solvents were loaded into a 200 ml recovery flask.

Compound H1: 2.00 g (4.59 mmol)
Compound H2: 1.79 g (4.73 mmol)
Pd(PPh$_3$)$_4$: 159 mg (0.14 mmol)
Toluene: 45 ml
Ethanol: 20 ml
10% Aqueous sodium carbonate solution: 25 ml Next, the reaction solution was heated to 90° C. under a stream of nitrogen and stirred at this temperature (90° C.) for 5 hours. After completion of the reaction, the resulting solution was extracted with toluene and water and then concentrated. The resulting product was purified by silica gel column chromatography (heptane:toluene=2:1) and then washed by dispersion with heptane/ethanol to obtain 2.01 g of a dark green compound H3 (yield: 72%).

(2) Synthesis of Compound H5

The following reagents and solvent were loaded into a 100 ml recovery flask.

Compound H3: 2.00 g (3.30 mmol)
Compound H4: 991 mg (4.00 mmol)
Isoamyl nitrite: 0.66 ml (4.95 mmol)
Toluene: 35 ml Next, the reaction solution was heated to 105° C. under a stream of nitrogen and stirred at this temperature (105° C.) for 2 hours. Furthermore, 330 mg (1.32 mmol) of compound H4 and 0.18 ml (1.32 mmol) of isoamyl nitrite were added, and stirring was performed for 2 hours. After completion of the reaction, the resulting solution was extracted with toluene and water and then concentrated. The resulting product was purified by silica gel column chromatography (heptane:toluene=4:1) and then washed by dispersion with heptane/ethanol to obtain 1.82 g of a yellow compound H5 (yield: 77%).

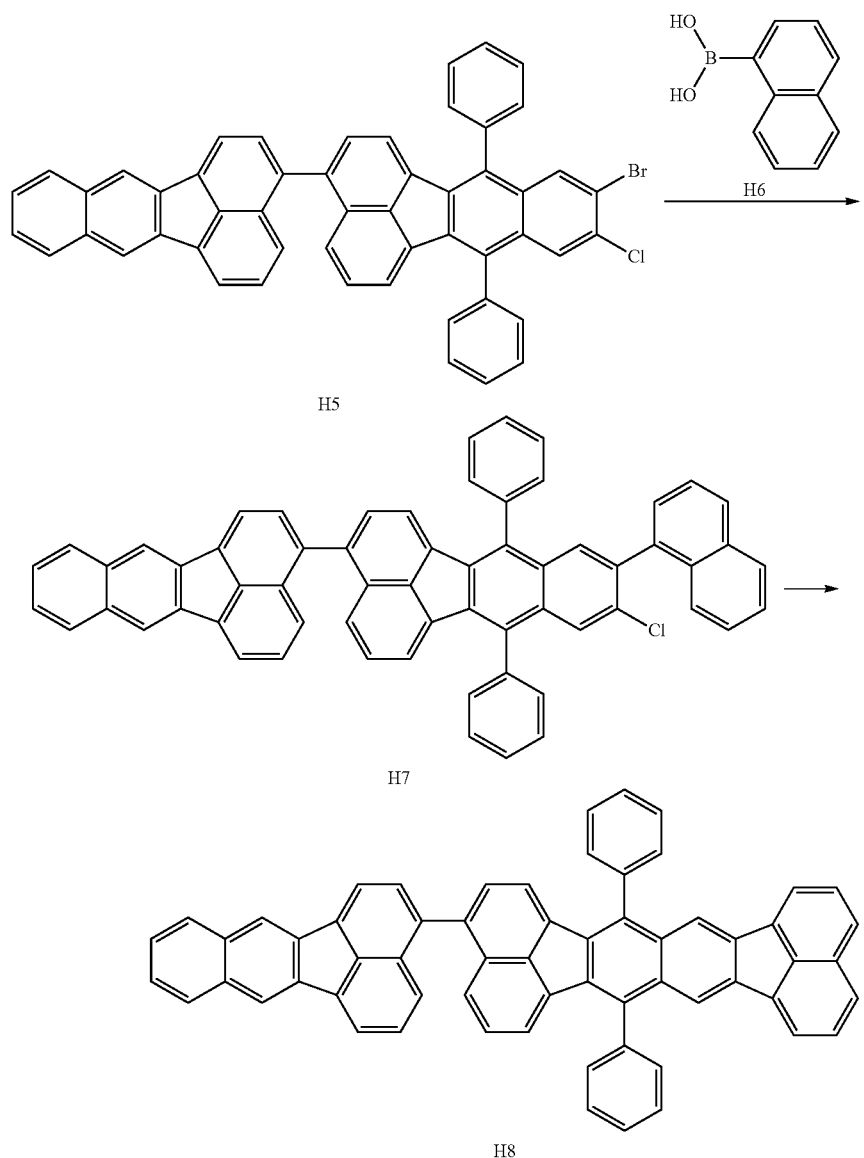

(3) Synthesis of Compound H7

The following reagents and solvents were loaded into a 100 ml recovery flask.
Compound H5: 1.80 g (2.51 mmol)
Compound H6: 474 mg (2.76 mmol)
Pd(PPh$_3$)$_4$: 87 mg (0.075 mmol)
Cesium carbonate: 3.27 g (10.0 mmol)
Toluene: 25 ml
Ethanol: 10 ml
Water: 15 ml Next, the reaction solution was heated to 90° C. under a stream of nitrogen and stirred at this temperature (90° C.) for 4 hours. After completion of the reaction, the resulting solution was extracted with toluene and water and then concentrated. The resulting product was purified by silica gel column chromatography (heptane:toluene=4:1) and then washed by dispersion with heptane/ethanol to obtain 1.82 g of a yellow compound H7 (yield: 89%).

(5) Synthesis of Compound H8

The following reagents and solvent were loaded into a 20 ml recovery flask.
Compound H7: 1.80 g (2.21 mmol)
Pd(dba)$_2$: 381 mg (0.66 mmol)
P(Cy)$_3$ (tricyclohexylphosphine): 384 mg (1.37 mmol)
DBU (diazabicycloundecene): 1.32 ml (8.83 mmol)
DMAc: 30 ml Next, the reaction solution was heated to 170° C. under a stream of nitrogen and stirred at this temperature (170° C.) for 5 hours. After completion of the reaction, methanol was added to precipitate a crystal. The crystal was then separated by filtration and washed by dispersion sequentially with water, methanol, ethanol, and heptane. Next, the yellow crystal obtained was purified by silica gel column chromatography (heptane:chloroform=2:1) and then washed by dispersion with heptane/ethanol to obtain 1.43 g of a yellow compound H8 (yield: 83%).

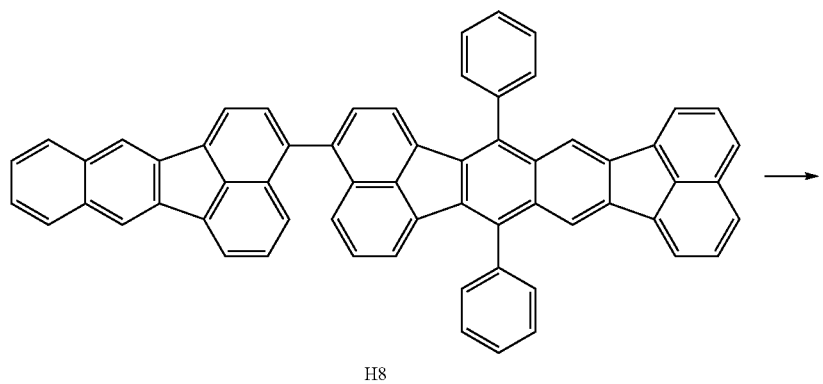

H8

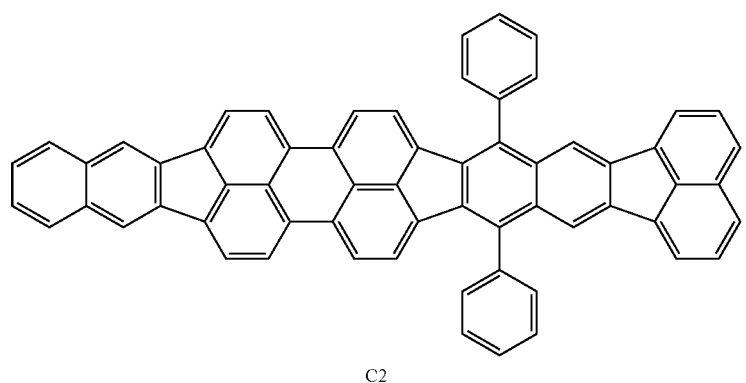

C2

(6) Synthesis of Exemplary Compound C2

The following reagents and solvent were loaded into a 20 ml recovery flask.

Compound E8: 300 mg (0.385 mmol)
t-BuOK: 1.73 g (15.4 mmol)
DBU (diazabicycloundecene): 4.61 ml (30.8 mmol)
Diethylene glycol dimethyl ether: 18 ml Next, the reaction solution was heated to 180° C. under a stream of nitrogen and stirred at this temperature (180° C.) for 10 hours. After completion of the reaction, water was added to precipitate a crystal. The crystal was then separated by filtration and washed by dispersion sequentially with water, methanol, ethanol, and heptane. Next, the deep purple solid obtained was dissolved in chlorobenzene at 130° C. Alumina was added thereto, and a heat adsorption treatment was performed. The resulting product was filtered hot, concentrated, and washed by dispersion with acetone/heptane to obtain 233 mg of a deep purple exemplary compound C2 (yield: 78%).

The emission spectrum of a toluene solution of exemplary compound C2 at a concentration of $1 \times 10^{-5}$ mol/L was measured by photoluminescence spectroscopy at an excitation wavelength of 360 nm by using an F-4500 manufactured by Hitachi, Ltd. The spectrum showed a maximum intensity at 603 nm.

Exemplary compound C2 was subjected to mass spectrometry using MALDI-TOF-MS (Autoflex LRF manufactured by Bruker Corporation).

MALDI-TOF-MS
Measured value: m/z=777
Calculated value: $C_{62}H_{32}$=776

Examples 25 to 45: Synthesis of Exemplary Compounds

Exemplary compounds shown in Tables 11 to 13 were synthesized in the same manner as in Example 24 except that the raw materials E1, E2, and E6 in Example 24 were replaced with raw material 1, raw material 2, and raw material 3, respectively. Measured values (m/z) of mass spectrometry determined in the same manner as in Example 24 are also shown in the Tables.

TABLE 11
| Example | Exemplary compound |
|---|---|
| 25 | 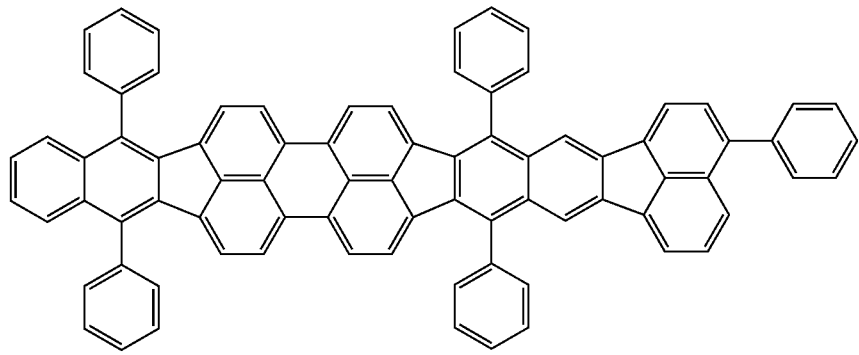<br>C4 |
| 26 | 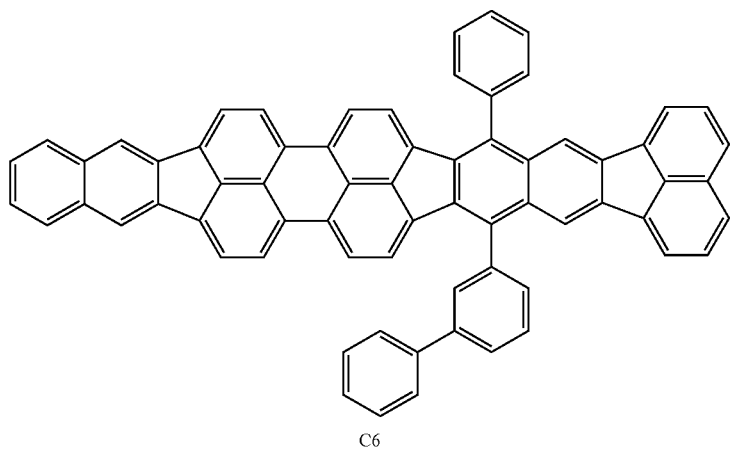 [SMILES: c1ccc(-c2cccc(-c3c4cc5c(cc4c(-c4ccccc4)c4c6ccc7c8ccc9c%10c(ccc(c%11ccc(c34)c6c7%11)c%108)-c3cc4ccccc4cc3-9)c3cccc4cccc5c43)c2)cc1 ; "C6"]<br>C6 |
| 27 | 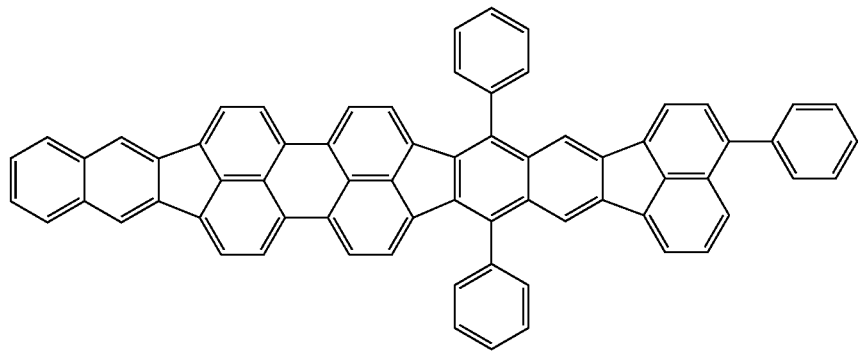<br>C7 |

TABLE 11-continued
| | |
|---|---|
| 28 | 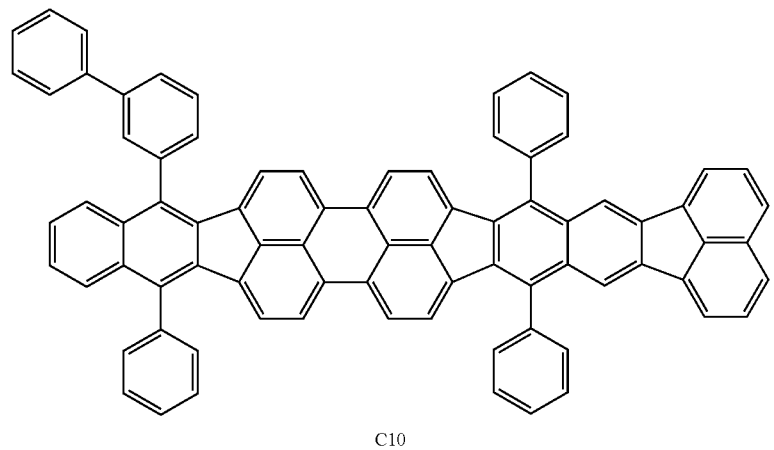<br>C10 |
| 29 | 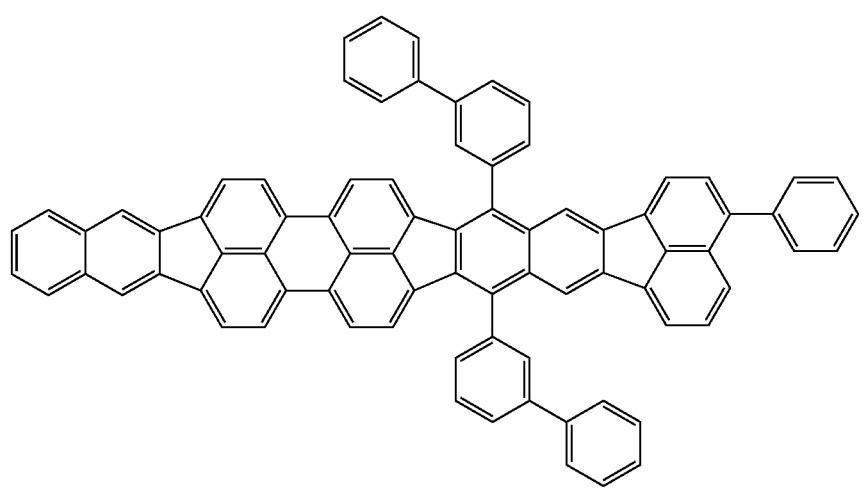<br>C11 |
| 30 | 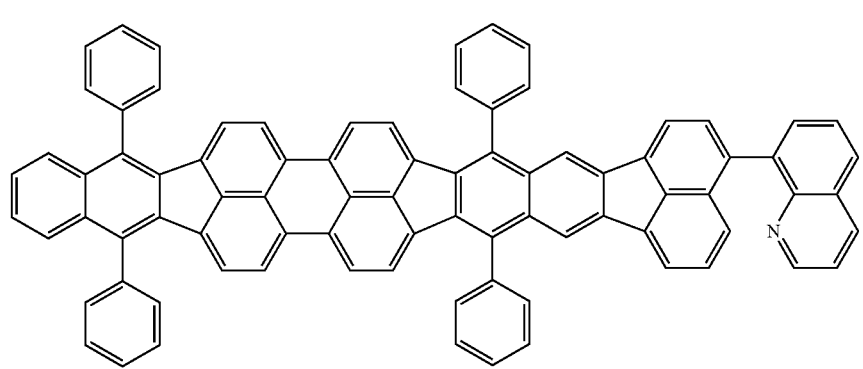<br>C16 |
| Example | Raw material 1 | Raw material 2 | Raw material 3 | m/z |
|---|---|---|---|---|
| 25 | | | | 1005 |

TABLE 11-continued
| | | | |
|---|---|---|---|
| 26 | 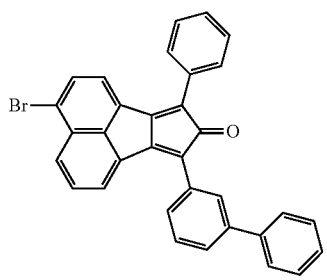 [SMILES: O=C1C(c2ccccc2)=C2C(=C1c1cccc(-c3ccccc3)c1)c1cccc3c(Br)ccc2c13] | 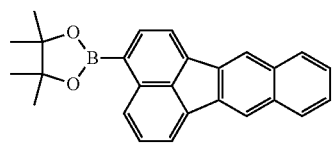 [SMILES: CC1(C)OB(c2ccc3c4c(cccc24)-c2cc4ccccc4cc2-3)OC1(C)C] | 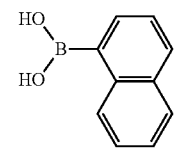 [SMILES: OB(O)c1cccc2ccccc12] 853 |
| 27 | 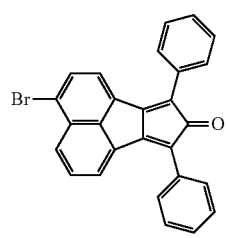 [SMILES: O=C1C(c2ccccc2)=C2C(=C1c1ccccc1)c1ccc(Br)c3cccc2c13] | 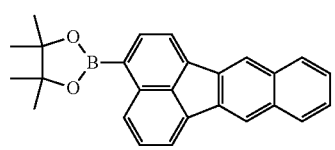 [SMILES: CC1(C)OB(c2ccc3c4c(cccc24)-c2cc4ccccc4cc2-3)OC1(C)C] | 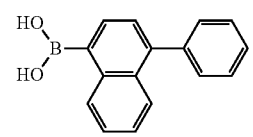 [SMILES: OB(O)c1ccc(-c2ccccc2)c2ccccc12] 853 |
| 28 | 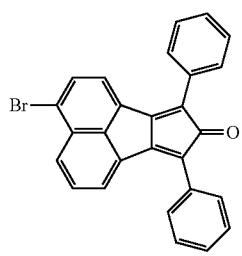 [SMILES: O=C1C(c2ccccc2)=C2C(=C1c1ccccc1)c1ccc(Br)c3cccc2c13] | 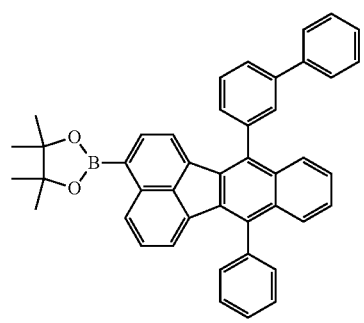 [SMILES: CC1(C)OB(c2ccc3c4c(cccc24)-c2c-3c(-c3cccc(-c4ccccc4)c3)c3ccccc3c2-c2ccccc2)OC1(C)C] | 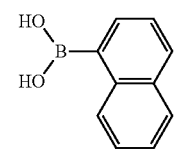 [SMILES: OB(O)c1cccc2ccccc12] 1005 |
| 29 | 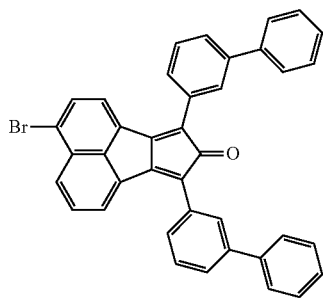 [SMILES: O=C1C(c2cccc(-c3ccccc3)c2)=C2C(=C1c1cccc(-c3ccccc3)c1)c1ccc(Br)c3cccc2c13] | 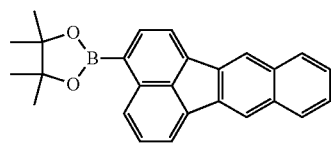 [SMILES: CC1(C)OB(c2ccc3c4c(cccc24)-c2cc4ccccc4cc2-3)OC1(C)C] | 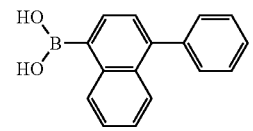 [SMILES: OB(O)c1ccc(-c2ccccc2)c2ccccc12] 1005 |
| 30 | 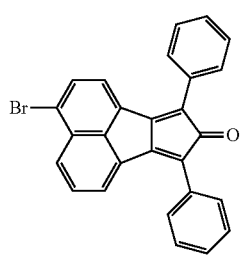 [SMILES: O=C1C(c2ccccc2)=C2C(=C1c1ccccc1)c1ccc(Br)c3cccc2c13] | 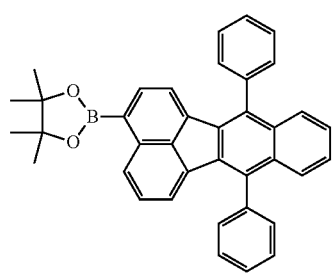 [SMILES: CC1(C)OB(c2ccc3c4c(cccc24)-c2c-3c(-c3ccccc3)c3ccccc3c2-c2ccccc2)OC1(C)C] | 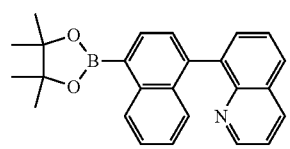 [SMILES: CC1(C)OB(c2ccc(-c3cccc4cccnc34)c3ccccc23)OC1(C)C] 1056 |

TABLE 12
| Example | Exemplary compound |
| --- | --- |
| 31 | 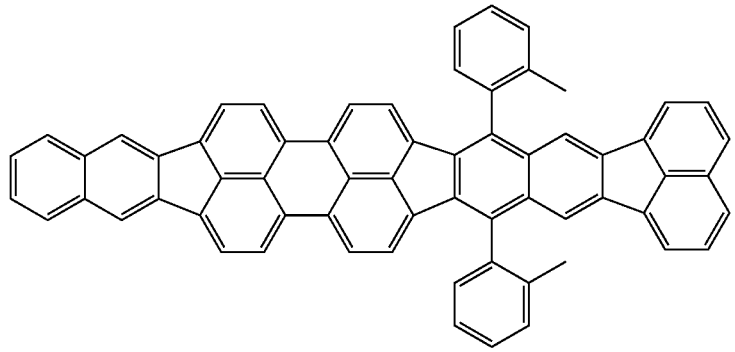 D1 |
| 32 | 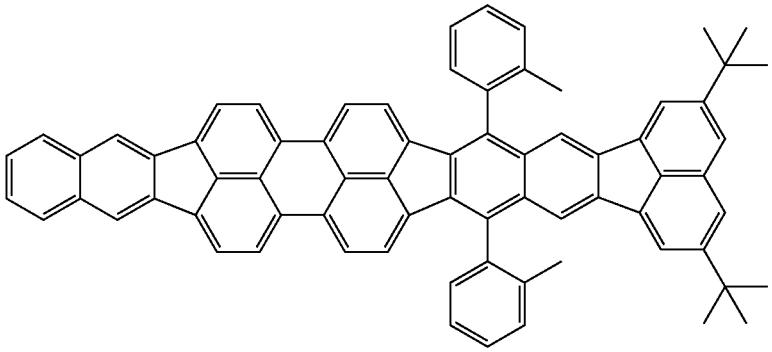 D3 |
| 33 | 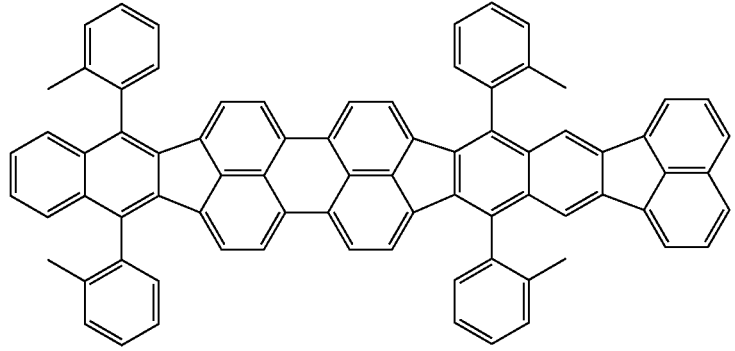 D7 |

TABLE 12-continued
| | |
|---|---|
| 34 | 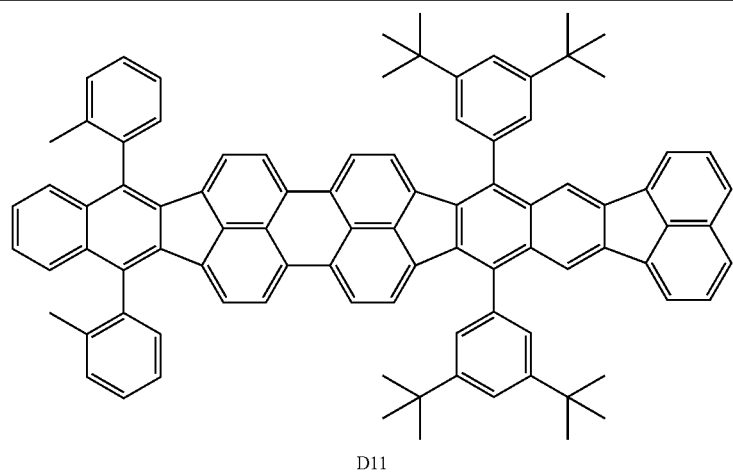<br>D11 |
| 35 | 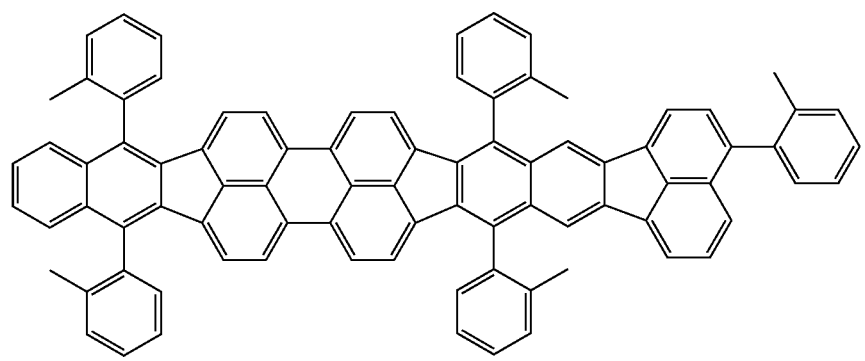<br>D14 |
| 36 | 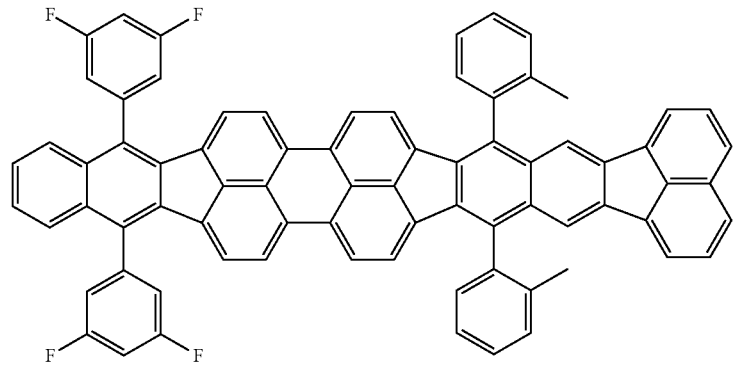<br>D16 |
| 37 | 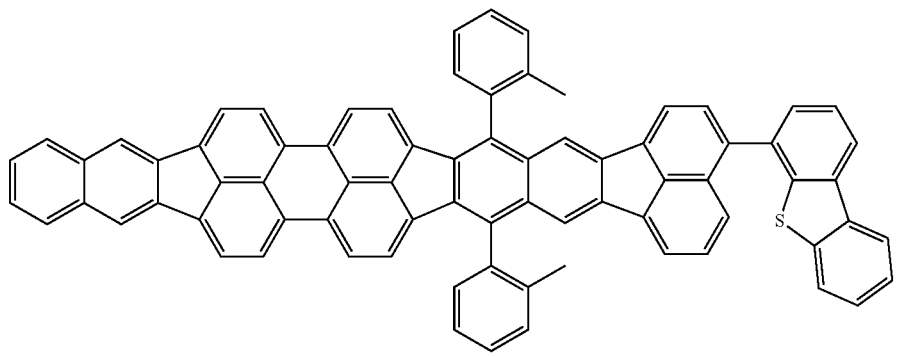<br>D19 |

TABLE 12-continued

| Example | Raw material 1 | Raw material 2 | Raw material 3 | m/z |
|---------|----------------|----------------|----------------|-----|
| 31 | | | | 805 |
| 32 | | | | 917 |
| 33 | | | | 985 |
| 34 | | | | 1182 |
| 35 | | | | 1075 |

TABLE 12-continued
| | | | |
|---|---|---|---|
| 36 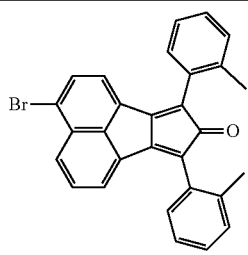 | 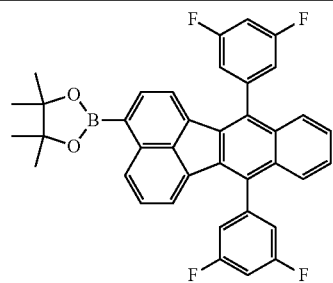 | 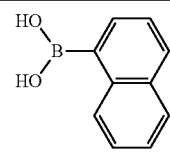 | 1029 |
| 37 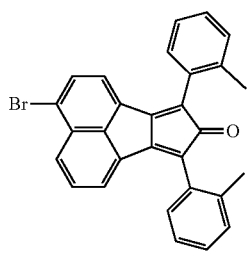 [SMILES: Cc1ccccc1C1=C2C(=C(c3ccccc3C)C1=O)c1ccc(Br)c3cccc2c13] | 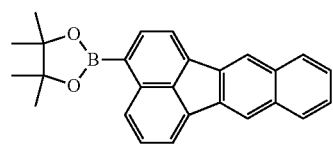 [SMILES: CC1(C)OB(c2ccc3c4c(cccc24)-c2cc4ccccc4cc2-3)OC1(C)C] | 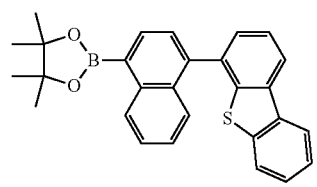 [SMILES: CC1(C)OB(c2ccc(-c3cccc4c3sc3ccccc34)c3ccccc23)OC1(C)C] | 987 |
TABLE 13
| Example | Exemplary compound |
|---|---|
| 38 | 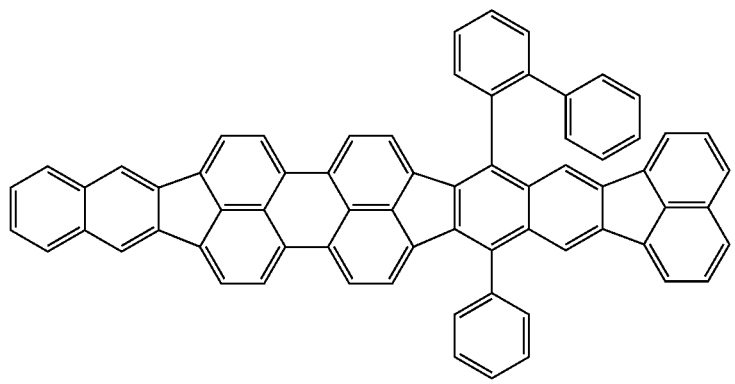<br>E1 |
| 39 | 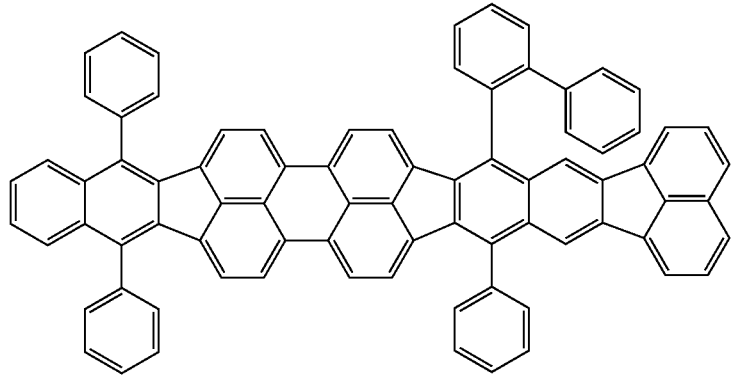<br>E6 |

TABLE 13-continued
40
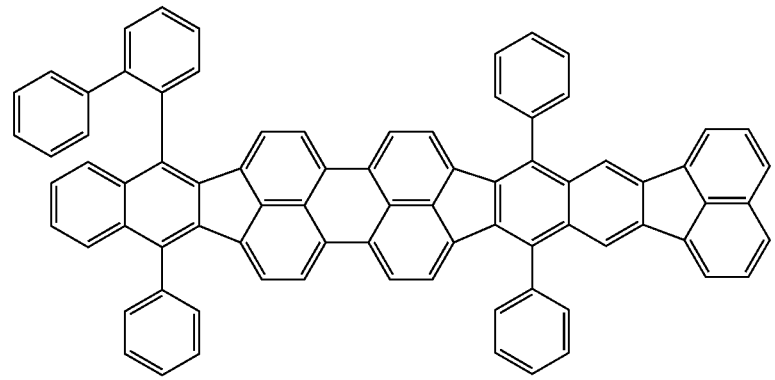
E7
41
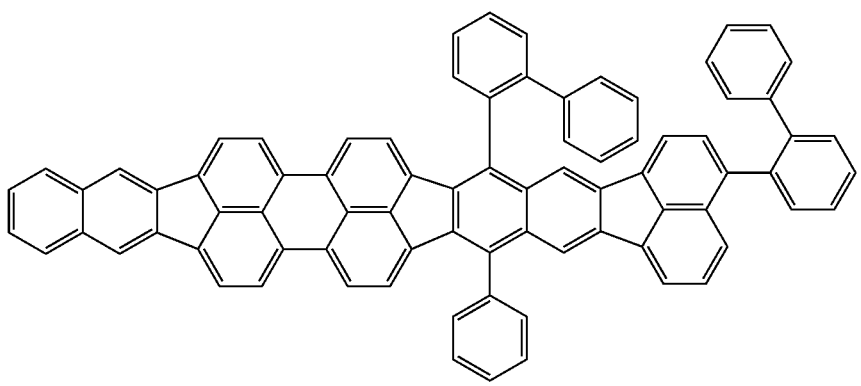
E9
42
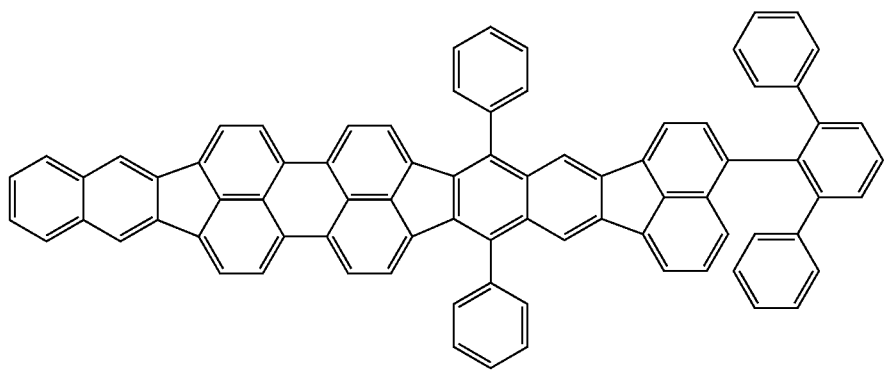
E10
43
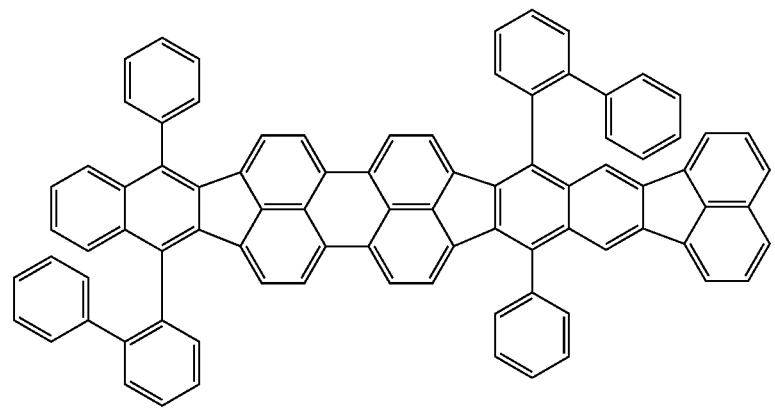
E11

TABLE 13-continued
44
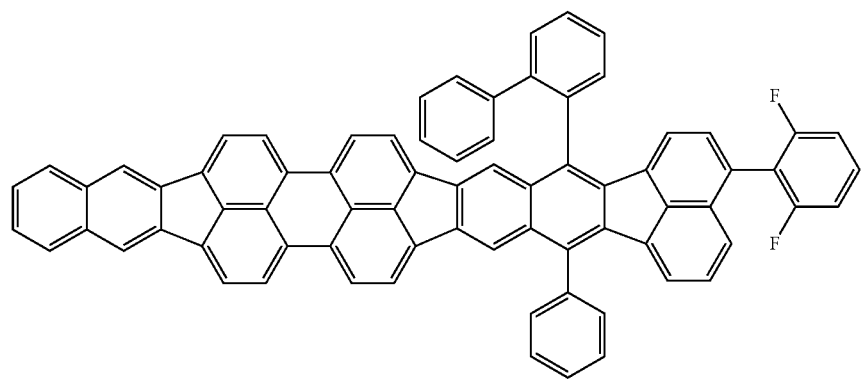
E19
45
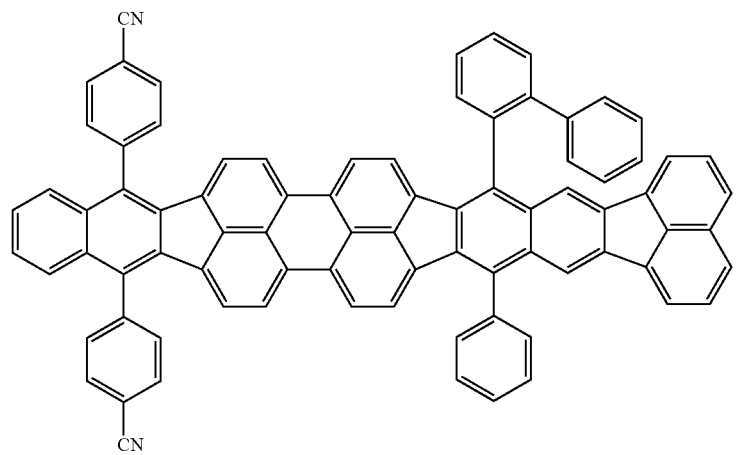
E20
| Example | Raw material 1 | Raw material 2 | Raw material3 | m/z |
|---|---|---|---|---|
| 38 | | | | 853 |
| 39 | | | | 1005 |

TABLE 13-continued
| 40 | 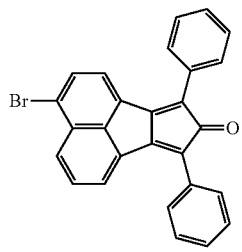 [SMILES: O=C1C(c2ccccc2)=C2C(=C1c1ccccc1)c1ccc(Br)c3cccc2c13] | 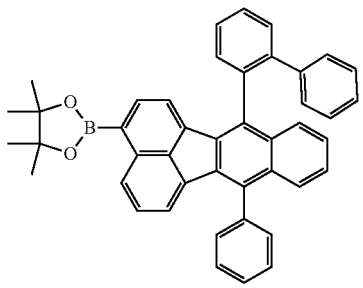 [SMILES: CC1(C)OB(c2ccc3c4c(cccc24)-c2c-3c(-c3ccccc3-c3ccccc3)c3ccccc3c2-c2ccccc2)OC1(C)C] | 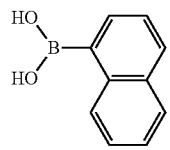 | 1005 |
| 41 | 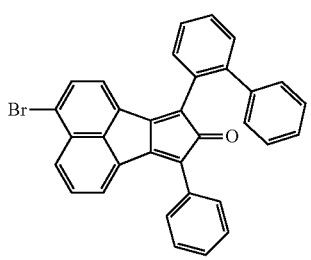 [SMILES: O=C1C(c2ccccc2)=C2C(=C1c1ccccc1-c1ccccc1)c1ccc(Br)c3cccc2c13] | 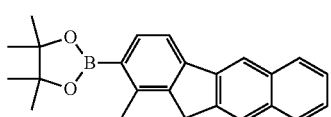 | 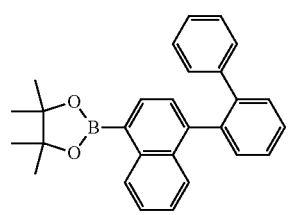 [SMILES: CC1(C)OB(c2ccc(-c3ccccc3-c3ccccc3)c3ccccc23)OC1(C)C] | 1005 |
| 42 | 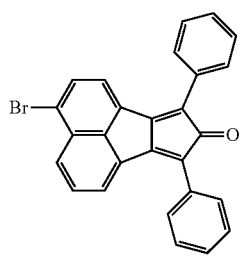 [SMILES: O=C1C(c2ccccc2)=C2C(=C1c1ccccc1)c1ccc(Br)c3cccc2c13] | 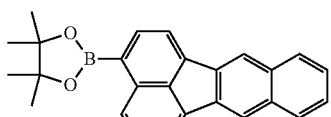 | 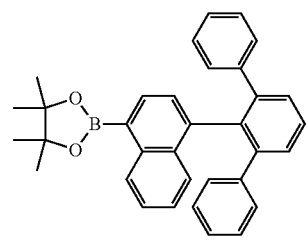 [SMILES: CC1(C)OB(c2ccc(-c3c(-c4ccccc4)cccc3-c3ccccc3)c3ccccc23)OC1(C)C] | 1005 |
| 43 | 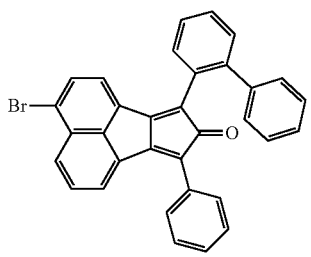 [SMILES: O=C1C(c2ccccc2)=C2C(=C1c1ccccc1-c1ccccc1)c1ccc(Br)c3cccc2c13] | 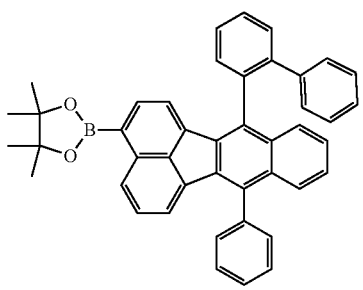 [SMILES: CC1(C)OB(c2ccc3c4c(cccc24)-c2c-3c(-c3ccccc3-c3ccccc3)c3ccccc3c2-c2ccccc2)OC1(C)C] | 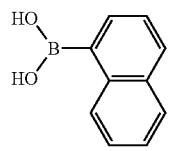 | 1081 |
| 44 | 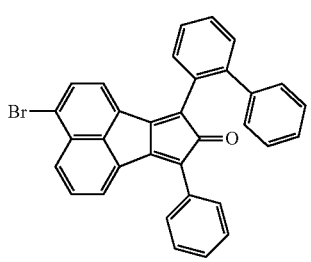 [SMILES: O=C1C(c2ccccc2)=C2C(=C1c1ccccc1-c1ccccc1)c1ccc(Br)c3cccc2c13] | 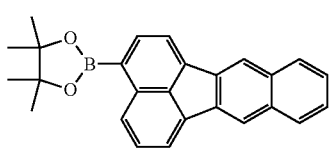 [SMILES: CC1(C)OB(c2ccc3c4c(cccc24)-c2cc4ccccc4cc2-3)OC1(C)C] | 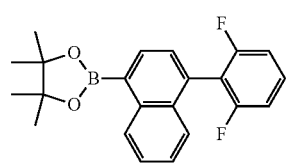 [SMILES: CC1(C)OB(c2ccc(-c3c(F)cccc3F)c3ccccc23)OC1(C)C] | 965 |

TABLE 13-continued

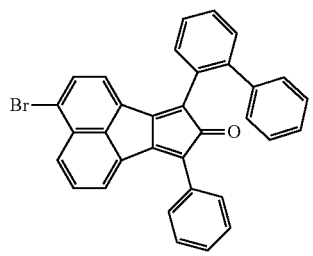 [SMILES: O=C1C(c2ccccc2)=C2C(=C1c1ccccc1-c1ccccc1)c1ccc(Br)c3cccc2c13]
45

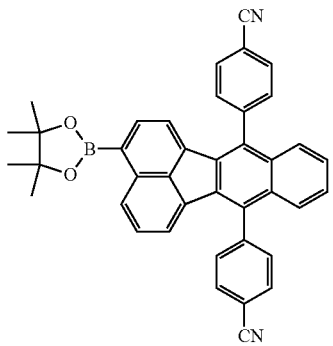 [SMILES: CC1(C)OB(c2ccc3c4c(cccc24)-c2c-3c(-c3ccc(C#N)cc3)c3ccccc3c2-c2ccc(C#N)cc2)OC1(C)C]

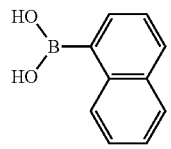
1055

Example 46

A bottom-emission-type organic light-emitting element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, an ITO film was formed on a glass substrate and subjected to desired patterning to form an ITO electrode (anode). At this time, the thickness of the ITO electrode was set to 100 nm. The substrate on which the ITO electrode was formed in this manner was used as an ITO substrate in the following process. Next, organic compound layers and an electrode layer shown in Table 14 were continuously formed on the ITO substrate by performing vacuum deposition by resistance heating in a vacuum chamber at $1.33 \times 10^{-4}$ Pa. At this time, the electrode area of the counter electrode (metal electrode layer, cathode) was set to 3 mm$^2$.

TABLE 14

| | Material | | | Thickness (nm) |
|---|---|---|---|---|
| Cathode | | Al | | 100 |
| Electron injection layer (EIL) | | LiF | | 1 |
| Electron transport layer (ETL) | | ET5 | | 20 |
| Hole blocking layer (HBL) | | ET17 | | 20 |
| Light-emitting layer (EML) | Host Guest | EM17 C2 | Weight ratio EM17:C2 = 99.7:0.3 | 30 |

TABLE 14-continued

| | Material | Thickness (nm) |
|---|---|---|
| Electron blocking layer (EBL) | HT12 | 15 |
| Hole transport layer (HTL) | HT3 | 30 |
| Hole injection layer (HIL) | HT16 | 5 |

The element obtained was measured and evaluated for its characteristics. The light-emitting element had a maximum emission wavelength of 622 nm and a maximum external quantum efficiency (E.Q.E.) of 5.5% and emitted red light with a chromaticity of (X, Y)=(0.67, 0.33). Furthermore, a continuous driving test at a current density of 100 mA/cm$^2$ was performed to measure the time taken for a decrease in luminance to reach 5%. The time exceeded 500 hours. Specifically, as measuring apparatuses, a 4140B microammeter manufactured by Hewlett-Packard Company was used to measure the current-voltage characteristics, and a BM7 manufactured by TOPCON Corporation was used to measure the emission luminance.

Examples 47 to 60 and Comparative Examples 3 and 4

Organic light-emitting elements were produced in the same manner as in Example 46 except that the compounds in Example 46 were appropriately changed to those shown in Table 15. The elements obtained were measured and evaluated for their characteristics in the same manner as in Example 46. The measurement results are shown in Table 15.

TABLE 15

| | EML | | | | | | | E.Q.E | Chromaticity coordinates of red |
|---|---|---|---|---|---|---|---|---|---|
| | HIL | HTL | EBL | Host | Guest | HBL | ETL | [%] | (x, y) |
| Example 24 | HT16 | HT2 | HT11 | EM17 | C4 | ET12 | ET2 | 5.8 | (0.68, 0.33) |
| Example 25 | HT16 | HT2 | HT12 | EM17 | C4 | ET12 | ET2 | 5.7 | (0.67, 0.33) |
| Example 26 | HT16 | HT2 | HT11 | EM17 | C10 | ET12 | ET2 | 5.9 | (0.68, 0.32) |
| Example 27 | HT15 | HT6 | HT8 | EM17 | C11 | ET10 | ET2 | 5.8 | (0.67, 0.33) |
| Example 28 | HT16 | HT2 | HT8 | EM16 | D7 | ET12 | ET3 | 5.9 | (0.67, 0.33) |
| Example 29 | HT16 | HT2 | HT12 | EM17 | D11 | ET10 | ET2 | 6.0 | (0.68, 0.32) |
| Example 30 | HT16 | HT1 | HT8 | EM16 | D16 | ET18 | ET3 | 6.0 | (0.67, 0.32) |
| Example 31 | HT16 | HT2 | HT12 | EM16 | E1 | ET12 | ET2 | 5.7 | (0.67, 0.33) |
| Example 32 | HT16 | HT2 | HT8 | EM17 | E6 | ET18 | ET2 | 5.9 | (0.68, 0.32) |
| Example 33 | HT16 | HT2 | HT8 | EM17 | E7 | ET18 | ET2 | 5.9 | (0.68, 0.32) |

TABLE 15-continued

|  | | | | EML | | | | E.Q.E | Chromaticity coordinates of red |
|---|---|---|---|---|---|---|---|---|---|
|  | HIL | HTL | EBL | Host | Guest | HBL | ETL | [%] | (x, y) |
| Example 34 | HT16 | HT1 | HT12 | EM16 | E9 | ET10 | ET3 | 5.8 | (0.67, 0.33) |
| Example 35 | HT16 | HT1 | HT12 | EM16 | E10 | ET10 | ET3 | 5.7 | (0.67, 0.32) |
| Example 36 | HT16 | HT2 | HT8 | EM17 | E19 | ET18 | ET3 | 5.6 | (0.67, 0.32) |
| Example 37 | HT17 | HT6 | HT8 | EM17 | E20 | ET18 | ET3 | 5.8 | (0.68, 0.33) |
| Comparative Example 3 | HT16 | HT3 | HT12 | EM17 | Comparative compound (2) | ET17 | ET5 | 4.7 | (0.66, 0.35) |
| Comparative Example 4 | HT16 | HT3 | HT12 | EM17 | Comparative compound (3) | ET17 | ET5 | 5.3 | (0.65, 0.34) |

Table 15 shows that the chromaticity coordinates in Comparative Example 3 and Comparative Example 4 were (0.66, 0.35) and (0.65, 0.34), respectively, and the chromaticity coordinates in Examples are located so as to expand the color reproduction range closer to the color reproduction range of sRGB. This is because the compound of the present disclosure emits red light at a longer wavelength.

Example 61

A top-emission-type organic light-emitting element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film with a thickness of 40 nm was formed on a glass substrate by sputtering and patterned by photolithography to form an anode. At this time, the electrode area of the counter electrode (metal electrode layer, cathode) was set to 3 mm$^2$. Subsequently, the cleaned substrate on which the electrode had been formed and materials were placed in a vacuum deposition apparatus (manufactured by ULVAC, Inc.). The apparatus was evacuated to $1.33 \times 10^{-4}$ Pa ($1 \times 10^{-6}$ Torr), and UV/ozone cleaning was then performed. Thereafter, layers were formed so as to be configured as shown in Table 16. Lastly, sealing was performed in a nitrogen atmosphere.

TABLE 16

| | Material | | Thickness (nm) |
|---|---|---|---|
| Cathode | Mg Ag | Weight ratio Mg:Ag = 50:50 | 10 |
| Electron injection layer (EIL) | LiF | | 1 |

TABLE 16-continued

| | Material | | | Thickness (nm) |
|---|---|---|---|---|
| Electron transport layer (ETL) | | ET2 | | 30 |
| Hole blocking layer (HBL) | | ET12 | | 70 |
| Second light-emitting layer (2nd EML) | Second host Second guest (blue dopant) | EM1 BD5 | Weight ratio EM1:BD5 = 99.4:0.6 | 10 |
| First light-emitting layer (1st EML) | First host First guest (red dopant) Third guest (green dopant) | EM1 C7 GD8 | Weight ratio EM1:C7:GD8 = 96.7:0.3:3.0 | 10 |
| Electron blocking layer (EBL) | | HT7 | | 10 |
| Hole transport layer (HTL) | | HT2 | | 20 |
| Hole injection layer (HIL) | | HT16 | | 5 |

The element obtained was measured and evaluated for its characteristics. The element obtained exhibited good white-light emission. The chromaticity coordinates of red after transmission through an RGB color filter were estimated from the white-light emission spectrum obtained. The chromaticity coordinates of red in sRGB were (0.68, 0.32).

Examples 62 to 66 and Comparative Examples 5 and 6

Organic light-emitting elements were produced in the same manner as in Example 61 except that the compounds in Example 61 were appropriately changed to those shown in Table 17. The elements obtained were measured and evaluated for their characteristics in the same manner as in Example 61. The measurement results are shown in Table 17.

TABLE 17

| | 1st EML | | | 2nd EML | | Chromaticity coordinates of red (x, y) |
|---|---|---|---|---|---|---|
| | First host | First guest | Third guest | Second host | Second guest | |
| Example 39 | EM5 | D7 | GD8 | EM1 | BD5 | (0.68, 0.33) |
| Example 40 | EM1 | D11 | GD9 | EM5 | BD7 | (0.68, 0.32) |
| Example 41 | EM5 | E1 | GD4 | EM5 | BD4 | (0.68, 0.33) |
| Example 42 | EM1 | E6 | GD7 | EM1 | BD6 | (0.69, 0.32) |
| Example 43 | EM11 | E9 | GD4 | EM11 | BD6 | (0.68, 0.33) |
| Comparative Example 3 | EM1 | Comparative compound (2) | GD4 | EM1 | BD6 | (0.67, 0.35) |

TABLE 17-continued

| | 1st EML | | | 2nd EML | | Chromaticity coordinates of red (x, y) |
|---|---|---|---|---|---|---|
| | First host | First guest | Third guest | Second host | Second guest | |
| Comparative Example 4 | EM1 | Comparative compound (3) | GD4 | EM1 | BD6 | (0.66, 0.34) |

Table 17 shows that the chromaticity coordinates of red in Comparative Example 3 and Comparative Example 4 were (0.67, 0.35) and (0.65, 0.34), respectively, and the chromaticity coordinates in Examples are located so as to expand the color reproduction range closer to the color reproduction range of the red region of sRGB. This is because the compound of the present disclosure emits red light at a longer wavelength.

The organic compound according to one embodiment of the present disclosure is an organic compound that emits long-wavelength red light. Thus, using the organic compound according to one embodiment of the present disclosure as a constituent material for an organic light-emitting element can provide an organic light-emitting element having good light-emitting properties and high durability.

According to the present disclosure, an organic compound having a basic skeleton that emits long-wavelength red light can be provided.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-187928, filed Oct. 3, 2018 and Japanese Patent Application No. 2018-195285, filed Oct. 16, 2018 which are hereby incorporated by reference herein in their entirety.

What is claimed is:

1. An organic compound represented by formula (1):

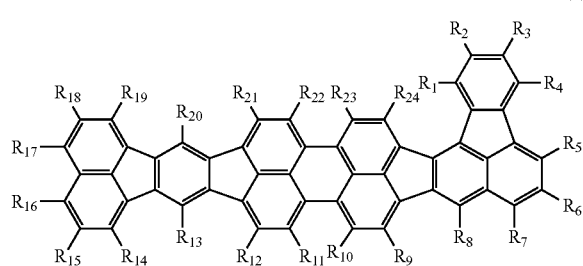

(1)

wherein $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein in formula (1), at least one of $R_1$ to $R_{24}$ is the aryl group.

3. The organic compound according to claim 2, wherein the aryl group is a phenyl group, and the phenyl group has a substituent at an ortho position.

4. The organic compound according to claim 3, wherein the substituent at the ortho position of the phenyl group is selected from a halogen atom, a substituted or unsubstituted alkyl group, a substituted or unsubstituted aryl group, a substituted or unsubstituted heterocyclic group, and a cyano group.

5. The organic compound according to claim 4, wherein the substituent at the ortho position of the phenyl group is selected from a phenyl group and an alkyl group having 1 to 10 carbon atoms.

6. The organic compound according to claim 1, wherein in formula (1), at least two of $R_8$, $R_{13}$, and $R_{20}$ are each the aryl group.

7. The organic compound according to claim 6, wherein in formula (1), $R_8$, $R_{13}$, and $R_{20}$ are each the aryl group.

8. An organic compound represented by formula (2):

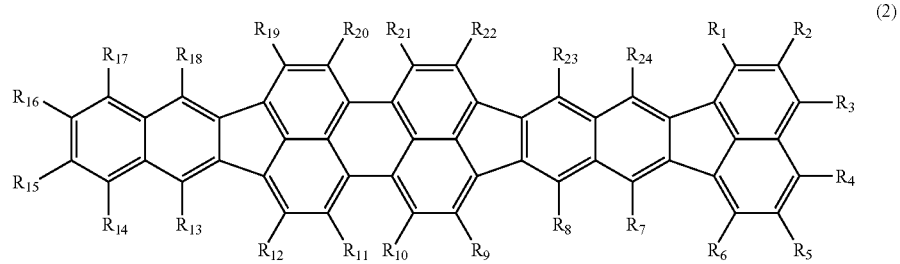

(2)

wherein $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

9. The organic compound according to claim 8, wherein $R_1$ to $R_{24}$ are each independently selected from the group consisting of a hydrogen atom, a substituted or unsubstituted alkyl group having 1 to 10 carbon atoms, and a substituted or unsubstituted aryl group having 6 to 18 carbon atoms.

10. The organic compound according to claim 9, wherein the aryl group has a substituent at an ortho position.

11. An organic light-emitting element comprising:
a first electrode;
a second electrode; and
an organic compound layer disposed between the first electrode and the second electrode,
wherein the organic compound layer contains the organic compound according to claim 1.

12. The organic light-emitting element according to claim 11, wherein the organic compound layer includes a light-emitting layer.

13. The organic light-emitting element according to claim 12, wherein the organic compound layer further includes another light-emitting layer stacked on the light-emitting layer, and the other light-emitting layer emits light having a color different from a color of light emitted from the light-emitting layer.

14. The organic light-emitting element according to claim 13, wherein the organic light-emitting element emits white light.

15. An organic light-emitting element comprising:
a first electrode;
a second electrode; and
an organic compound layer disposed between the first electrode and the second electrode,
wherein the organic compound layer contains the organic compound according to claim 8.

16. A display apparatus comprising a plurality of pixels,
wherein the plurality of pixels each include the organic light-emitting element according to claim 11 and a transistor connected to the organic light-emitting element.

17. An image pickup apparatus comprising:
an optical unit including a plurality of lenses;
an image pickup element that receives light that has passed through the optical unit; and
a display unit that displays an image,
wherein the display unit displays an image captured by the image pickup element, and the display unit includes the organic light-emitting element according to claim 11.

18. An electronic device comprising:
a display unit including the organic light-emitting element according to claim 11;
a housing provided with the display unit; and
a communication unit that is provided in the housing and communicates with an outside.

19. A display apparatus comprising a plurality of pixels,
wherein the plurality of pixels each include the organic light-emitting element according to claim 12 and a transistor connected to the organic light-emitting element.

20. A moving object comprising:
a lighting fixture including the organic light-emitting element according to claim 11; and
a body provided with the lighting fixture.

* * * * *